United States Patent
Sredni et al.

(10) Patent No.: US 11,197,863 B2
(45) Date of Patent: Dec. 14, 2021

(54) INHIBITORS OF POLO-LIKE KINASE 4 (PLK4) FOR TREATING PEDIATRIC EMBRYONAL TUMORS

(71) Applicant: ANN AND ROBERT H. LURIE CHILDREN'S HOSPITAL OF CHICAGO, Chicago, IL (US)

(72) Inventors: Simone T. Sredni, Chicago, IL (US); Tadanori Tomita, Glenview, IL (US)

(73) Assignee: ANN AND ROBERT H. LURIE CHILDREN'S HOSPITAL OF CHICAGO, Chicago, IL (US)

( * ) Notice: Subject to any disclaimer, the term of this patent is extended or adjusted under 35 U.S.C. 154(b) by 0 days.

(21) Appl. No.: 16/116,000

(22) Filed: Aug. 29, 2018

(65) Prior Publication Data

US 2019/0070190 A1 Mar. 7, 2019

Related U.S. Application Data

(60) Provisional application No. 62/551,526, filed on Aug. 29, 2017.

(51) Int. Cl.
*A61K 31/5377* (2006.01)
*A61P 35/00* (2006.01)
*A61K 45/06* (2006.01)
*A61K 9/00* (2006.01)

(52) U.S. Cl.
CPC ........ *A61K 31/5377* (2013.01); *A61K 9/0053* (2013.01); *A61K 45/06* (2013.01); *A61P 35/00* (2018.01)

(58) Field of Classification Search
CPC .. A61K 31/5377; A61K 45/06; A61K 9/0053; A61P 35/00
USPC .................................................. 514/234.5
See application file for complete search history.

(56) References Cited

FOREIGN PATENT DOCUMENTS

| WO | WO-2012048411 A1 * | 4/2012 | ........... C07D 403/14 |
|---|---|---|---|
| WO | WO-2016166604 A1 * | 10/2016 | ........... C07D 403/12 |

OTHER PUBLICATIONS

Puri et al., Pediatr. Blood Cancer 2008; 50:167-169 (Year: 2008).*
Sredni et al Pediatr. Blood Cancer, 2017, 64(11) pp. 1-10 (Year: 2017).*
Acilan C, Saunders WS. A tale of too many centrosomes. Cell. 2008; 134:572-5.
Aisner J, Lee EJ. Etoposide. Current and future status. Cancer. 1991; 67:215-9.
Albanese P, Belin MF, Delattre O. The tumour suppressor hSNF5/INI1 controls the differentiation potential of malignant rhabdoid cells. Eur J Cancer. 2006;42(14):2326-2334.
Alimova I, Birks DK, Harris PS, et al. Inhibition of EZH2 suppresses self-renewal and induces radiation sensitivity in atypical rhabdoid teratoid tumor cells. Neuro-oncology. 2013; 15(2):149-160.
Barr FA, Sillje HH, Nigg EA. Polo-like kinases and the orchestration of cell division. Nat Rev Mol Cell Biol. 2004; 5:429-40. https://doi.org/10.1038/nrm1401.
Basto R, Brunk K, Vinadogrova T, et al. Centrosome amplification can initiate tumorigenesis in flies. Cell. 2008;133(6):1032-1042.
Berger T, Saunders ME, Mak TW. Beyond the oncogene revolution: four new ways to combat cancer. Cold Spring Harb Symp Quant Biol. 2016;81:85-92.
Bettencourt-Dias M, Rodrigues-Martins A, Carpenter L, et al. SAK/PLK4 is required for centriole duplication and flagella development. Curr Biol. 2005;15(24):2199-2207.
Birks DK, Donson AM, Patel PR, et al. Pediatric rhabdoid tumors of kidney and brain show many differences in gene expression but share dysregulation of cell cycle and epigenetic effector genes. Pediatr Blood Cancer. 2013;60(7):1095-1102.
Bourdeaut F, Chi SN, Fruhwald MC. Rhabdoid tumors: integrating biological insights with clinical success: a report from the SMARCB1 and rhabdoid tumor symposium, Paris, Dec. 12-14, 2013. Cancer Genet. 2014; 207:346-51.
Cappetta D, Rossi F, Piegari E, Quaini F, Berrino L, Urbanek K, De Angelis A. Doxorubicin targets multiple players: a new view of an old problem. Pharmacol Res. 2017.
Castedo M, Perfettini JL, Roumier T, Andreau K, Medema R, Kroemer G. Cell death by mitotic catastrophe: a molecular definition. Oncogene. 2004; 23:2825-37.
Chi SN, Zimmerman MA, Yao X, Cohen KJ, Burger P, Biegel JA, Rorke-Adams LB, Fisher MJ, Janss A, Mazewski C, Goldman S, Manley PE, Bowers DC, et al. Intensive multimodality treatment for children with newly diagnosed CNS atypical teratoid rhabdoid tumor. J Clin Oncol. 2009; 27:385-9.
Chico LK, Van Eldik LJ, Watterson DM. Targeting protein kinases in central nervous system disorders. Nat Rev Drug Discov. 2009; 8:892-909.
Cho SW, Kim S, Kim JM, et al. Targeted genome engineering in human cells with the Cas9 RNA-guided endonuclease. Nat Biotechnol. 2013;31(3):230-232.
Chun HJ, Lim EL, Heravi-Moussavi A, et al. Genome-wide profiles of extra-cranial malignant rhabdoid tumors reveal heterogeneity and dysregulated developmental pathways. Cancer Cell. 2016;29(3):394-406.
Cohen P. Protein kinases—the major drug targets of the twenty-first century? Nat Rev Drug Discov. 2002; 1:309-15.
Demidenko ZN, Blagosklonny MV. Quantifying pharmacologic suppression of cellular senescence: prevention of cellular hypertrophy versus preservation of proliferative potential. Aging (Albany NY). 2009; 1:1008-16.
Fabbro D, Cowan-Jacob SW, Mobitz H, Martiny-Baron G. Targeting cancer with small-molecular-weight kinase inhibitors. Kinase Inhibitors. Methods in Molecular Biology (Methods and Protocols). 2012; 795:1-34.
Fedorov O, Muller S, Knapp S. The (un)targeted cancer kinome. Nat Chem Biol. 2010;6(3): 166-169.
Fleuren ED, Zhang L, Wu J, et al. The kinome 'at large' in cancer. Nat Rev Cancer. 2016;16(2):83-98.

(Continued)

*Primary Examiner* — Yevgeny Valenrod
(74) *Attorney, Agent, or Firm* — Quarles & Brady LLP

(57) ABSTRACT

Disclosed are methods and compositions for treating pediatric embryonal tumors. The methods and compositions utilize or include an inhibitor of polo-like kinase 4 (PLK4) for treating pediatric embryonal tumors.

11 Claims, 44 Drawing Sheets

(56) References Cited

OTHER PUBLICATIONS

Fruhwald MC, Biegel JA, Bourdeaut F, et al. Atypical teratoid/rhabdoid tumors—current concepts, advances in biology, and potential future therapies. Neuro-oncology. 2016;18(6):764-778.
Furtwangler R, Kager L, Melchior P, Rube C, Ebinger M, Nourkami-Tutdibi N, Niggli F, Warmann S, Hubertus J, Amman G, Leuschner I, Vokuhl C, Graf N, et al. High-dose treatment for malignant rhabdoid tumor of the kidney: no evidence for improved survival—the gesellschaft fur padiatrische onkologie und hamatologie (GPOH) experience. Pediatr Blood Cancer. 2017.
Gadd S, Sredni ST, Huang CC, et al. Rhabdoid tumor: gene expression clues to pathogenesis and potential therapeutic targets. Lab Invest. 2010;90(5):724-738.
Ginn KF, Gajjar A. Atypical teratoid rhabdoid tumor: current therapy and future directions. Front Oncol. 2012;2:114.
Gross S, Rahal R, Stransky N, Lengauer C, Hoeflich KP. Targeting cancer with kinase inhibitors. J Clin Invest. 2015; 125:1780-9.
Grupenmacher AT, Halpern AL, Bonaldo Mde F, et al. Study of the gene expression and microRNA expression profiles of malignant rhabdoid tumors originated in the brain (AT/RT) and in the kidney (RTK). Child's Nerv Syst. 2013;29(11): 1977-1983.
Habedanck R, Stierhof YD, Wilkinson CJ, et al. The Polo kinase Plk4 functions in centriole duplication. Nat Cell Biol. 2005;7(11):1140-1146.
Hashizume R, Gupta N, Berger MS, et al. Morphologic and molecular characterization of ATRT xenografts adapted for orthotopic therapeutic testing. Neuro-oncology. 2010;12(4):366-376.
Hashizume R, Zhang A, Mueller S, et al. Inhibition of DNA damage repair by the CDK4/6 inhibitor palbociclib delays irradiated intracranial atypical teratoid rhabdoid tumor and glioblastoma xenograft regrowth. Neuro-oncology. 2016; 18(11):1519-1528.
Hau PM, Siu WY, Wong N, Lai PB, Poon RY. Polyploidization increases the sensitivity to DNA-damaging agents in mammalian cells. FEBS Lett. 2006; 580:4727-36.
Holland AJ, Cleveland DW. Polo-like kinase 4 inhibition: a strategy for cancer therapy? Cancer Cell. 2014;26(2):151-153.
Holland AJ, Lan W, Niessen S, et al. Polo-like kinase 4 kinase activity limits centrosome overduplication by autoregulating its own stability. J Cell Biol. 2010;188(2):191-198.
Itahana K, Campisi J, Dimri GP. Methods to detect biomarkers of cellular senescence: the senescence-associated beta-galactosidase assay. Methods Mol Biol. 2007; 371:21-31.
Ivanov DP, Coyle B, Walker DA, Grabowska AM. in vitro models of medulloblastoma: choosing the right tool for the job. J Biotechnol. 2016; 236:10-25.
Jiang W, Bikard D, Cox D, et al. RNA-guided editing of bacterial genomes using CRISPR-Cas systems. Nat Biotechnol. 2013;31(3):233-239.
Jinek M, Chylinski K, Fonfara I, et al. A programmable dual-RNA-guided DNA endonuclease in adaptive bacterial immunity. Science. 2012;337(6096):816-821.
Johann PD, Erkek S, Zapatka M, et al. Atypical teratoid/rhabdoid tumors are comprised of three epigenetic subgroups with distinct enhancer landscapes. Cancer Cell. 2016;29(3):379-393.
Kashem MA, Nelson RM, Yingling JD, Pullen SS, Prokopowicz AS 3rd, Jones JW, Wolak JP, Rogers GR, Morelock MM, Snow RJ, Homon CA, Jakes S. Three mechanistically distinct kinase assays compared: measurement of intrinsic ATPase activity identified the most comprehensive set of ITK inhibitors. J Biomol Screen. 2007; 12:70-83.
Kerl K, et al. The histone deacetylase inhibitor SAHA acts in synergism with fenretinide and doxorubicin to control growth of rhabdoid tumor cells. BMC Cancer. 2013; 13:286.
Kim KH, Kim W, Howard TP, et al. SWI/SNF-mutant cancers depend on catalytic and non-catalytic activity of EZH2. Nat Med. 2015;21(12):1491-1496.
Ko MA, Rosario CO, Hudson JW, et al. Plk4 haploinsufficiency causes mitotic infidelity and carcinogenesis. Nat Genet. 2005;37(8):883-888.
Kool M, et al. Molecular subgroups of medulloblastoma: an international meta-analysis of transcriptome, genetic aberrations, and clinical data of WNT, SHH, Group 3, and Group 4 medulloblastomas. Acta Neuropathol. 2012; 123:473-84.
Kramer KF, et al. BRD9 inhibition, alone or in combination with cytostatic compounds as a therapeutic approach in rhabdoid tumors, Int J Mol Sci. 2017; 18.
Lamothe SM, Guo J, Li W, Yang T, Zhang S. The human ether-a-go-go-related gene (hERG) potassium channel represents an unusual target for protease-mediated damage. J Biol Chem. 2016; 291:20387-401.
Lebakken CS, Riddle SM, Singh U, Frazee WJ, Eliason HC, Gao Y, Reichling LJ, Marks BD, Vogel KW. Development and applications of a broad-coverage, TR-FRET-based kinase binding assay platform. J Biomol Screen. 2009; 14:924-35.
Ledford H. CRISPR, the disruptor. Nature. 2015:522(7554):20-24.
Lee S, Cimica V, Ramachandra N, et al. Aurora A is a repressed effector target of the chromatin remodeling protein INI1/hSNF5 Required for Rhabdoid Tumor Cell Survival. Cancer Res. 2011;71(9):3225-3235.
Leung GC, Hudson JW, Kozarova A, Davidson A, Dennis JW, Sicheri F. The Sak polo-box comprises a structural domain sufficient for mitotic subcellular localization. Nat Struct Biol. 2002; 9:719-24.
Liu L, Zhang CZ, Cai M, et al. Downregulation of polo-like kinase 4 in hepatocellular carcinoma associates with poor prognosis. PLoS ONE. 2012;7(7):e41293.
Liu Z, Sun Q, Wang X. PLK1, a potential target for cancer therapy. Transl Oncol. 2017; 10:22-32.
Lynch T, Price A. The effect of cytochrome P450 metabolism on drug response, interactions, and adverse effects. Am Fam Physician. 2007; 76:391-6.
Mali P, Yang L, Esvelt KM, et al. RNA-guided human genome engineering via Cas9. Science. 2013;339(6121):823-826.
Manning G, Whyte DB, Martinez R, et al. The protein kinase complement of the human genome. Science. 2002;298(5600):1912-1934.
Maris JM, Morton CL, Gorlick R, et al. Initial testing of the aurora kinase A inhibitor MLN8237 by the Pediatric Preclinical Testing Program (PPTP). Pediatr Blood Cancer. 2010;55(1):26-34.
Marks BD, Thompson DV, Goossens TA, Trubetskoy OV. High-throughput screening assays for the assessment of CYP2C9*1, CYP2C9*2, and CYP2C9*3 metabolism using fluorogenic Vivid substrates. J Biomol Screen. 2004; 9:439-49.
Mason JM, Lin DC, Wei X, et al. Functional characterization of CFI-400945, a Polo-like kinase 4 inhibitor, as a potential anticancer agent. Cancer Cell. 2014;26(2):163-176.
Mittal K, Ogden A, Reid MD, Rida PC, Varambally S, Aneja R. Amplified centrosomes may underlie aggressive disease course in pancreatic ductal adenocarcinoma. Cell Cycle. 2015; 14:2798-809.
Morozov A, Lee SJ, Zhang ZK, et al. INI1 induces interferon signaling and spindle checkpoint in rhabdoid tumors. Clin Cancer Res. 2007;13(16):4721-4730.
Muchardt C, Yaniv M. The mammalian SWI/SNF complex and the control of cell growth. Semin Cell Dev Biol. 1999; 10(2):189-195.
Nigg EA, Raff JW. Centrioles, centrosomes, and cilia in health and disease. Cell. 2009; 139:663-78.
Panigrahy D, Kaipainen A, Butterfield CE, Chaponis DM, Laforme AM, Folkman J, Kieran MW. Inhibition of tumor angiogenesis by oral etoposide. Exp Ther Med. 2010; 1:739-46.
Pardridge WM. Drug transport across the blood-brain barrier. J Cereb Blood Flow Metab. 2012; 32:1959-72.
Pardridge WM. The blood-brain barrier: bottleneck in brain drug development. NeuroRx. 2005; 2:3-14.
Piper DR, et al. Development of the predictor HERG fluorescence polarization assay using a membrane protein enrichment approach. Assay Drug Dev Technol. 2008; 6:213-23.
Ramaswamy V, Taylor MD. Medulloblastoma: from myth to molecular. J Clin Oncol. 2017; 35:2355-63.
Rosario CO, Kazazian K, Zih FS, et al. A novel role for Plk4 in regulating cell spreading and motility. Oncogene. 2015;34(26):3441-3451.

(56) References Cited

OTHER PUBLICATIONS

Rosson GB, Vincent TS, Oswald BW, Wright CF. Drug resistance in malignant rhabdoid tumor cell lines. Cancer Chemother Pharmacol. 2002; 49:142-8.

Sampson PB, et al. The discovery of polo-like kinase 4 inhibitors: identification of (1R,2S).2-(3-((E).4-(((cis).2,6-dimethylmorpholino)methyl)styryl). 1H.indazol-6-yl)-5-'-methoxyspiro[cyclopropane-1,3·'-indolin]-2·'-one (CFI-400945) as a potent, orally active antitumor agent. J Med Chem. 2015;58:147-169.

Sampson PB, Liu Y, Patel NK, et al. The discovery of Polo-like kinase 4 inhibitors: design and optimization of spiro[cyclopropane-1,3'[3H]indol]-2'(1'H).ones as orally bioavailable antitumor agents. J Med Chem. 2015;58(1):130-146.

Sander JD, Joung JK. CRISPR-Cas systems for editing, regulating and targeting genomes. Nat Biotechnol. 2014;32(4):347-355.

Schneider CA, Rasband WS, Eliceiri KW. NIH Image to ImageJ: 25 years of image analysis. Nat Methods. 2012;9(7):671-675.

Shalem O, Sanjana NE, Hartenian E, et al. Genome-scale CRISPR-Cas9 knockout screening in human cells. Science. 2014;343(6166):84-87.

Shinmura K, Kurabe N, Goto M, Yamada H, Natsume H, Konno H, Sugimura H. PLK4 overexpression and its effect on centrosome regulation and chromosome stability in human gastric cancer. Mol Biol Rep. 2014; 41:6635-44.

Sillibourne JE, Bornens M. Polo-like kinase 4: the odd one out of the family. Cell Div. 2010;5:25.

Sillibourne JE, Tack F, Vloemans N, et al. Autophosphorylation of polo-like kinase 4 and its role in centriole duplication. Mol Biol Cell. 2010;21(4):547-561.

Singh A, Lun X, Jayanthan A, et al. Profiling pathway-specific novel therapeutics in preclinical assessment for central nervous system atypical teratoid rhabdoid tumors (CNS ATRT): favorable activity of targeting EGFR-ErbB2 signaling with lapatinib. Mol Oncol. 2013;7(3):497-512.

Sredni ST, Huang CC, Pundy T, et al. A gene signature for a long-term survivor of an atypical teratoid/rhabdoid tumor. Cancer Genet. 2014;207(9):420-424.

Sredni ST, Patel K, D'Almeida Costa F, et al. Activation of ErbB2-ErbB3 signaling pathway supports potential therapeutic activity of ErbB inhibitors in AT/RT. J Neuro-oncol. 2014;118(1):201-203.

Sredni ST, Suzuki M, Yang JP, Topczewski J, Bailey AW, Gokirmak T, Gross JN, de Andrade A, Kondo A, Piper DR, Tomita T. A functional screening of the kinome identifies the polo-like kinase 4 as a potential therapeutic target for malignant rhabdoid tumors, and possibly, other embryonal tumors of the brain. Pediatr Blood Cancer. 2017.

Sredni ST, Tomita T. Rhabdoid tumor predisposition syndrome. Pediatr Dev Pathol. 2015;18(1):49-58.

Sredni ST, Tomita T. The polo-like kinase 4 gene (PLK4) is overexpressed in pediatric medulloblastoma. Childs Nerv Syst. 2017; 33:1031.

Srsen V, Merdes A. The centrosome and cell proliferation. Cell Div. 2006; 1:26.

Suzuki M, Kondo A, Ogino I, et al. Overexpression of TEAD4 in atypical teratoid/rhabdoid tumor: new insight to the pathophysiology of an aggressive brain tumor. Pediatr Blood Cancer. 2016;00:1-10, DOI: 10.1002/pbc.26398.

Taylor MD, Northcott PA, Korshunov A, Remke M, Cho YJ, Clifford SC, Eberhart CG, Parsons DW, Rutkowski S, Gajjar A, Ellison DW, Lichter P, Gilbertson RJ, et al. Molecular subgroups of medulloblastoma: the current consensus. Acta Neuropathol. 2012; 123:465-72.

Terzi MY, Izmirli M, Gogebakan B. The cell fate: senescence or quiescence. Mol Biol Rep. 2016; 43:1213-20.

Torchia J, Picard D, Lafay-Cousin L, et al. Molecular subgroups of atypical teratoid rhabdoid tumours in children: an integrated genomic and clinicopathological analysis. Lancet Oncol. 2015;16(5):569-582.

Tovar C, Higgins B, Deo D, Kolinsky K, Liu JJ, Heimbrook DC, Vassilev LT. Small-molecule inducer of cancer cell polyploidy promotes apoptosis or senescence: implications for therapy. Cell Cycle. 2010; 9:3364-75.

Venkataraman S, Alimova I, Tello T, et al. Targeting Aurora kinase A enhances radiation sensitivity of atypical teratoid rhabdoid tumor cells. J Neuro-oncol. 2012;107(3):517-526.

Versteege I, Medjkane S, Rouillard D, et al. A key role of the hSNF5/INI1 tumour suppressor in the control of the G1-S transition of the cell cycle. Oncogene. 2002;21(42):6403-6412.

Vogel KW, et al. Developing assays for kinase drug discovery—where have the advances come from? Expert Opin Drug Discov. 2008; 3:115-29.

Wang T, Wei JJ, Sabatini DM, et al. Genetic screens in human cells using the CRISPR-Cas9 system. Science. 2014;343(6166):80-84.

Wetmore C, Boyett J, Li SY, et al. Alisertib is active as single agent in recurrent atypical teratoid rhabdoid tumors in 4 children. Neuro-oncology. 2015;17(6):882-888.

Yu B, Yu Z, Qi PP, et al. Discovery of orally active anticancer candidate CFI-400945 derived from biologically promising spirooxindoles: success and challenges. Eur J Med Chem. 2015;95:35-40.

Zhang ZK, Davies KP, Allen J, et al. Cell cycle arrest and repression of cyclin D1 transcription by INI1/hSNF5. Mol Cell Biol. 2002;22(16):5975-5988.

Zheng B, Liang L, Huang S, et al. MicroRNA-409 suppresses tumour cell invasion and metastasis by directly targeting radixin in gastric cancers. Oncogene. 2012;31(42):4509-4516.

Zhou Y, Zhu S, Cai C, et al. High-throughput screening of a CRISPR/Cas9 library for functional genomics in human cells. Nature. 2014;509(7501):487-491.

\* cited by examiner

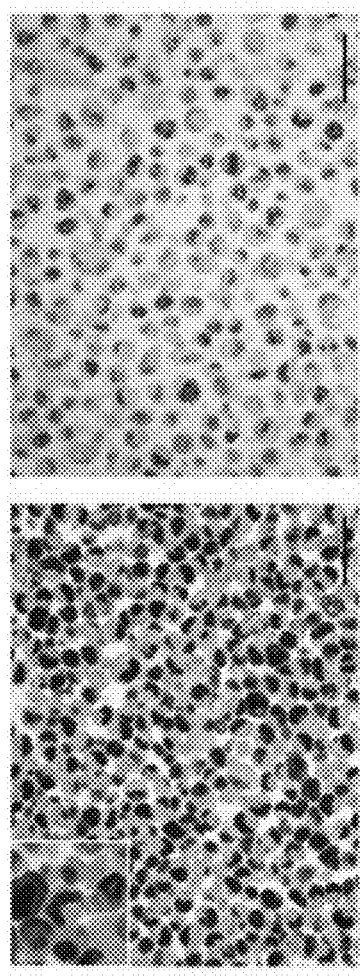
FIG. 3A
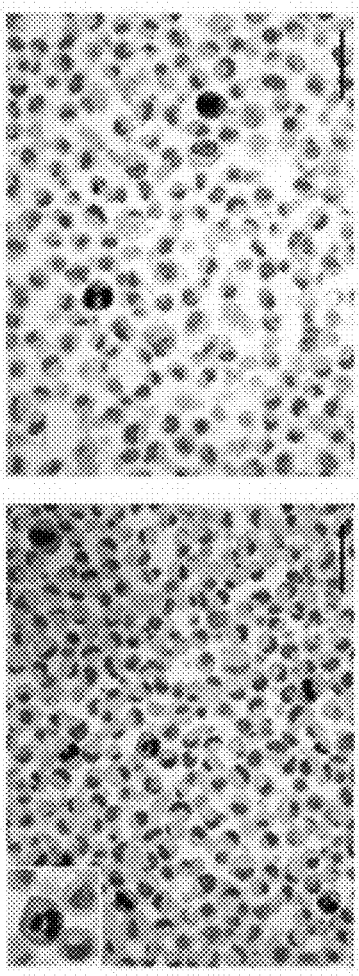
FIG. 3B
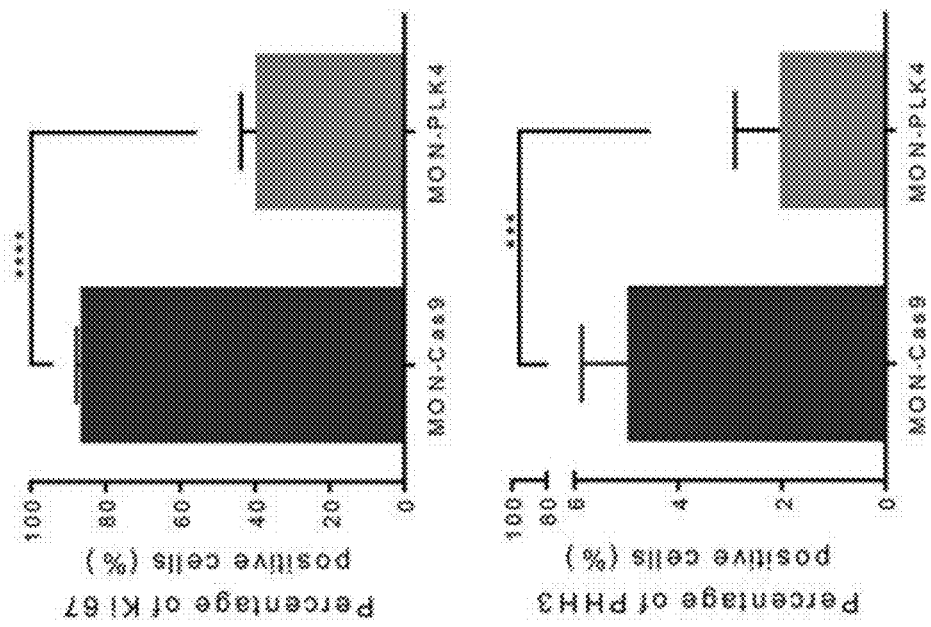

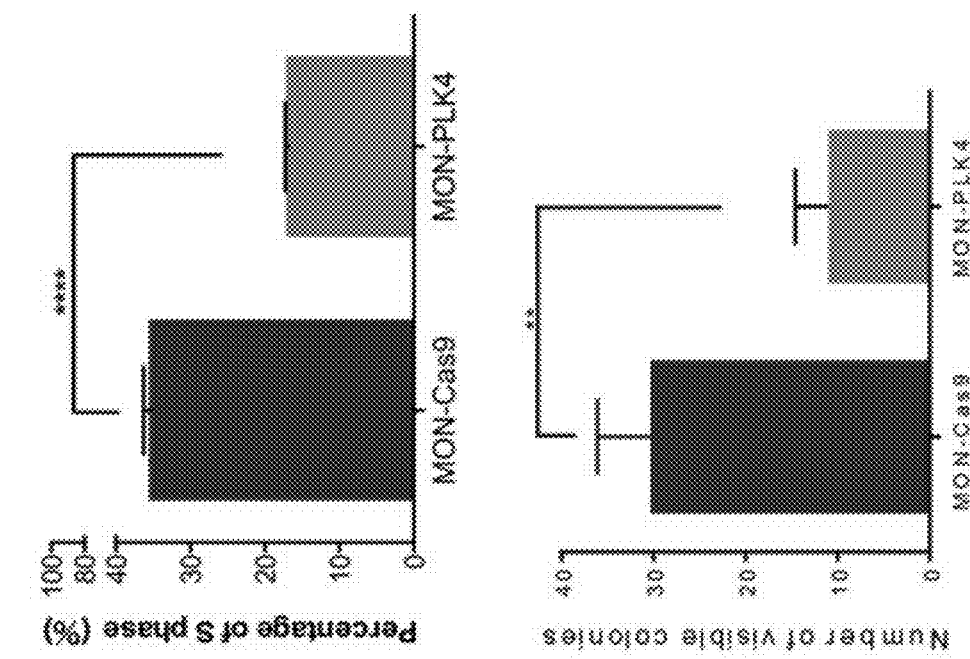
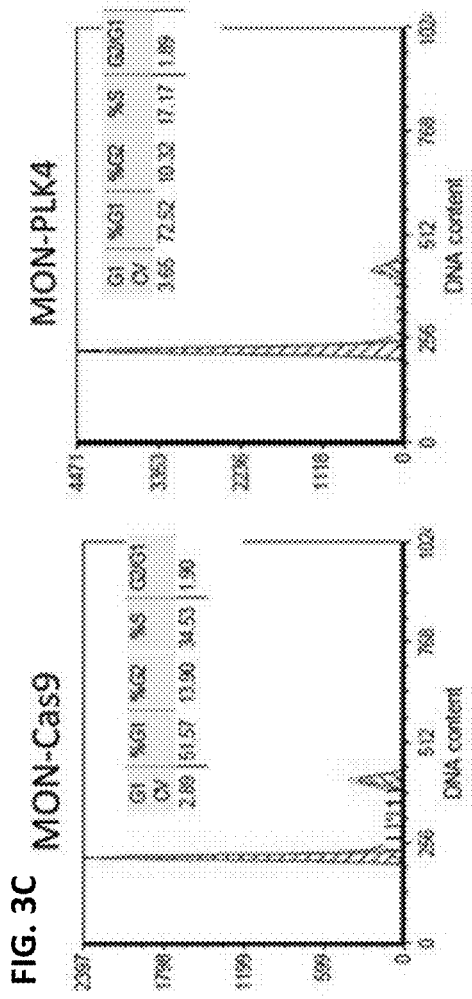
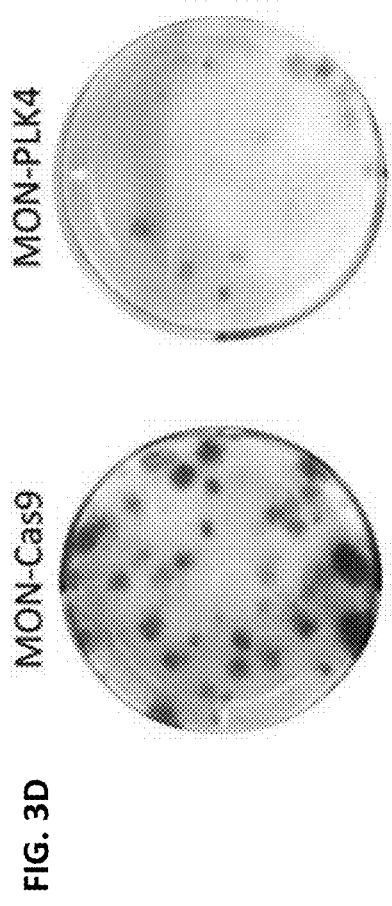
FIG. 3C
FIG. 3D

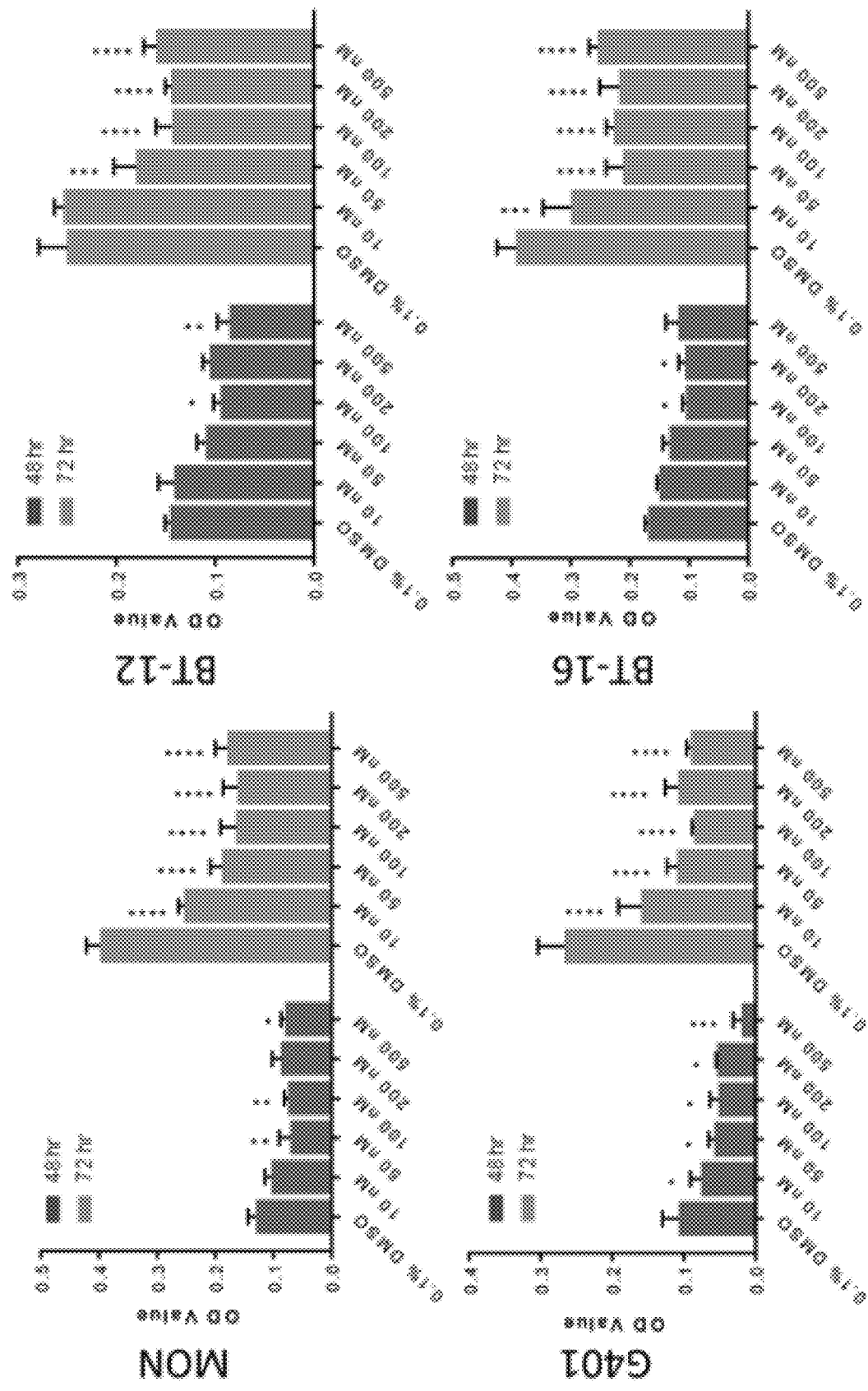

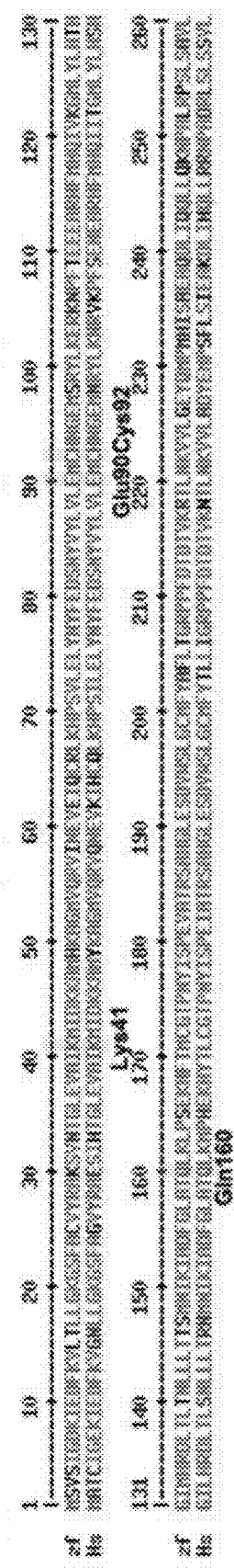
FIG. 5A  Kinase domain of human PLK4 (Hs) and the zebrafish hortologue PLK4 (zf)
FIG. 5B  Phenotype of zebrafish larvae
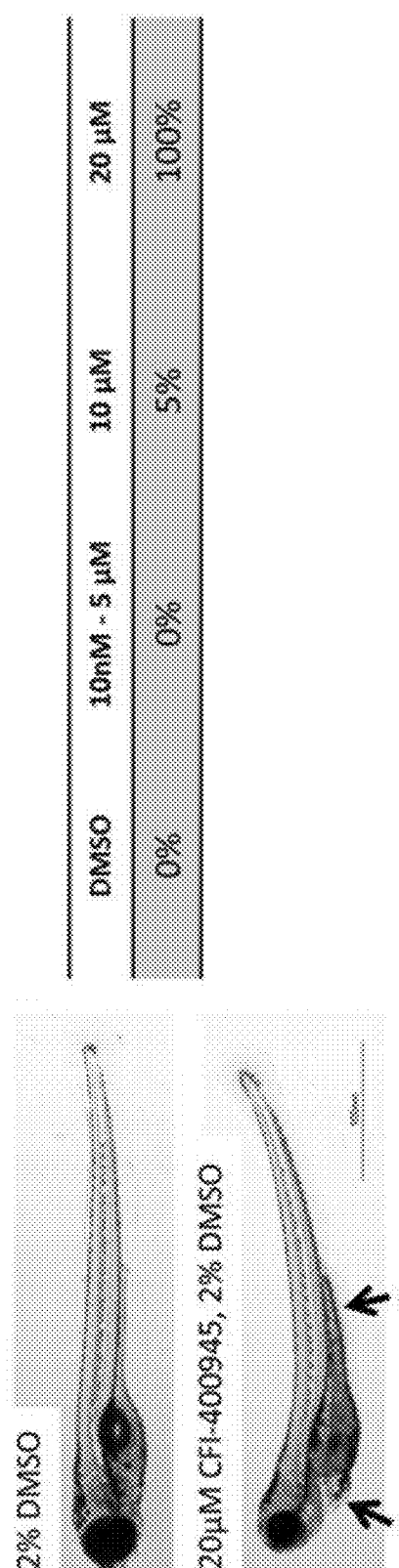
FIG. 5C  Incidence of edema at 72 hours of drug exposure
| DMSO | 10nM - 5 µM | 10 µM | 20 µM |
|---|---|---|---|
| 0% | 0% | 5% | 100% |

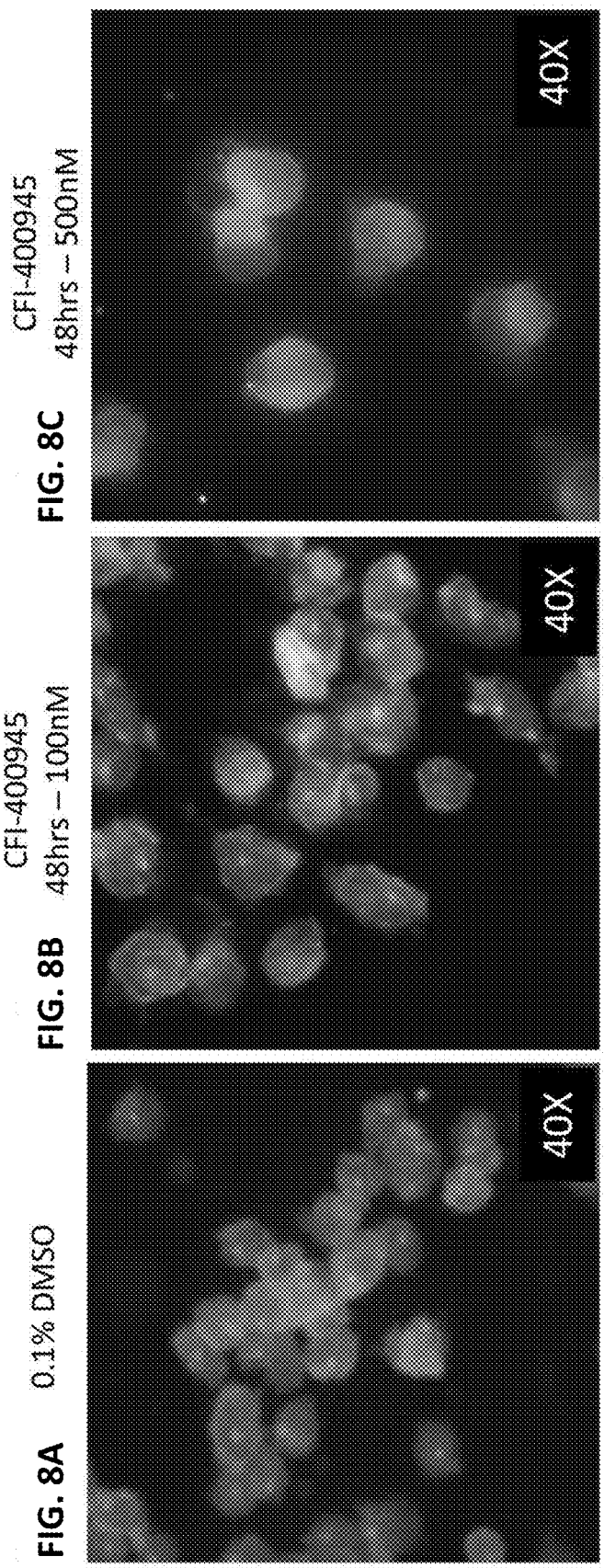

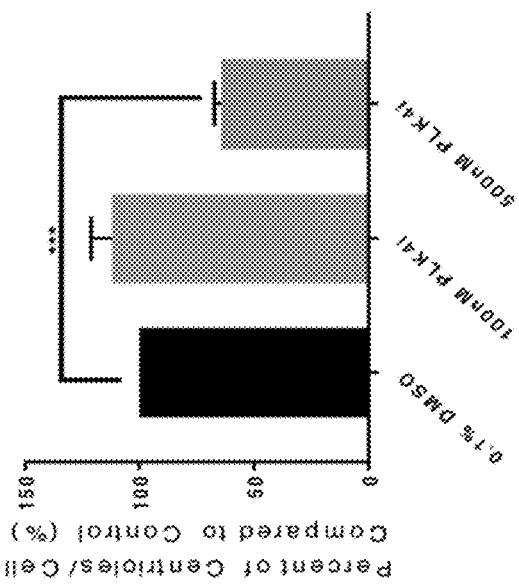
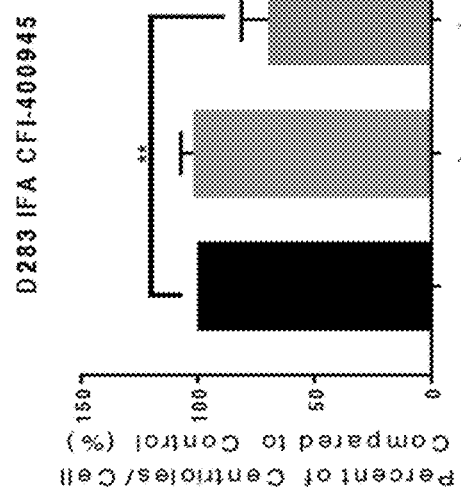
FIG. 8F (continued)

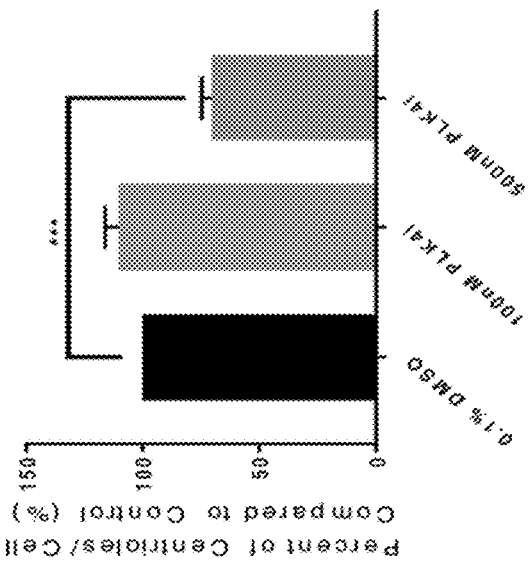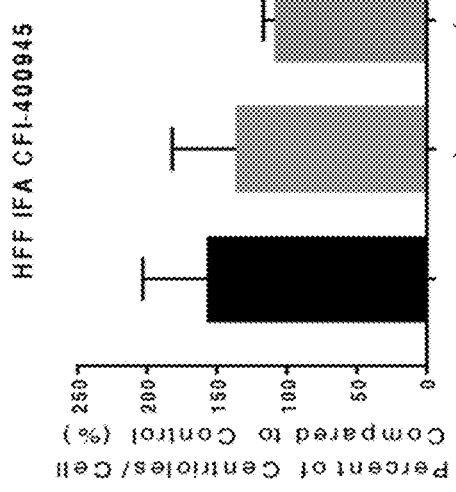
FIG. 8F (continued)

FIG. 12

| CFI-400945 Brain-to-Plasma (B:P) Ratios | | | |
|---|---|---|---|
| Time (hr) | | 4 Hour | |
| Mouse # | 355 | 356 | 357 |
| Brain Weight (g) | 0.380 | 0.440 | 0.390 |
| Brain Homogenate Volume (mL) | 1.90 | 2.20 | 1.95 |
| Brain Homogenate Conc. (ng/mL) | 9.89 | 16.6 | 6.03 |
| Brain Tissue Conc. (ng/g) | 49.5 | 83.0 | 30.2 |
| Plasma Conc. (ng/g)[1] | 498 | 967 | 697 |
| B:P Ratio | 0.0993 | 0.0858 | 0.0433 |
| Average Raw B:P Ratio | 0.0761 | ± | 0.0293 |

[1] A plasma density of 1 g/mL is assumed.

INHIBITORS OF POLO-LIKE KINASE 4 (PLK4) FOR TREATING PEDIATRIC EMBRYONAL TUMORS

CROSS-REFERENCED TO RELATED PATENT APPLICATIONS

The present application claims the benefit of priority to under 35 U.S.C. § 119(e) U.S. Provisional Application No. 62/551,526, filed on Aug. 29, 2017, the content of which is incorporated herein by reference in its entirety.

BACKGROUND

The field of the invention relates to treatment therapies for pediatric embryonal tumors. In particular, the field of the invention relates to use of inhibitors of polo-like kinase 4 (PLK4) for treating pediatric embryonal tumors including peripheral malignant rhabdoid tumors (MRT), rhabdoid tumors of the kidney (RTK), atypical teratoid/rhabdoid tumors (ATRTs) of the central nervous system (CNS), and medulloblastomas (MB).

Embryonal tumors are the most common malignant brain tumors in infants less than three years of age and otherwise may be referred to as "pediatric embryonal tumors." Two of the most common types of pediatric embryonal tumors of the central nervous system (CNS) are medulloblastomas and atypical teratoid/rhabdoid tumors (ATRTs). ATRTs are rhabdoid tumors of the CNS. Malignant rhabdoid tumors (MRT) are another type of rhabdoid tumors. Rhaboid tumors can occur in a variety of anatomical sites, including sites outside of the CNS such as in kidneys as rhabdoid tumors of the kidney (RTK). Pediatric embryonal tumors are highly aggressive and therapy-resistant.

In an effort to identify therapeutic targets for pediatric embryonal tumors, we screened for kinases that would impair tumor cell proliferation by using a CRISPR/Cas9 mutagenesis system. We discovered that mutations in the polo-like kinase 4 (PLK4) gene resulted in significant impairment of cell proliferation, survival, invasion and migration of pediatric embryonal tumor cells. Through high throughput genome-wide data we were able to verify the upregulation of PLK4 in MRT, RTK, AT/RTs and in other embryonal tumors of the brain, including MB.

Initial evidence of PLK4 as a druggable target for cancer was shown in a phase 1 clinical trial of adults having advanced solid tumors by treatment with the experimental therapeutic CFI-4000945, a PLK4 inhibitor. (See Clinical-Trials.gov identifier (NCT number: NCT01954316)). Our results here provide the first evidence that a PLK4 inhibitor might be a potential treatment for pediatric embryonal tumors. Our findings also demonstrate that CFI-4000945 does not affect non-tumor cells. Targeting PLK4 with CFI-400945 represents a novel strategy to treat not only ATRTs but also other embryonal tumors of the brain, including medulloblastomas, more effectively and with less toxicity/side effects. (See Sredni et al., "A functional screening of the kinome identifies the Polo-like kinase 4 as a potential therapeutic target for malignant rhabdoid tumors, and possibly, other embryonal tumors of the brain," Pediatr. Blood Cancer. 2017. doi: 10.1002/pbc.26551; and Sredni & Tomita., "The polo-like kinase 4 gene (PLK4) is overexpressed in pediatric medulloblastoma," Childs Nery Syst. 2017. doi: 10.1007/s00381-017-3452-8.F; the contents of which are incorporated herein by reference in their entireties).

SUMMARY

Disclosed are methods and compositions for treating pediatric embryonal tumors. The methods and compositions utilize or include an inhibitor of polo-like kinase 4 (PLK4) for treating pediatric embryonal tumors.

The disclosed methods include treatment methods in which a subject having a pediatric embryonal tumor is administered a pharmaceutical composition comprising an inhibitor of PLK4 and a suitable pharmaceutical carrier, diluent, or excipient. Pediatric embryonal tumors that may be treated in the disclosed treatment methods may include, but are not limited to malignant rhabdoid tumors (MRT), rhabdoid tumors of the kidney (RTK), atypical teratoid/rhabdoid tumors (ATRTs) of the central nervous system (CNS), and medulloblastomas (MB).

Suitable inhibitors of PLK4 may include so-called "spiro cyclo-propyl indolinone compounds." In particular, suitable inhibitors of PLK4 may include (1R,2S)-(E)-2-(3-(4-trans-2,6-dimethylmorpholino)methyl) styryl)-1H-indazol-6-yl)-5'-methoxyspiro[cyclopropane-1,3'-indolin]-2' one, which otherwise is referred to as "CFI-400945." In some embodiments of the disclosed methods, the inhibitor of PLK4 is administered orally or systemically (e.g., intravenously).

In the disclosed treatment methods, the subject may be administered combination therapy where an additional therapy is administered to the subject in addition to administering the inhibitor of PLK4 to the subject. In particular, the subject may be administered a chemotherapeutic agent and/or or radiation therapy in addition to the inhibitor of PLK4, where the chemotherapeutic agent and/or or radiation therapy are administered to the subject before, concurrently with, or after the PLK4 inhibitor is administered to the subject, and in some embodiments after the PLK4 inhibitor is administered to the subject.

BRIEF DESCRIPTION OF THE FIGURES

(FIG. 1A) Representative image of MON cells after transduction with negative control. Right: bright field; Left: fluorescence microscope. We observed high transduction efficiency with 95% of the cells expressing GFP after transduction with the virus (2.5 MOI). (FIG. 1B) As the earliest measure of cell proliferation, after transduction and selection, cells were transferred in equal numbers to 12-well plates and time to reach confluence was determined. The controls reached confluence in 7 days. We selected as top slowest proliferating cells after gene editing, cells that took at least 14 days to reach confluence. Among them, PLK4 took the longest (22 days). (FIG. 1C) Target sites for the four PLK4 gRNAs (PLK4.1, PLK4.2, PLK4.3, and PLK4.4). Gene editing was validated by GCD (lower panel) and NGS (data not shown). (FIG. 1D) qRT-PCR showed 34% reduction of PLK4 expression in MON-PLK4-mutated cells FIG. 2A, FIG. 2B, FIG. 2C and FIG. 2D. Microarray GE profiling of PLK4 of 111 pediatric brain tumor samples and five normal brain tissue samples.

Figure 1A:
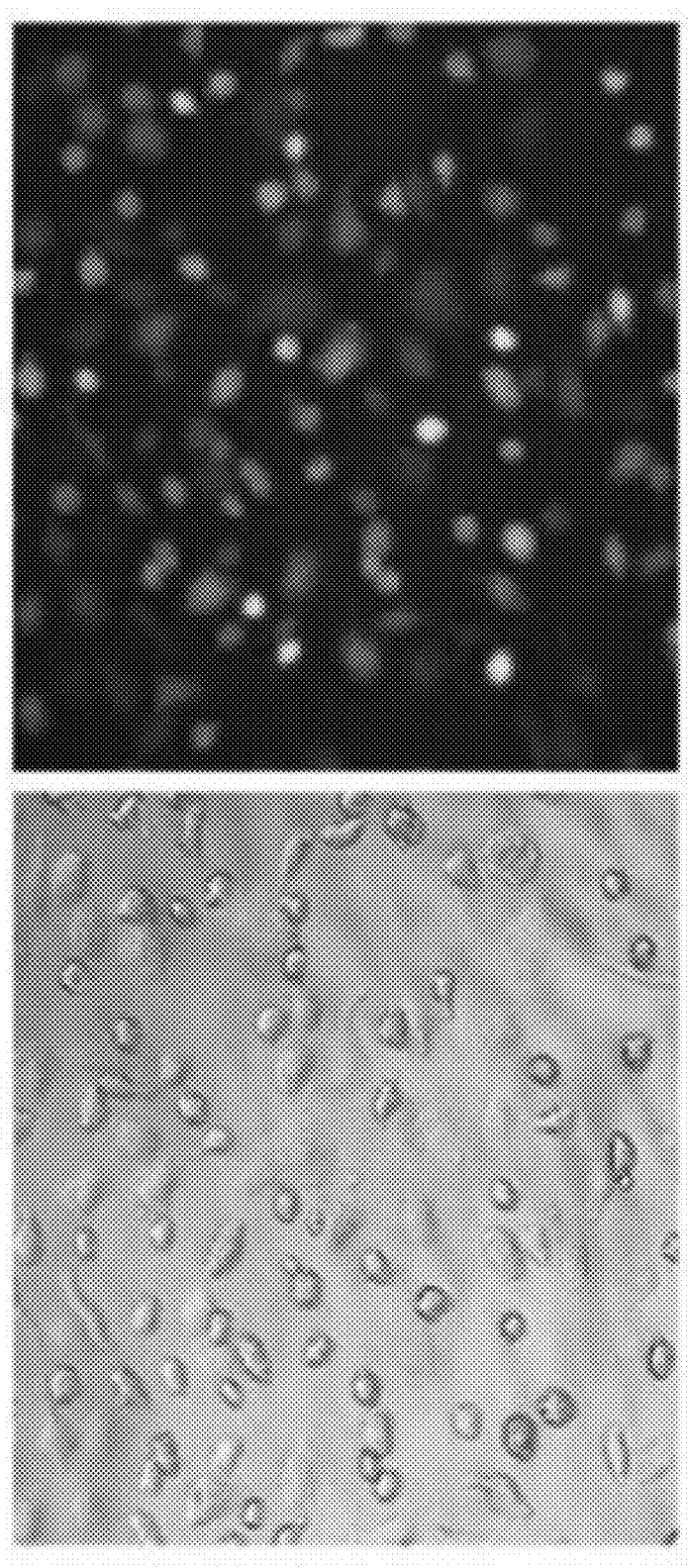
FIG. 1A, FIG. 1B, FIG. 1C, and FIG. 1D. Gene editing of MON cells using lentiviral CRISPR/Cas9.
Figure 1B:
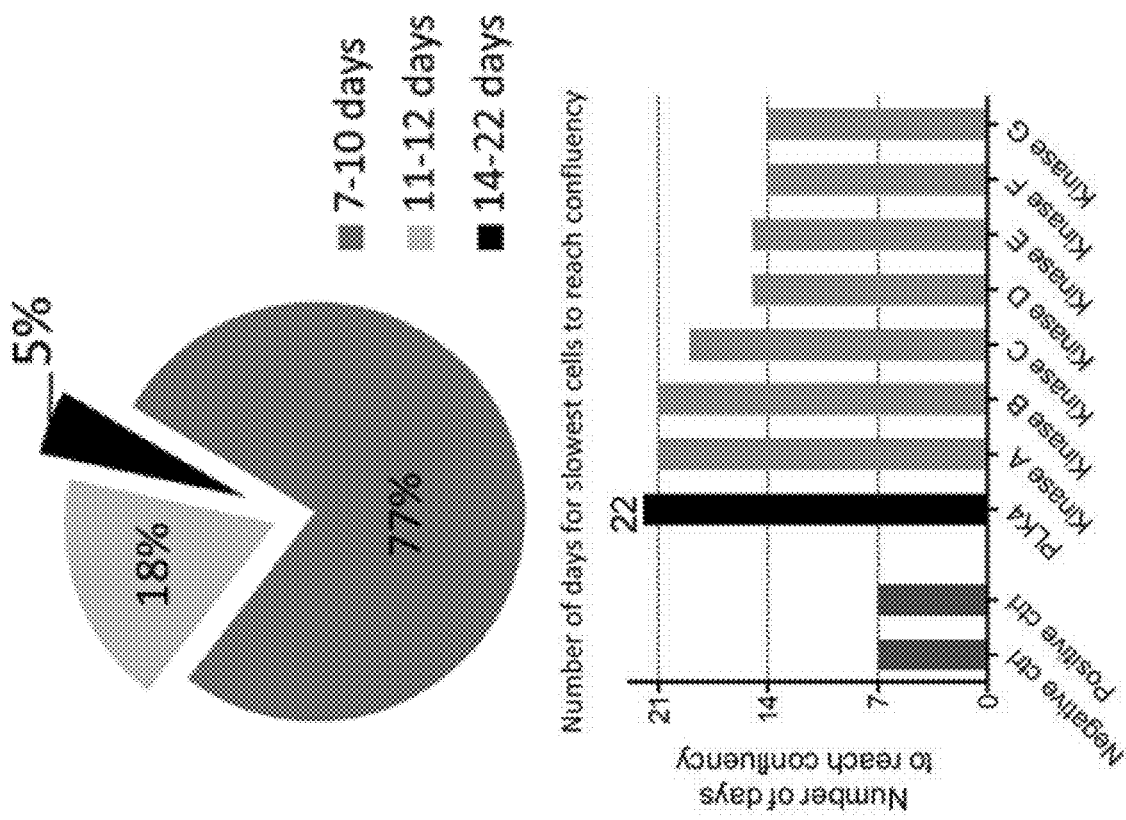

****P<0.0001, one-way ANOVA, data not shown) as previously described in the literature. These data can be used as references for the PLK4 expression levels observed in our cohort of samples.

FIG. 3A, FIG. 3B, and FIG. 3D. Characterization of MON-PLK4-mutated cells. (FIG. 3A) Representative image of MC for Ki-67 (1:200, Thermo Scientific, USA). (FIG. 3B) Representative image of IHC for PHH3 (1:5,000, Abcam, USA). The percentage of cell expressing these markers was significantly lower in MON-PLK4-mutated cells than in MON-Cas9 cells (*P<0.001 and P<0.0001, unpaired t-test). In both: 40× magnification and 50 µm scale bars. (FIG. 3C) Cell cycle analysis by flow cytometry showed significant decrease in cells in S phase in MON-PLK4-mutated cells when compared to the control MON-Cas9 ( P<0.0001, unpaired t-test). (FIG. 3D) Clonogenic assay showed a significantly smaller number of colonies in MON-PLK4-mutated cells when compared to MON-Cas9 cells (P<0.01, unpaired t-test)

FIG. 4A, FIG. 4B, FIG. 4C, FIG. 4D, and FIG. 4E. Cytotoxic effects of CFI-400945 in vitro. (FIG. 4A) Treatment with CFI-400945 resulted in significant reduction of cell proliferation in all cell lines evaluated as assessed by MTT assay (*P<0.05, P<0.01, *P<0.001, and **P<0.0001, two-way ANOVA). (FIG. 4B) Clonogenig assay analyzed 14 days after treatment with CFI-400945 showed complete absence of colonies when cells were exposed to the drug at concentrations of 50-200 nM ( P<0.0001, two-way ANOVA). Left: representative images of colonies treated with DMSO; Right: representative images of colonies treated with 50 nM of CFI-400945. (FIG. 4C) qRT-PCR showed that HFF-SCC058 human fibroblasts had significantly lower PLK4 expression when compared with MON cells (**P<0.0001, unpaired t-test). (FIG. 4D) and (FIG. 4E) Invasion and migration assays showed significant reduction in MON cells after 24 hr of treatment with 100 nM of the drug, while no effects were observed in HFF-SCC058 human fibroblasts (*P<0.05 and ***P<0.001, two-way ANOVA)

FIG. 5A, FIG. 5B and FIG. 5C. Cytotoxic effects of CFI-400945 in vivo. (FIG. 5A) Comparison of the N-terminal fragment, corresponding to the kinase domain, of human PLK4 (Hs) and the zebrafish ortholog Plk4 (zf). The protein sequences are highly conserved (red: identical amino acids; blue: conserved amino acids), including identical bases involved in CFI-400945 binding sites (highlighted in green). (FIG. 5B) Representative phenotype of a normal zebrafish larva (top) and a zebrafish larva treated with 20 µM of CFI-400945 that developed pericardial and pronephric duct edema (arrows). (FIG. 5C) Data on the table corresponds to treatment of zebrafish larvae with different concentrations of CFI-400945 at 72 hr.

FIG. 6A, FIG. 6B, FIG. 6C, and FIG. 6D. PLK4 is overexpressed in MB and CFI-400945 significantly affected. MB cell lines. (FIG. 6A) MTT proliferation assays—CFI-400945 significantly decreased proliferation in both cell lines compared to the control (0.1% DMSO) after 72 hours of treatment. (FIG. 6B) Complete inhibition of colony formation was observed at a concentration of 50 nM of the PLK4i in DAOY and D283 respectively. (FIG. 6C) qRT-PCR showed significantly higher expression of PLK4 in DAOY and D283 when compared to HFF-SCC058 human fibroblasts. (FIG. 6D) and (FIG. 6E) Cell migration and invasion were assessed after 24 hour treatment with 100 nM PLK4i. Both the DAOY and D283 treated cell lines exhibited significant decrease in cell migration and invasion compared to control (0.1% DMSO).

FIG. 7A, FIG. 7B, FIG. 7C, FIG. 7D, and FIG. 7E. CFI-400945 affected tumor cell ability to reach confluency and had an impact on cell viability. Significant delay in reaching confluency was observed when MON, G401, BT-12 and DAOY cells were treated with increasing concentrations of CFI-400945 starting at 31_25111\4. Cells were plated at a density, of 6,000 cells/well. (FIG. 7A) MON MRT cells (FC=1.56, p-value=0.004); (FIG. 7B) G401 RTK cells (FC=1.78, p-value=0.004); (FIG. 7C) BT-12 AT/RT cells (FC=1.89, p-value=0.001) and (FIG. 7D) DAOY MB cells (FC=1.70, p-value=0.029); (FIG. 7E) Dose-response curves created from viability assays for three rhabdoid cell lines and one MB cell line treated with concentrations of CFI-400945 ranging from 1 nM to 10 µM. IC50 values were calculated: MON (5.13 µM), BT-12 (3.73 µM), G401 (3.79 µM), DAOY (0.094 µM).

Figure 6A:
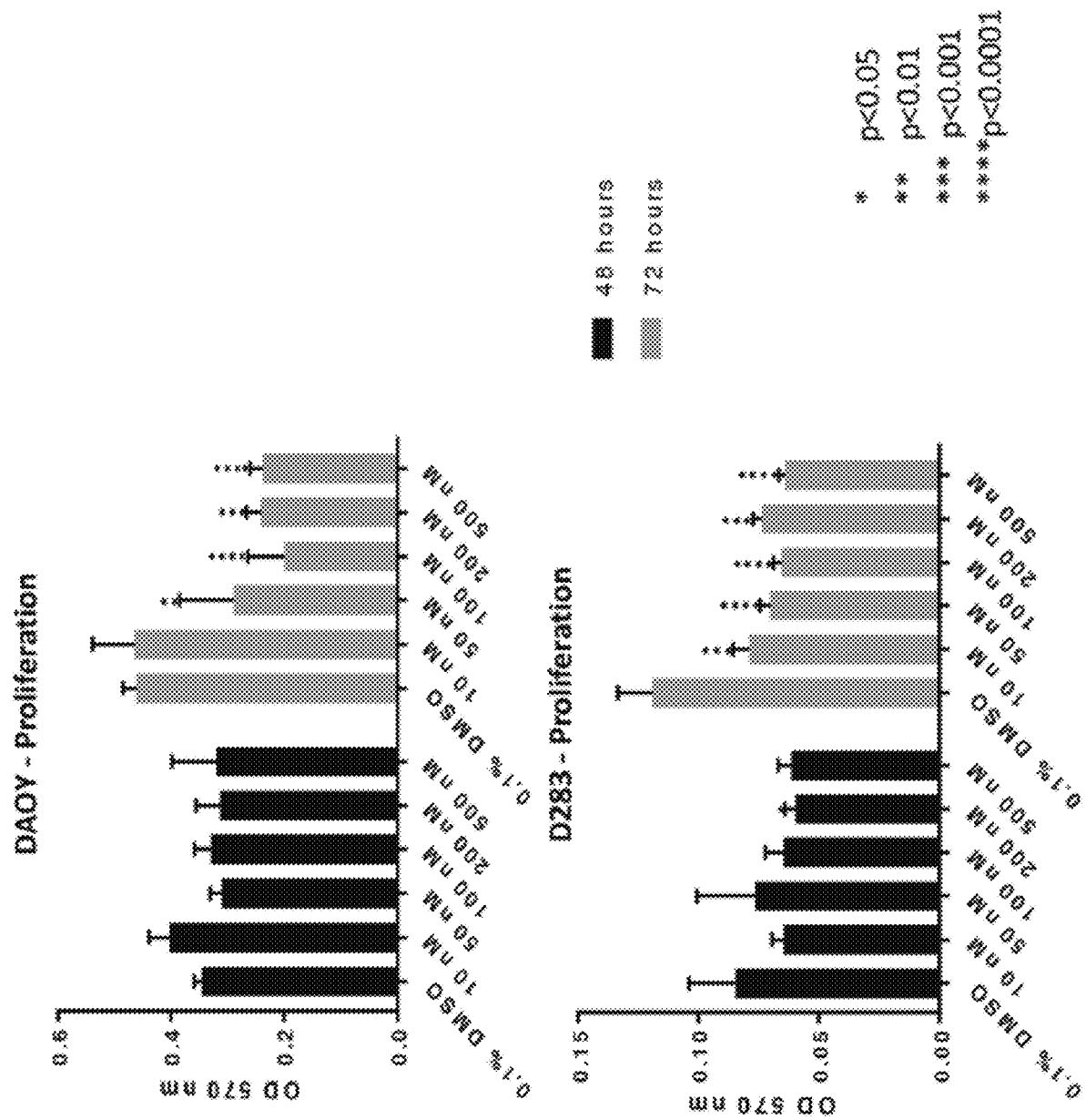
Figure 6B:
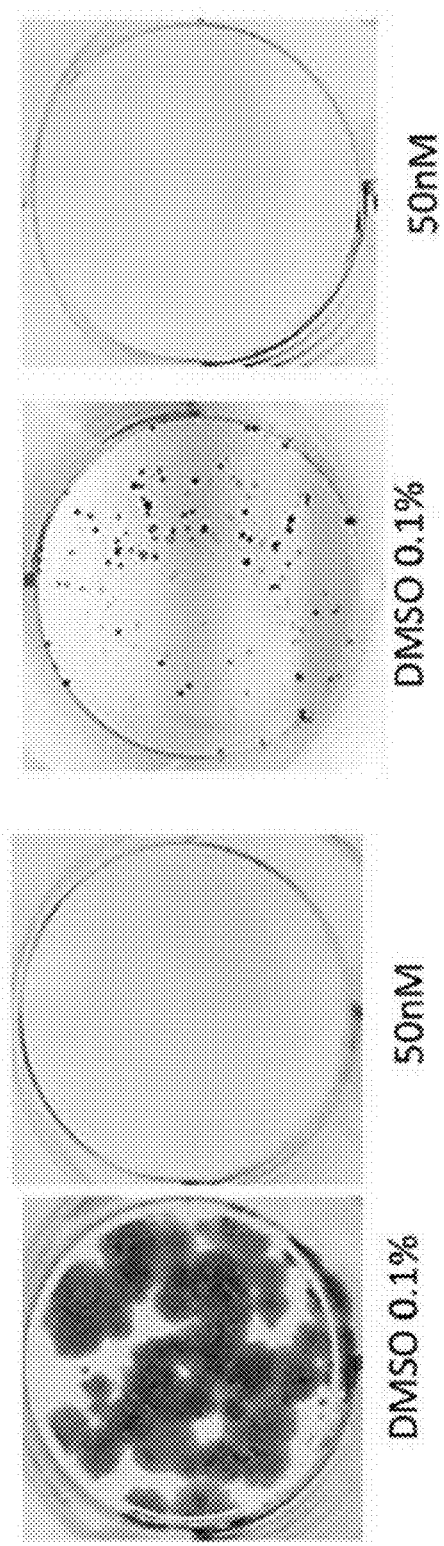
Figure 6C:
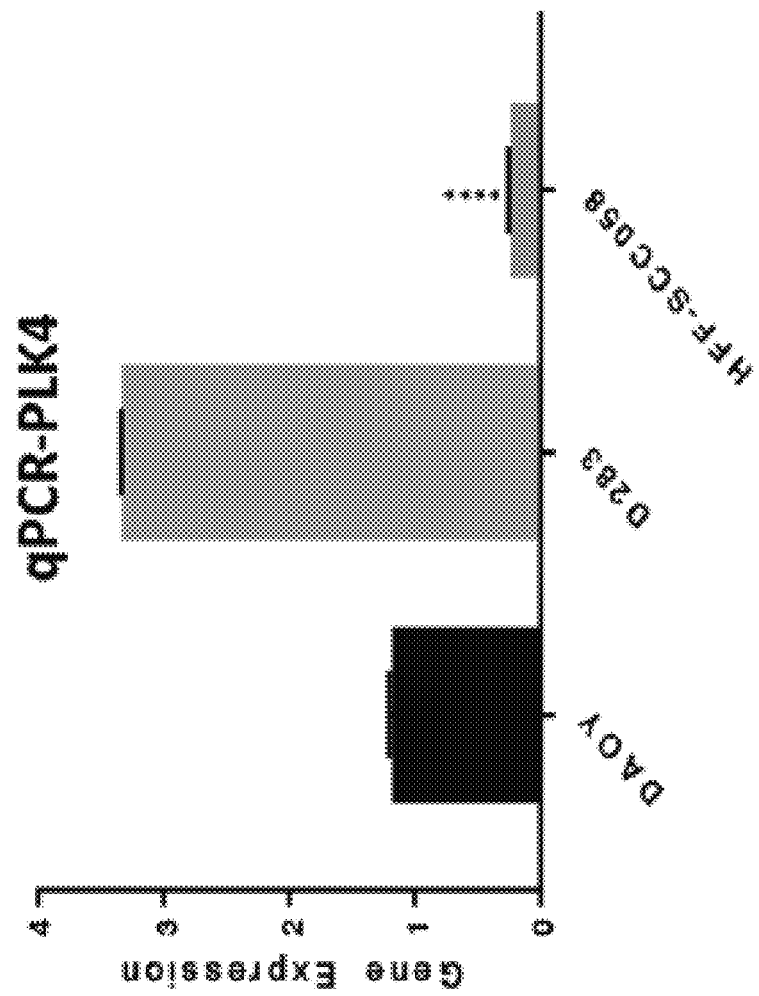
Figure 6D:
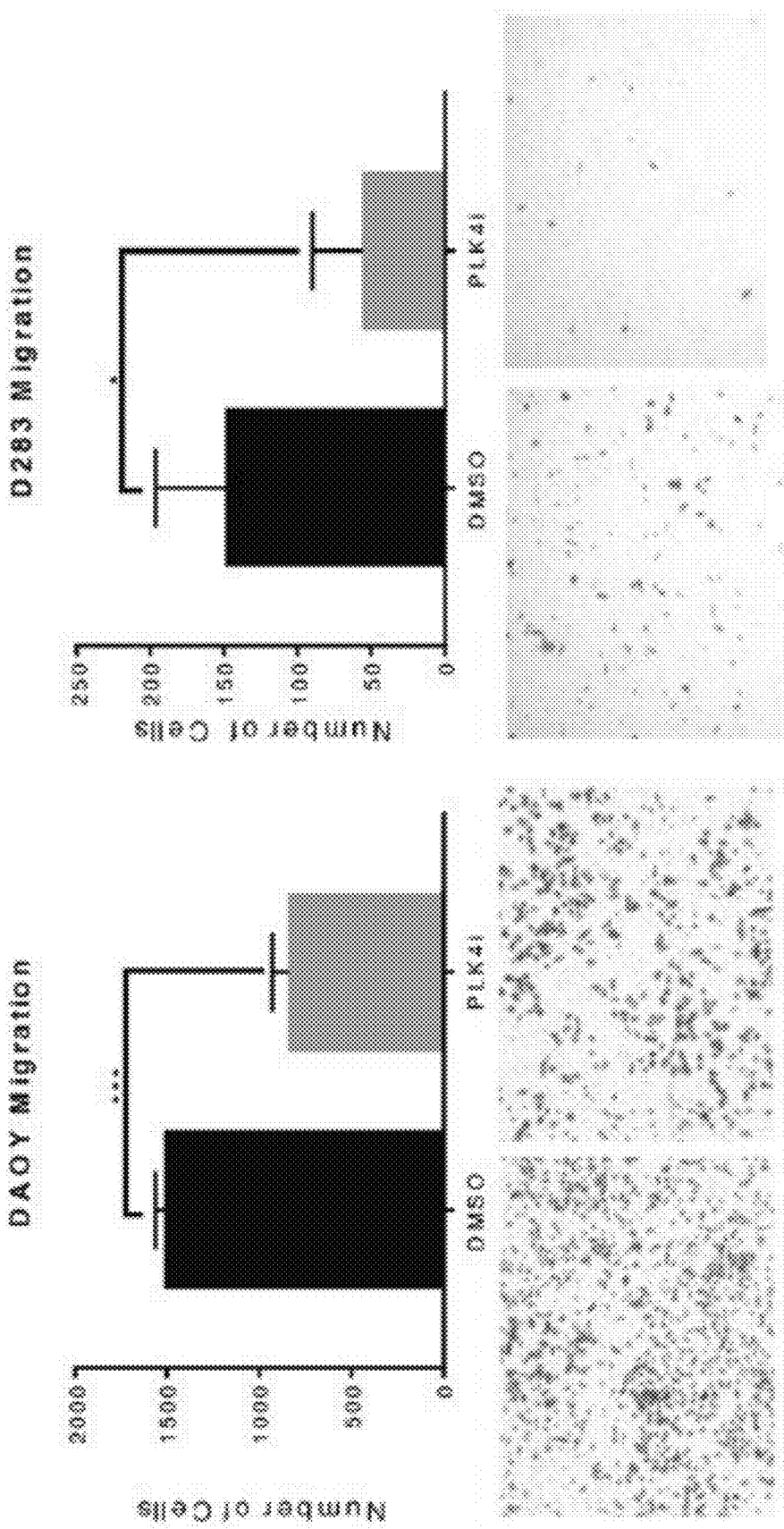
Figure 6D:
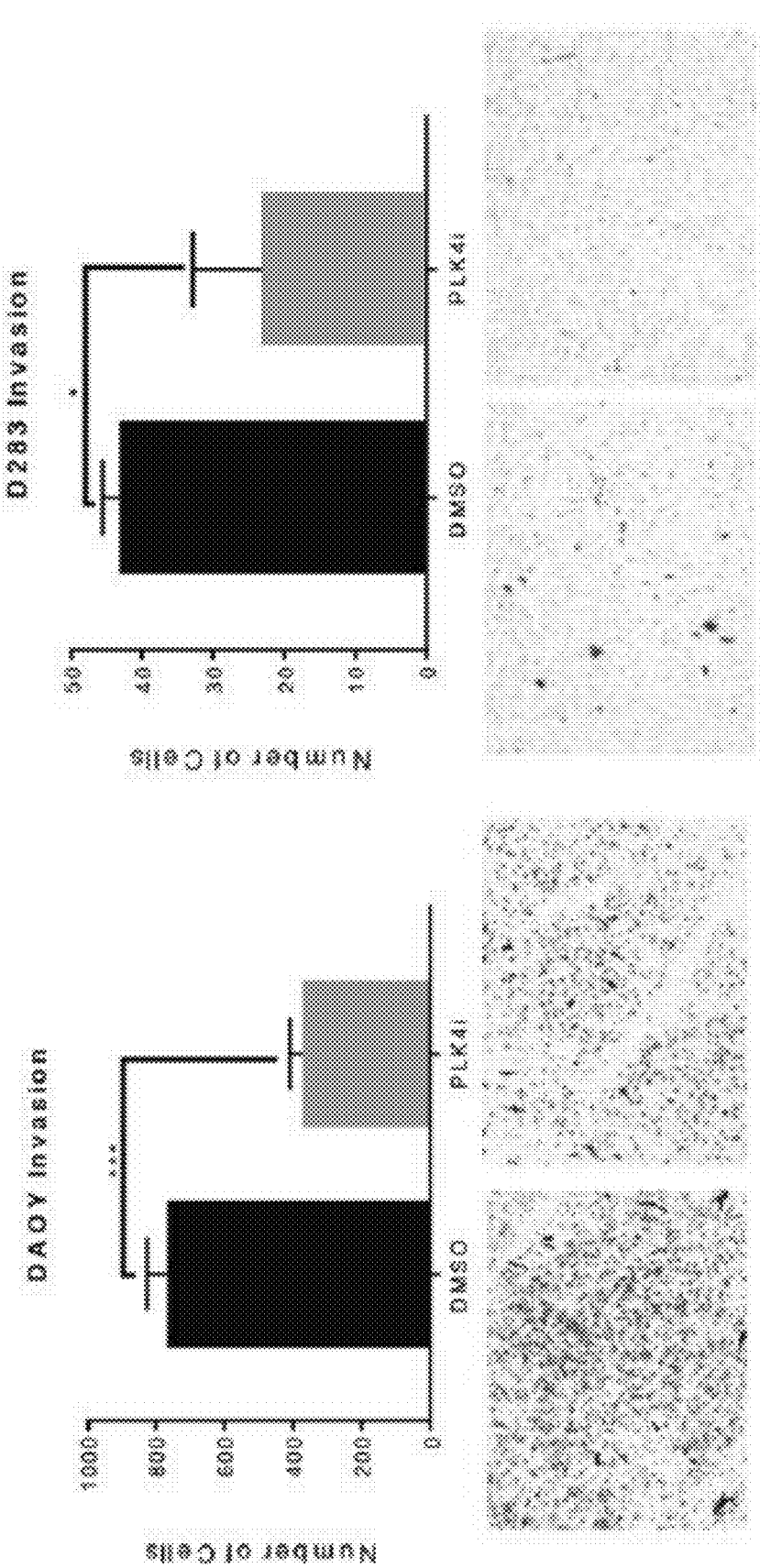
Figure 7A:
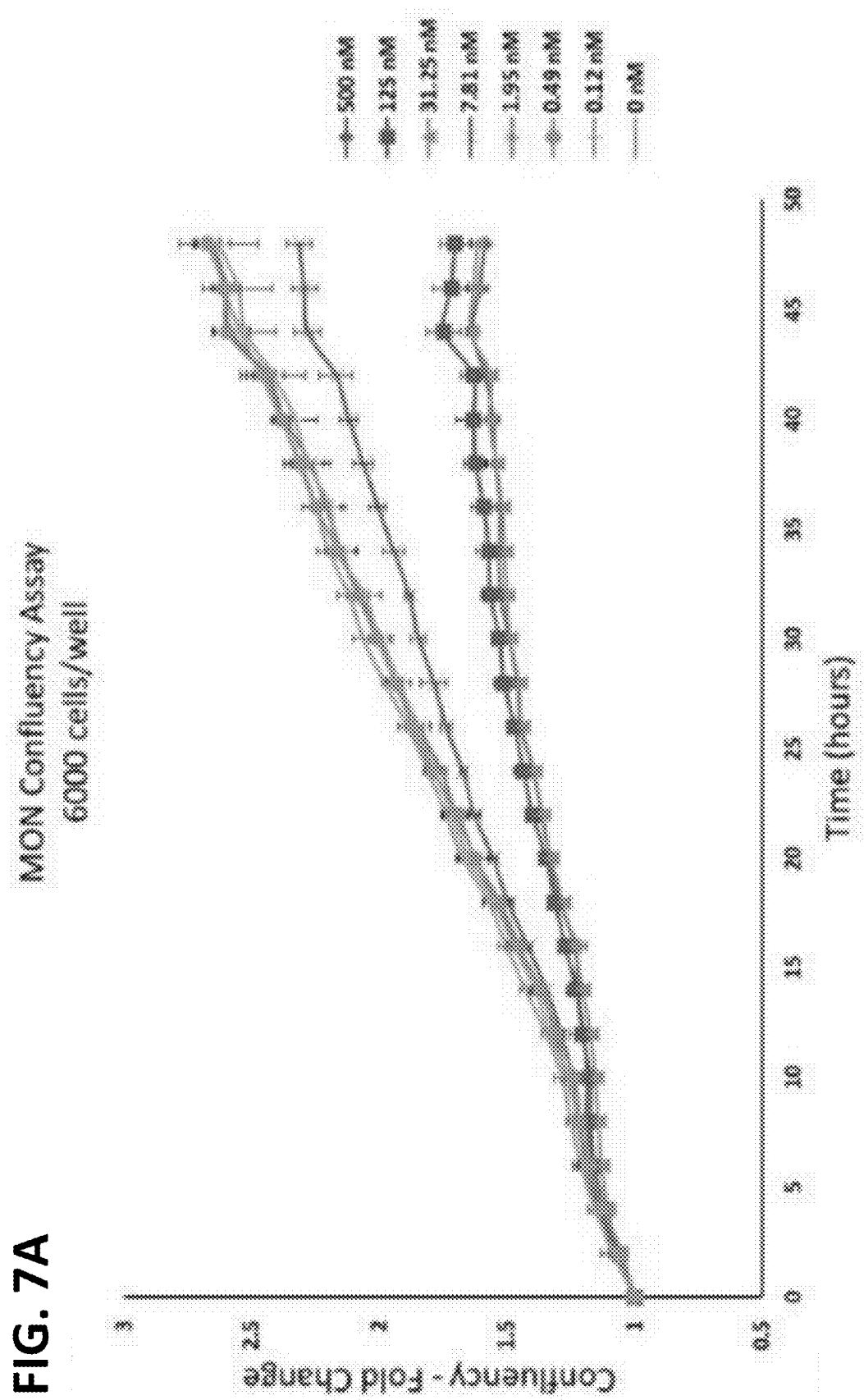
Figure 7B:
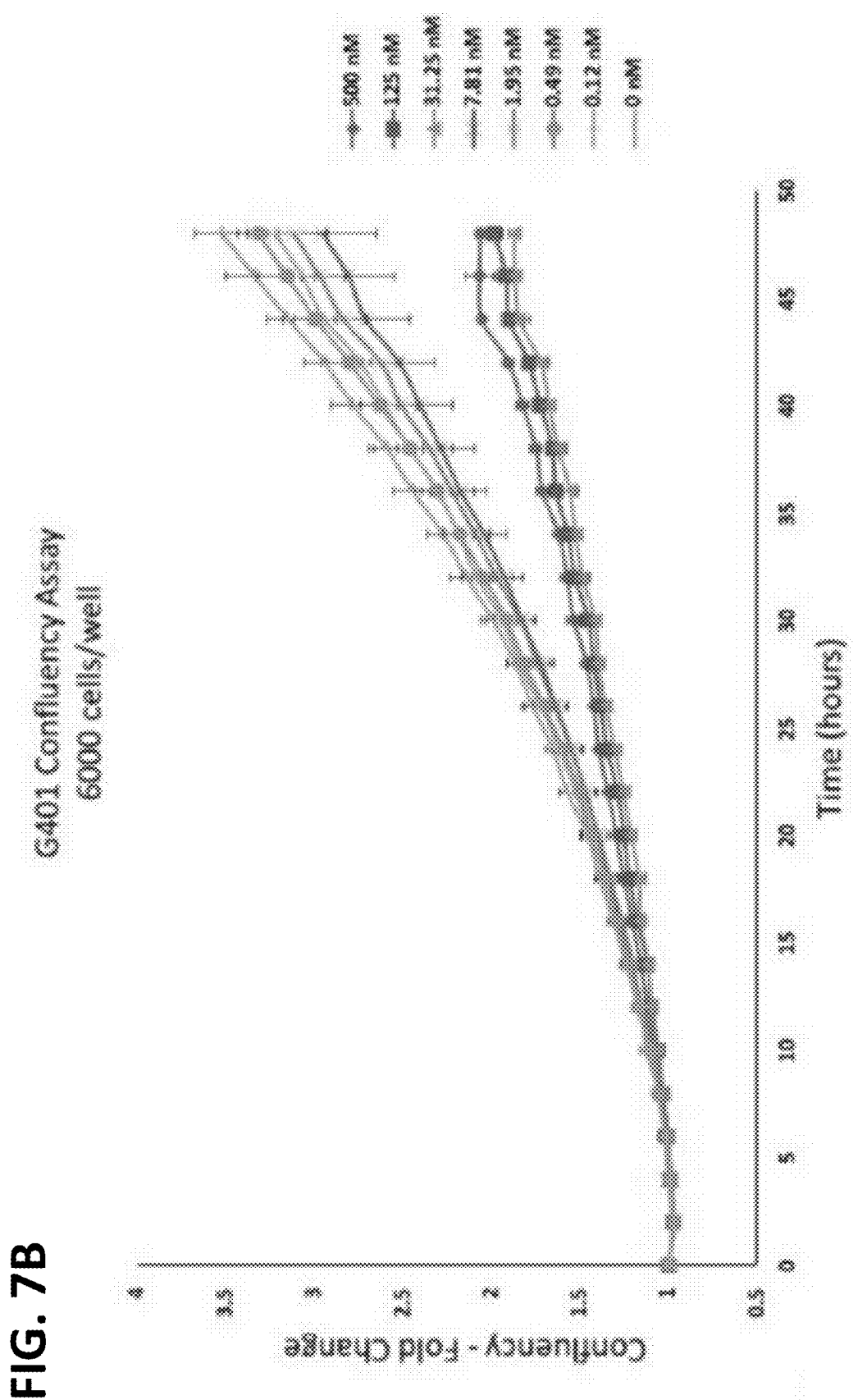
Figure 7C:
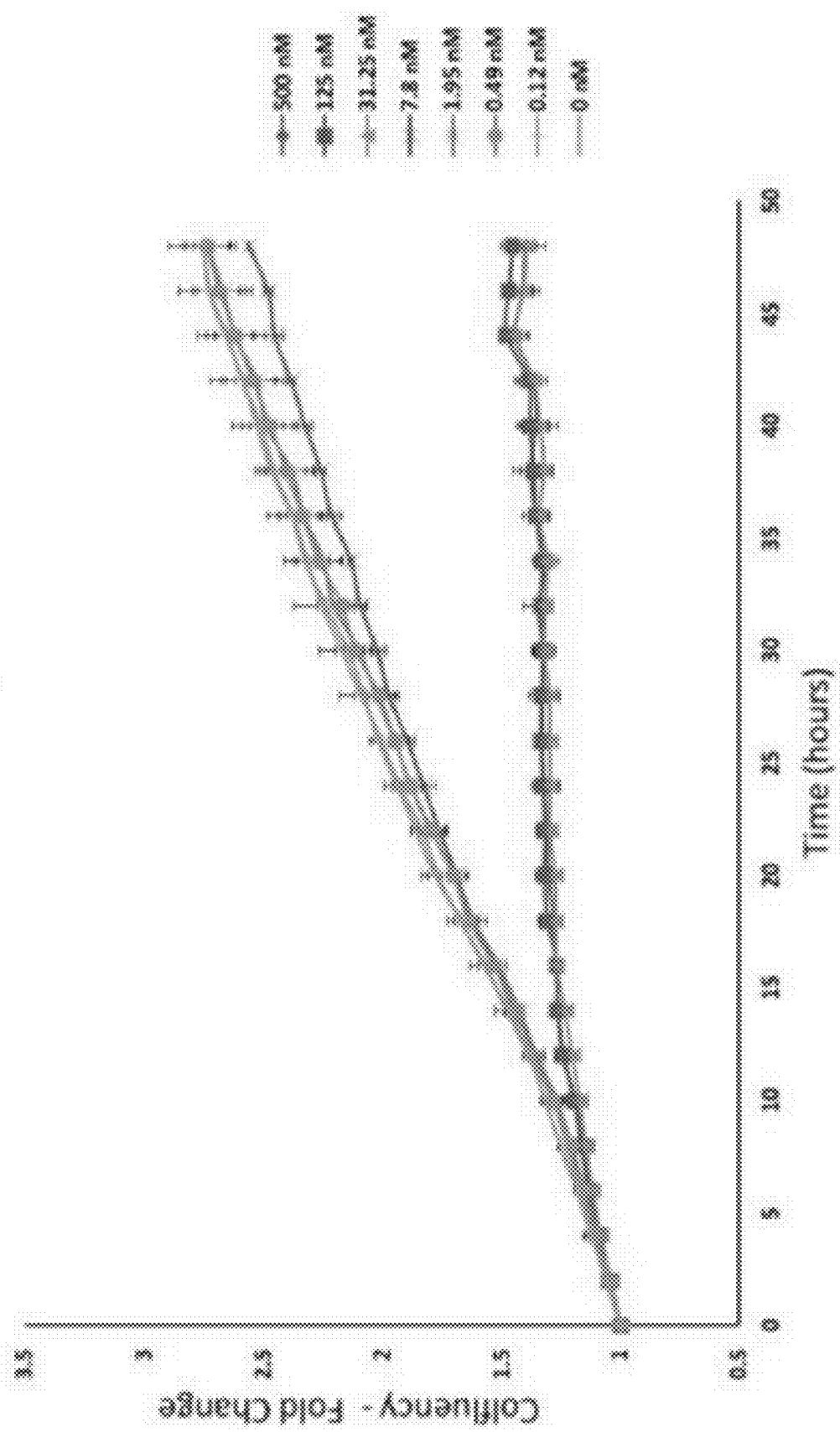
Figure 7D:
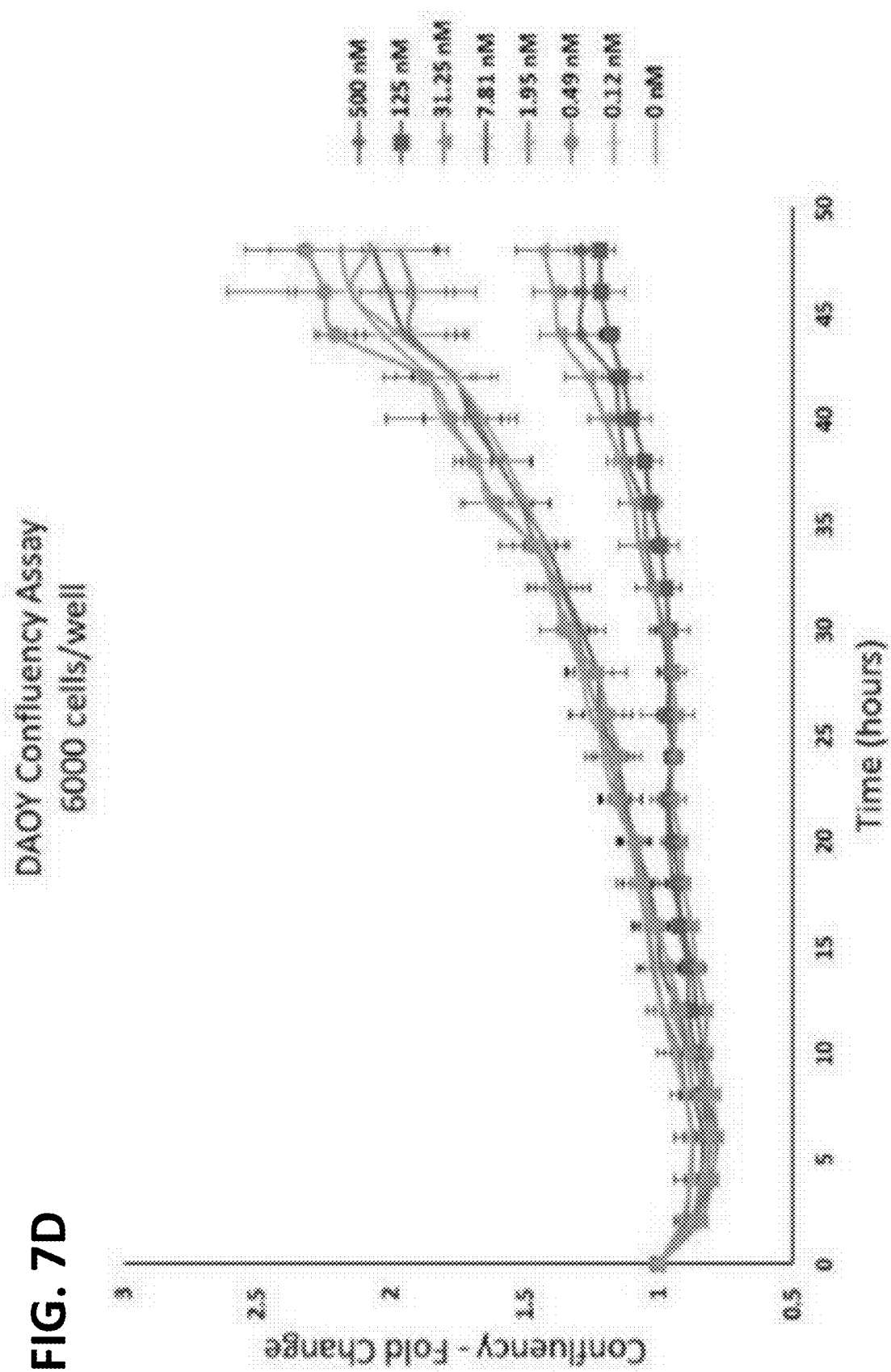
Figure 7E:
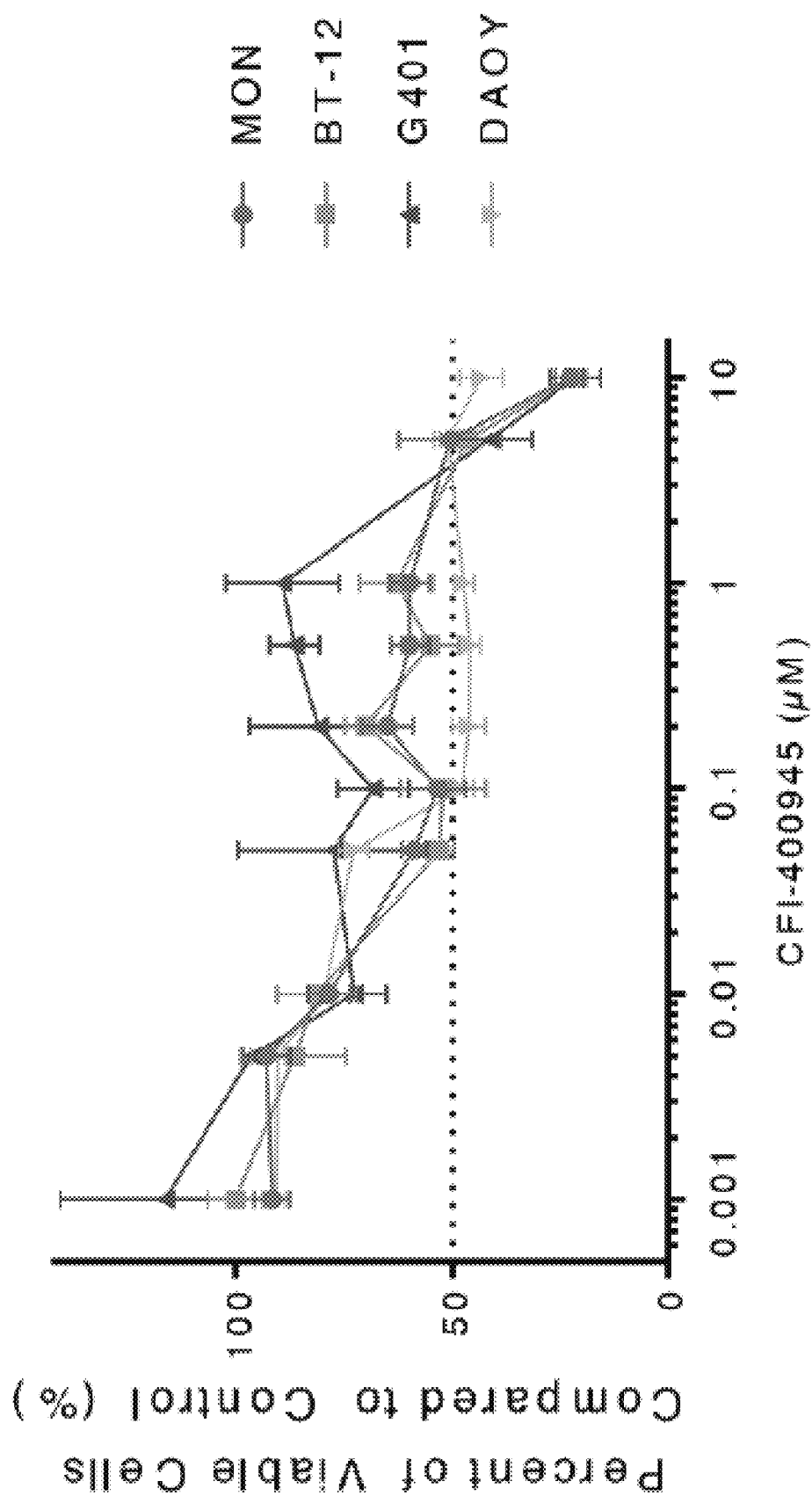
Figure 8D:
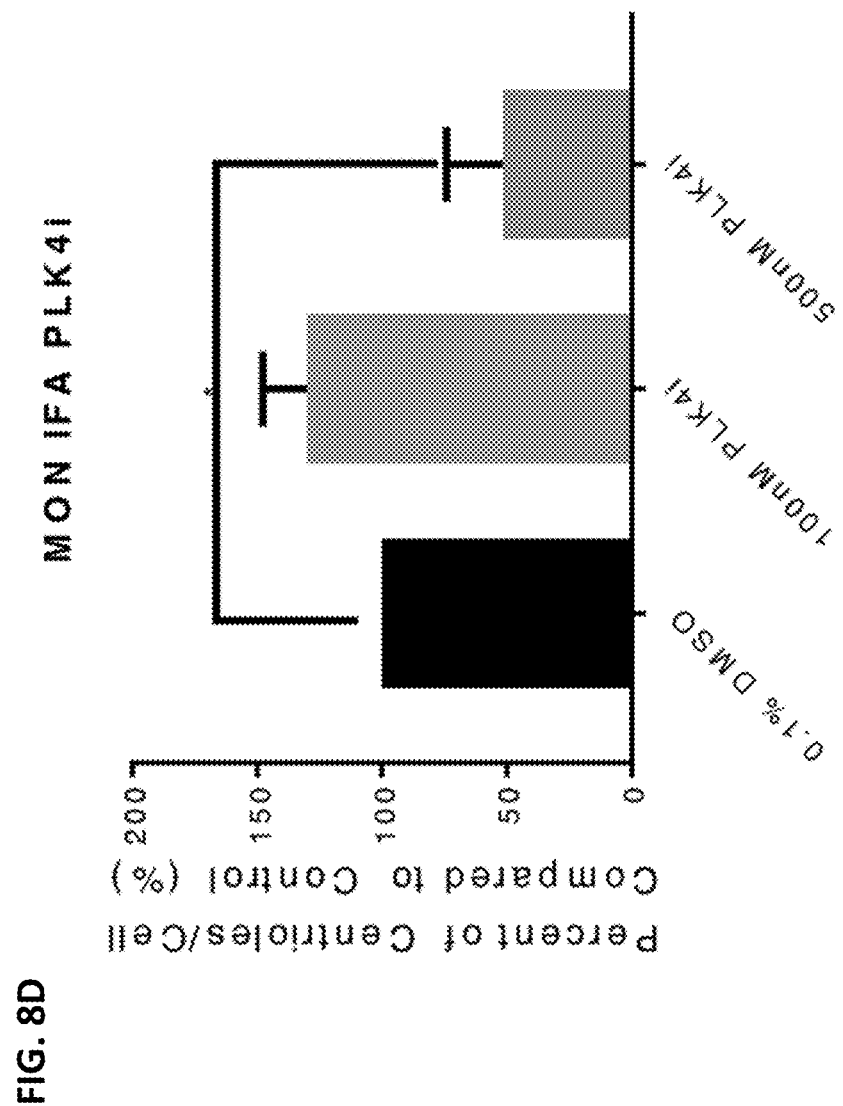
Figure 8E:
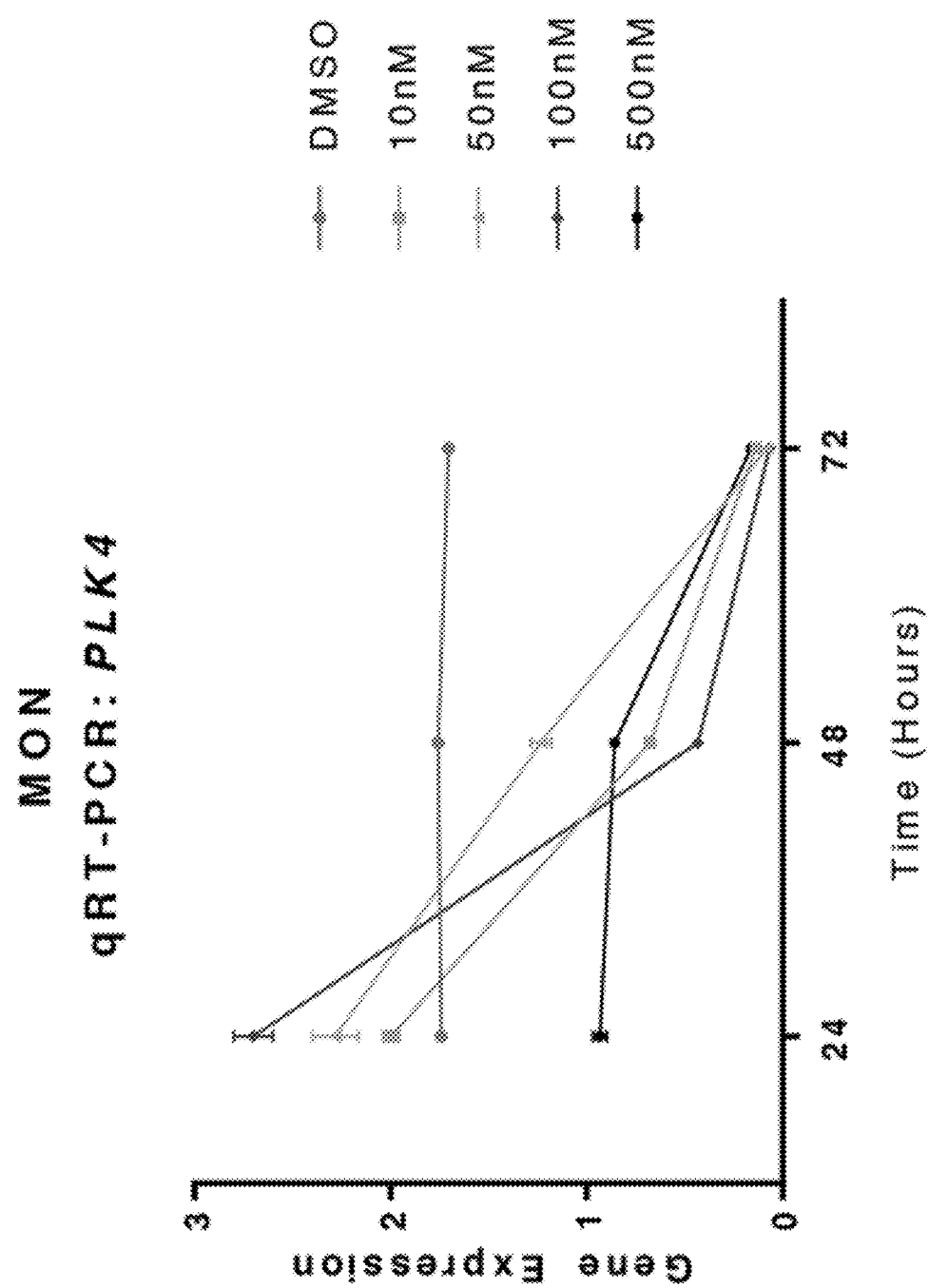
Figure 8F:
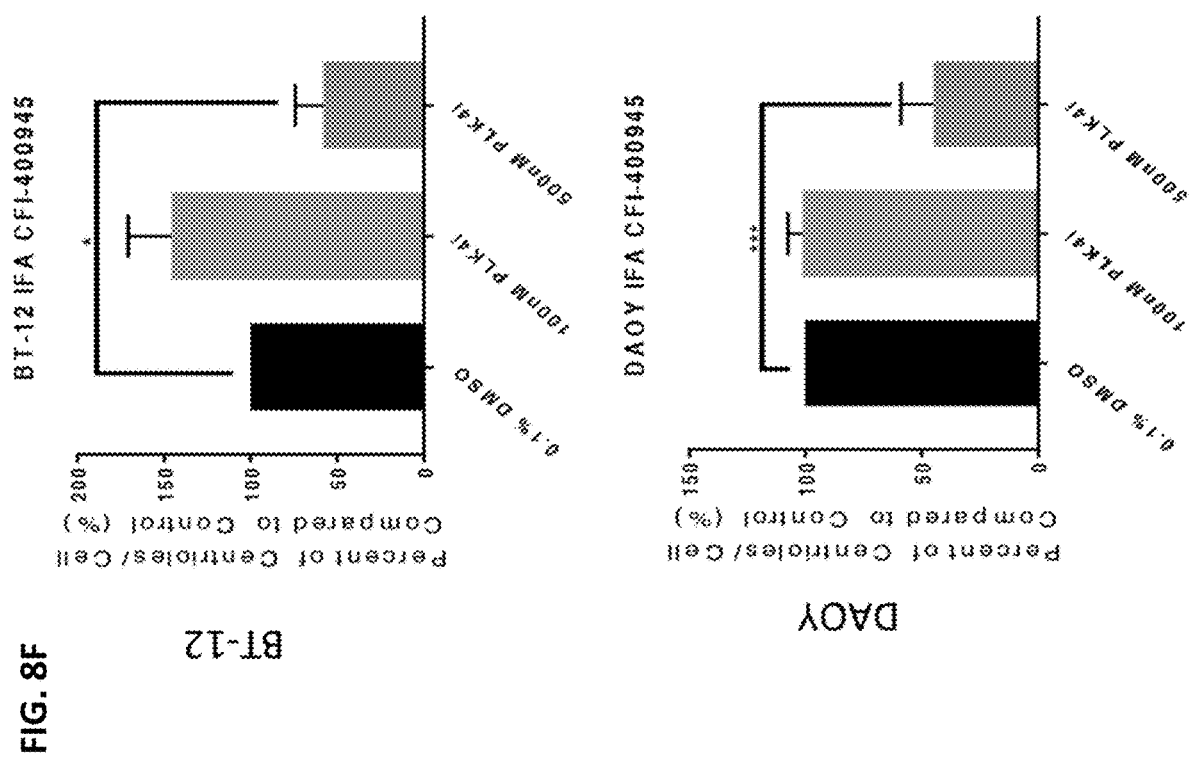

FIG. 8A, FIG. 8B, FIG. 8C, FIG. 8D, FIG. 8E and FIG. 8F. The PLK4 inhibitor CFI-400945 affected centriole duplication and PLK4 inRNA expression. Immunofluorescence (IFA) for gamma-tubulin of MON rhabdoid cells treated with CFI-400945 for 48 hours (blue—nuclei, bright green—centriole). (FIG. 8A) Control—Cells treated with 0.1% DMSO. (FIG. 8B) When treated with 100 nM there was a slight increase in centrioles' number. (FIG. 8C) When treated with 500 nM there was significant depletion of centrioles. (FIG. 8D) The ratio of number of centrioles/cell illustrates the "paradoxical effect". (FIG. 8E) qPCR for PLK4 in MON rhabdoid cells treated with 10, 50, 100 and 500 nM CFI-400945 for 24, 48 and 72 hours demonstrated a time dependent decrease in PLK4 expression compared to the control (0.1% DMSO). Note, that at 24 hours, the expression of the transcript increased at 10, 50 and 100 nM, but not at 500111\4, correlating with the increase in centrioles' number. After 24 hrs of exposure to the inhibitor, the mRNA expression decreased progressively. (FIG. 8F) The rhabdoid tumor (G401, BT-12 and BT-16) and the MB (DAOY and D283) cell lines showed increase in centriole's number when treated with 100 nM of the PLK4i suggesting increase in PLK4 expression, whereas a significant decrease is observed with 500 nM. This "paradoxical effect" was not observed in the non-neoplastic human fibroblast cells (HFF-SCC058), which do not overexpress PLK4 (FIG. 6C).

Figure 9A:
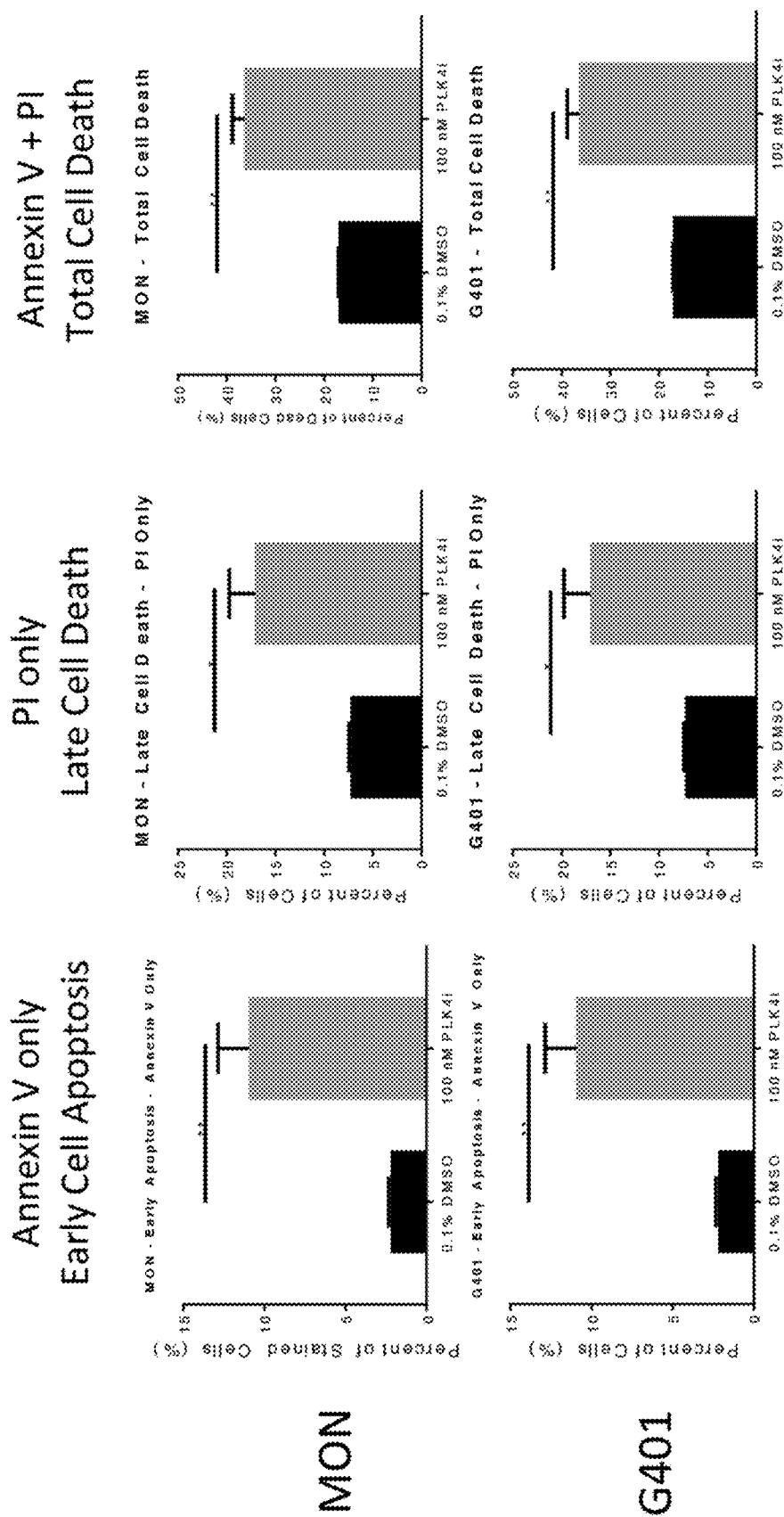
Figure 9A:
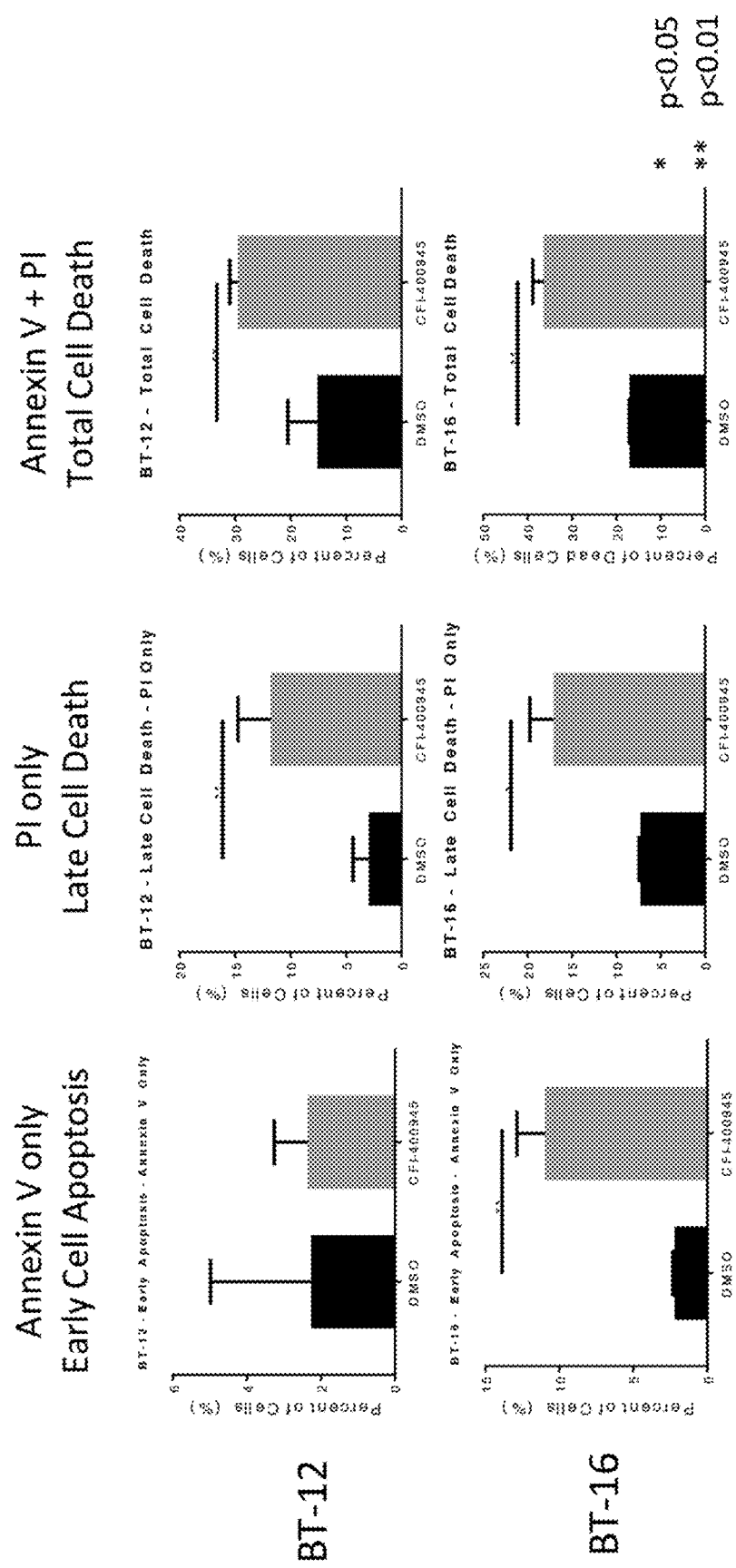
Figure 9B:
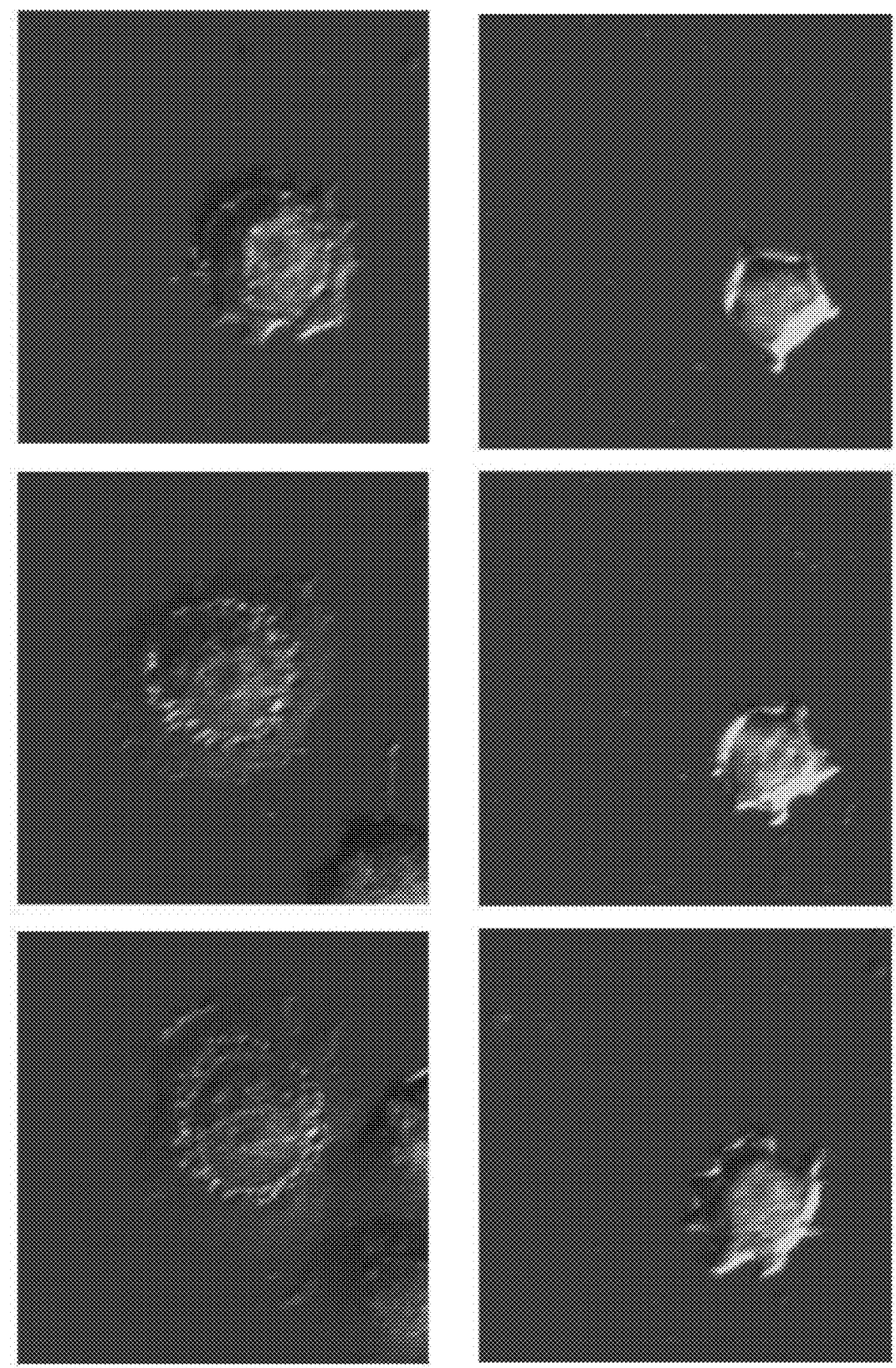

FIG. 9A, and FIG. 9B. CFI-400945 induced cell death in multiple pediatric rhabdoid cell lines. (FIG. 9A) Apoptosis was evaluated in four rhabdoid cell lines (MON, G401, BT-12 and BT-16) with 100 nM CFI-400945 for 48 hours and measured by flow cytometry. A significantly higher percentage of cells undergoing cell death in the initial 48 hours of treatment, was observed when compared to the control (0.1% DMSO). (FIG. 9B) Images of a cell undergoing apoptosis within 48 hours of treatment with 100 nM CFI-400945.

Figure 10A:
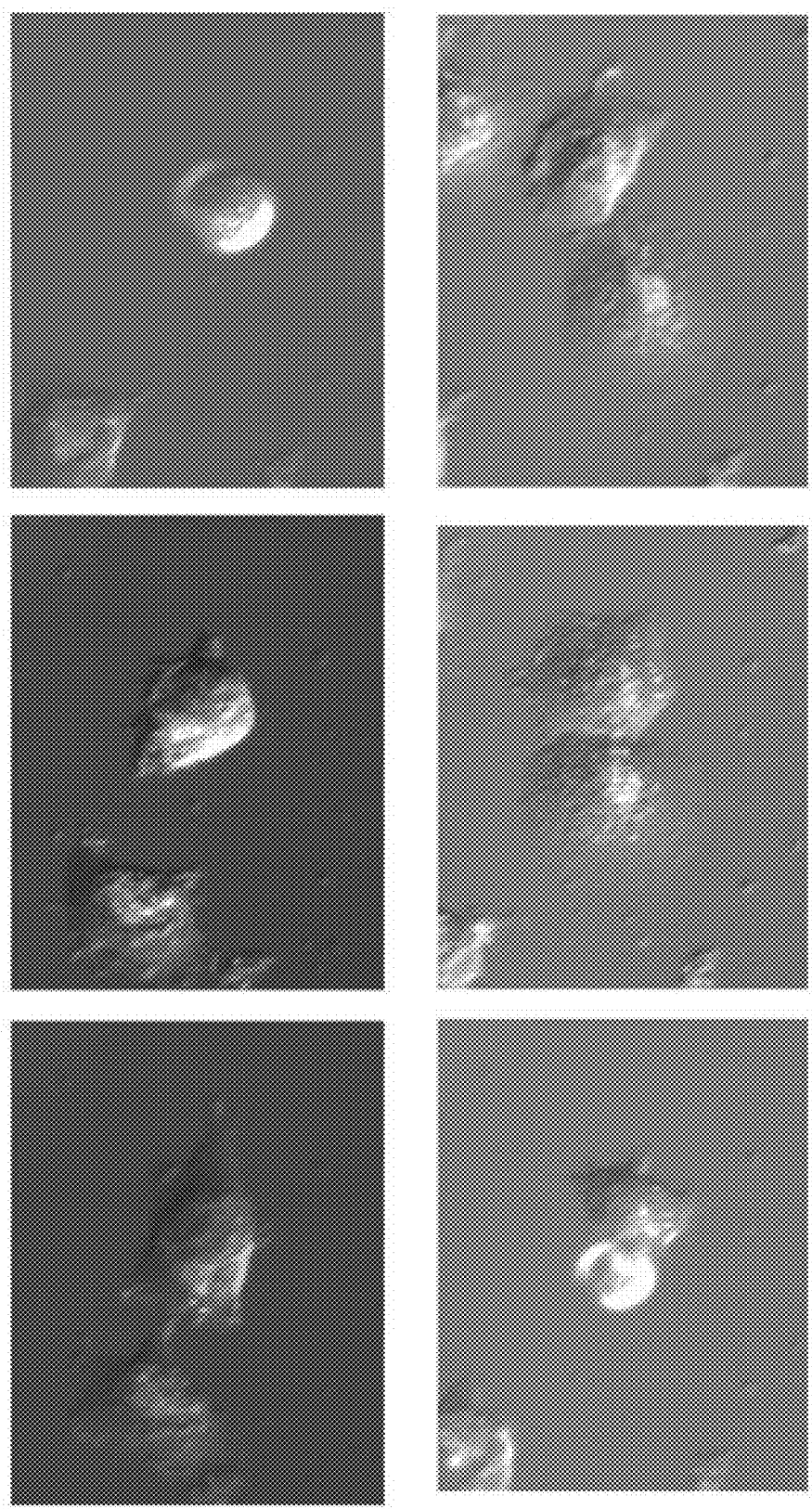
Figure 10A:
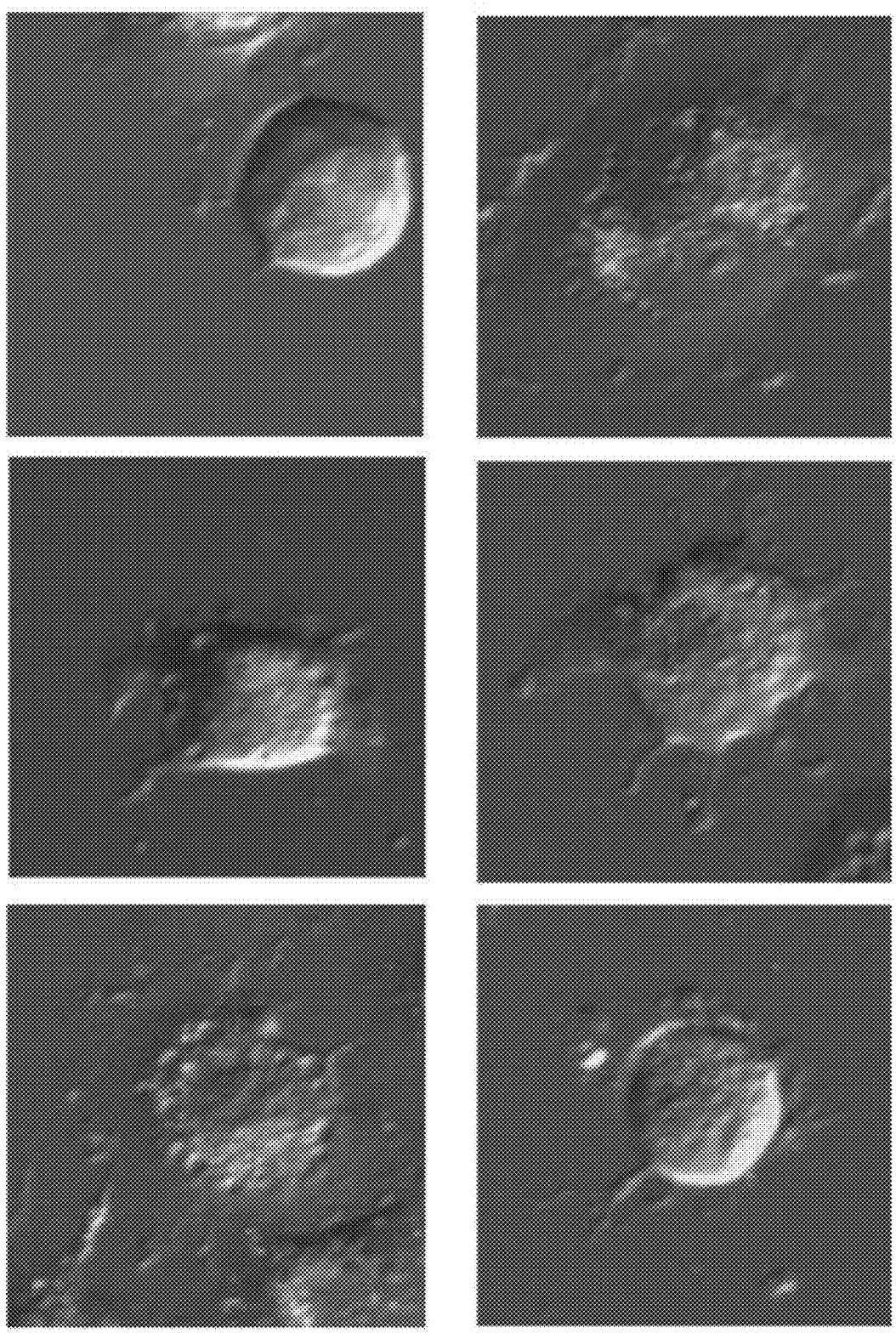
Figure 10B:
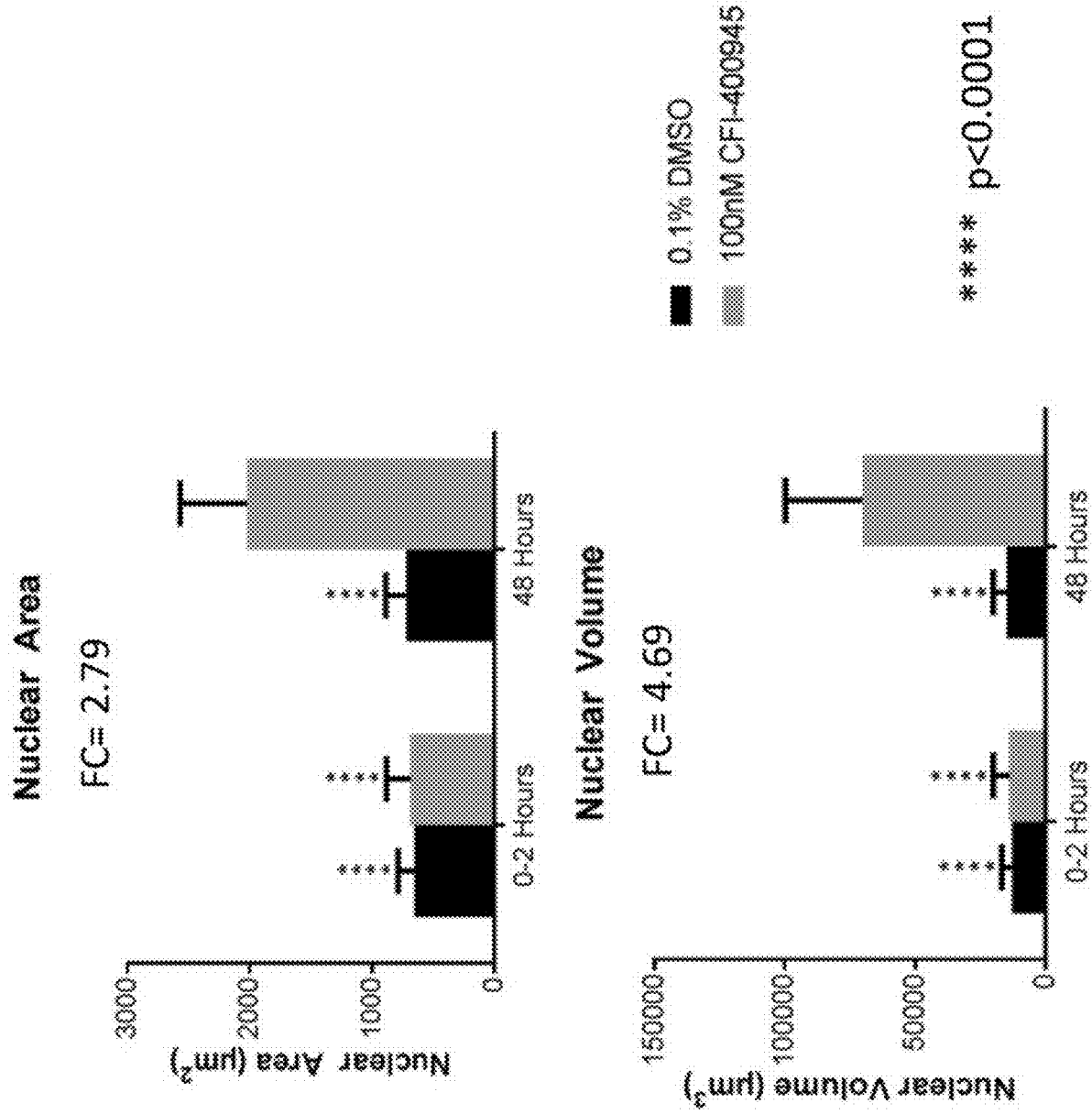
Figure 10C:
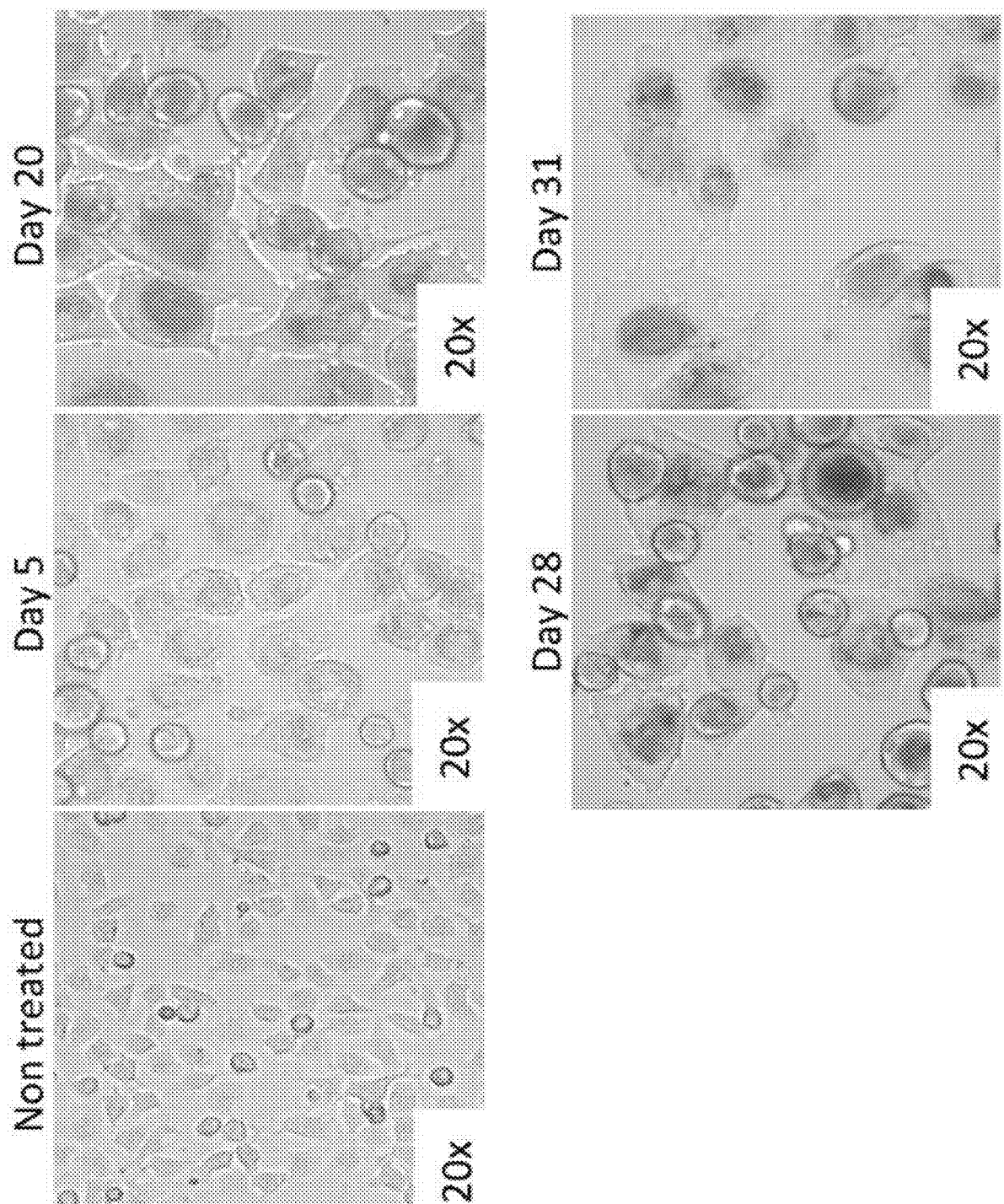

FIG. 10A, FIG. 10B, and FIG. 10C. Rhabdoid cells treated with the PLK4 inhibitor CFI-400945 displayed significant increase in cell size (hypertrophy). (FIG. 1.0A) Images of MON cells treated with 100 nM CFI-400945 or 0.1% DMSO (control) taken from the time-lapse video. Cells treated with 0.1% DMSO were observed to detach from the bottom of the dish and divide with two daughter cells reattaching to the plate. Cells treated with 100 nM CFI-400945 were observed to detach from the plate and then reattach without dividing as much larger, single cells. These images illustrate the phenomenon of DNA endoreduplication without cytokinesis secondary to the depletion of centrioles as an effect of PLK4 inhibition. (FIG. 109) The area and volume of the nuclei were measured for both the 0.1% DMSO (control) and 100 nM CFI-400945 treated cells within the first two hours and at 48 hours of treatment. A significant difference was observed for both area (FC=2.79; p-value<0.001) and volume (FC=4.69; p-value<0.001) after treatment. (FIG. 10C). Images of MON cells treated with 100 nM CFI-400945 for over 30 days displayed progressive cellular enlargement, culminating with cell death.

Figure 11:
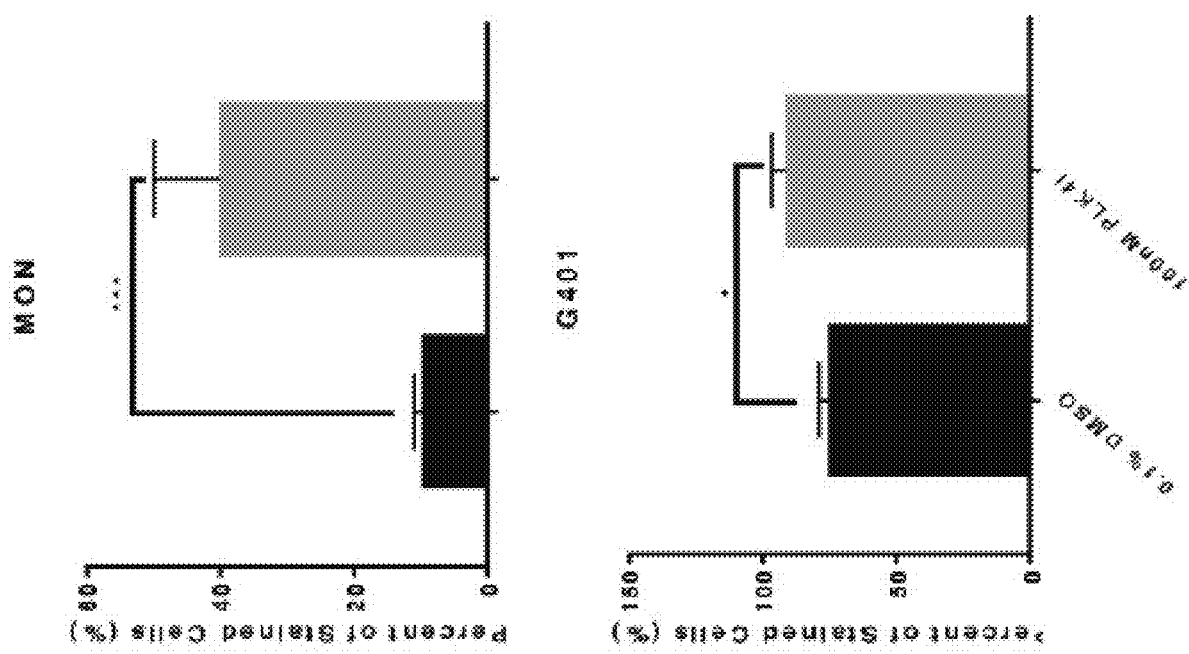
Figure 11:
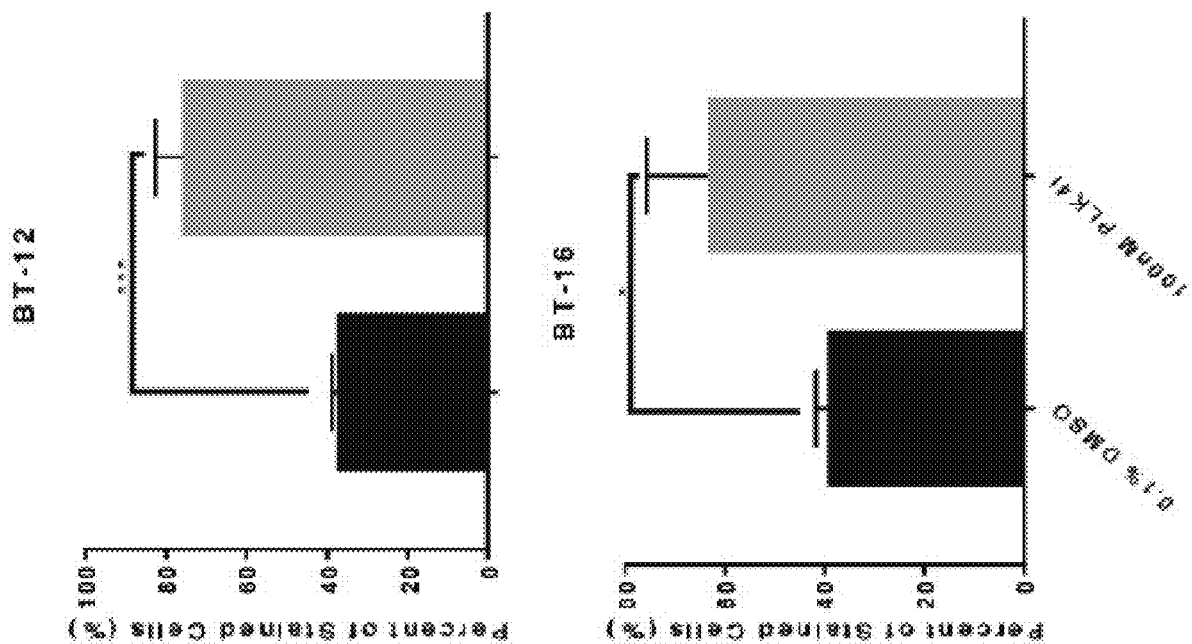
Figure 11:
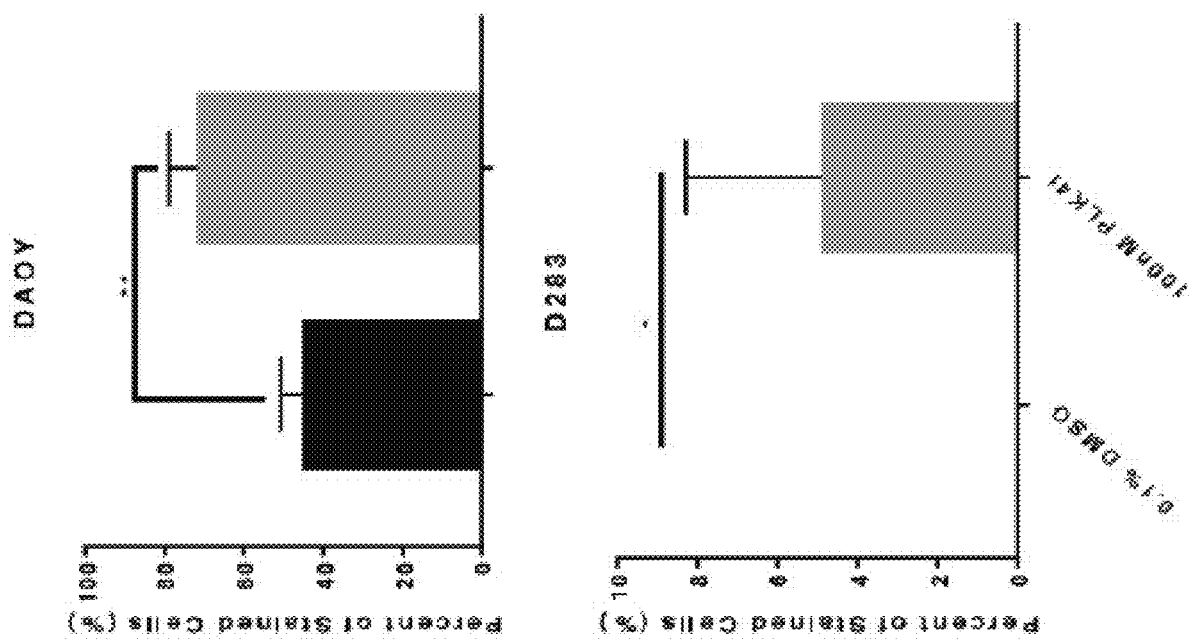
Figure 13A:
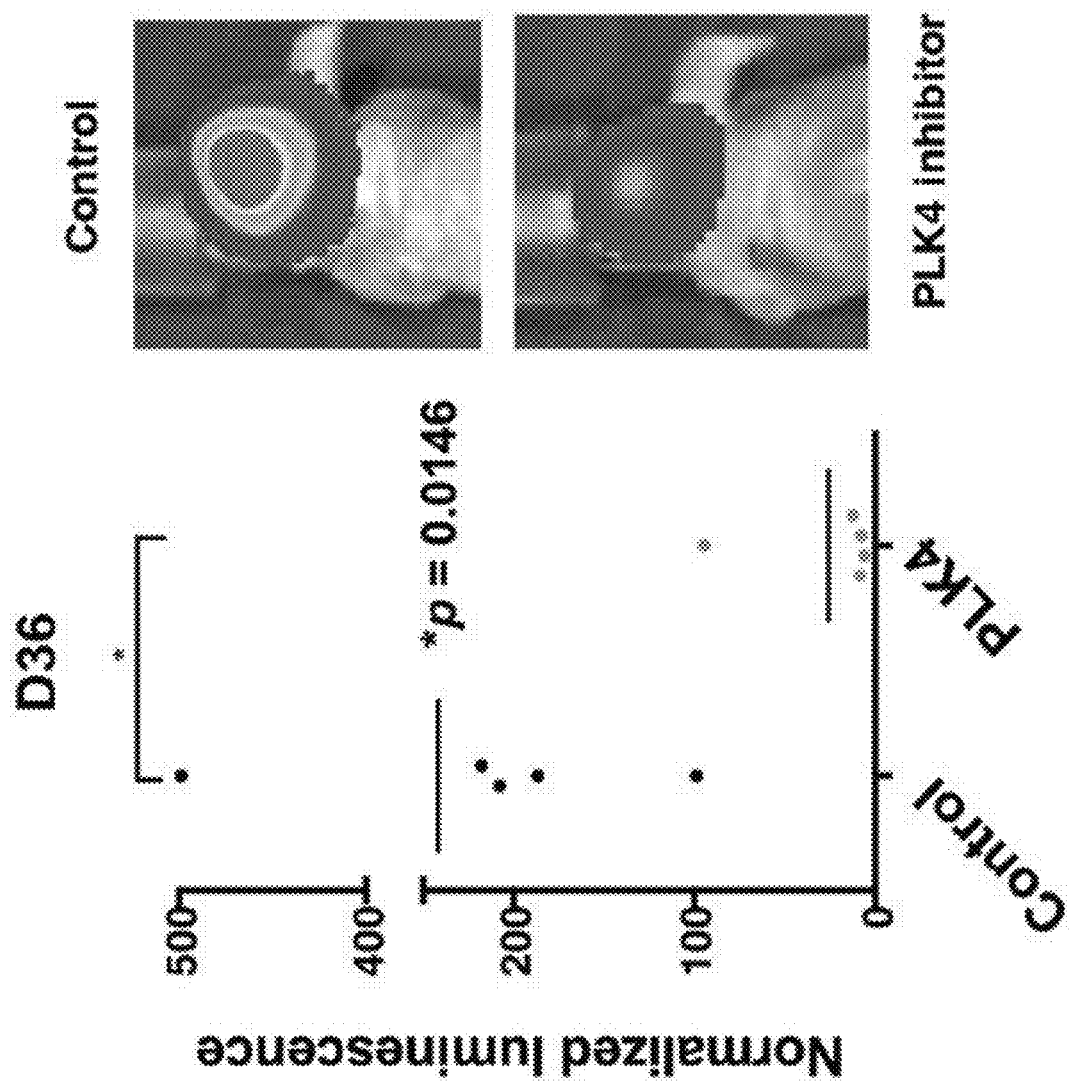
Figure 13B:
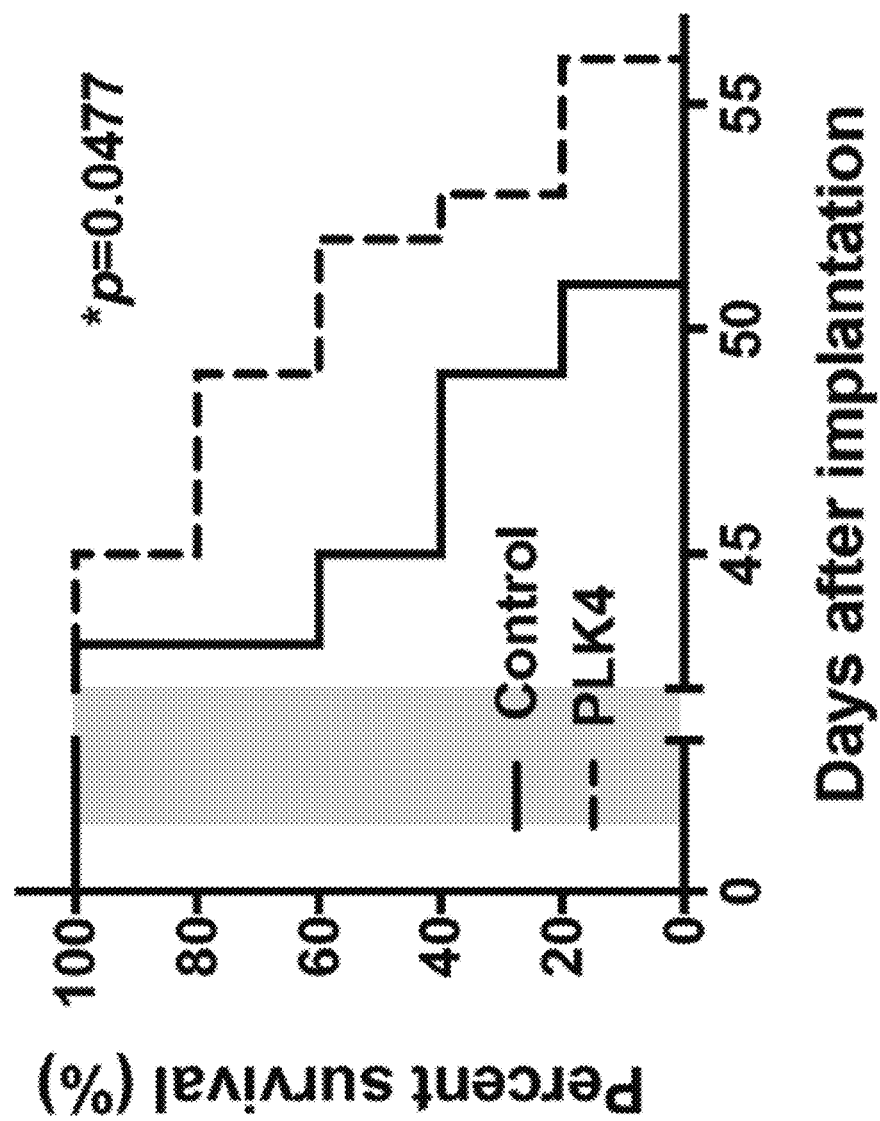
Figure 13C:
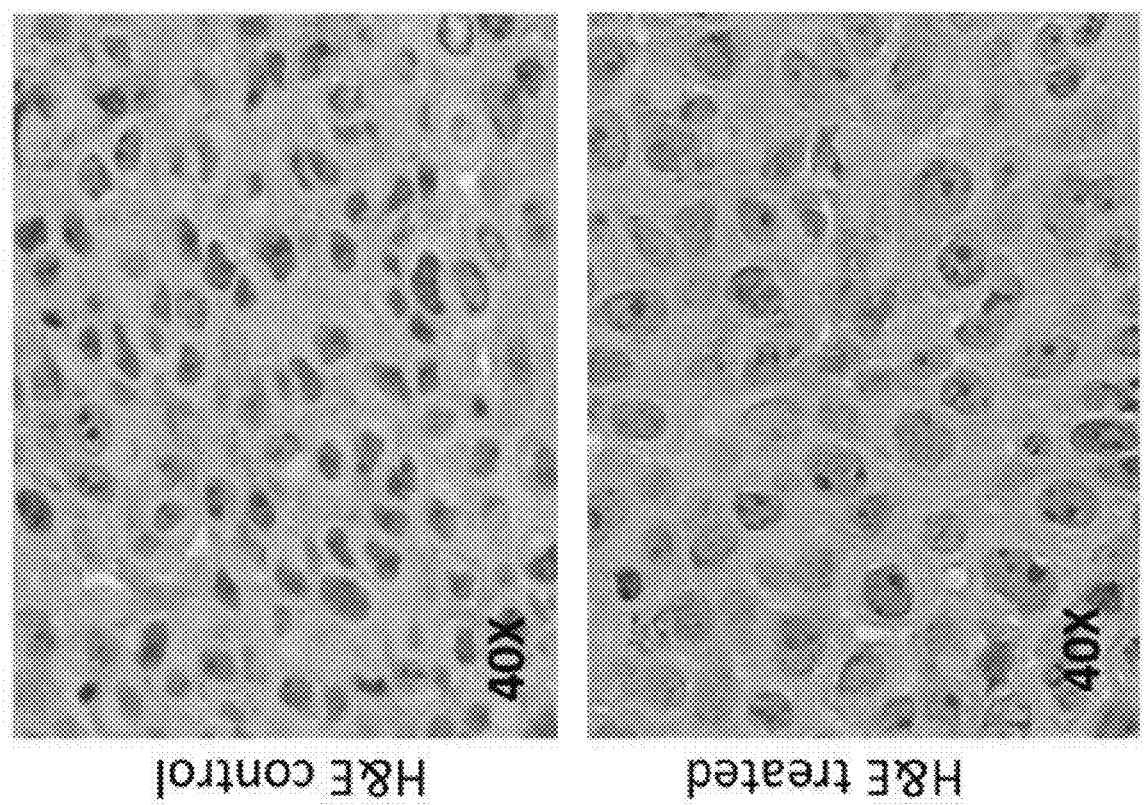
Figure 13D:
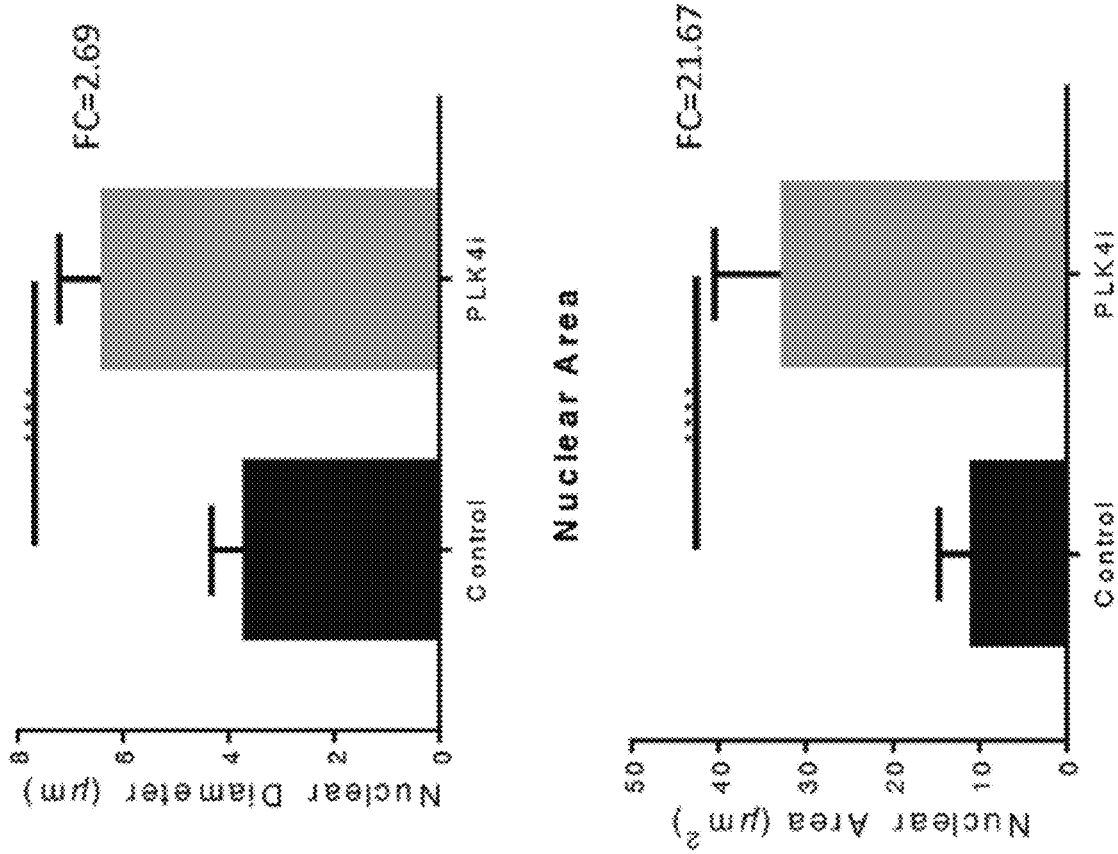

FIG. 11. RT and MB cells exposed the PLK4 inhibitor CFI-400945 underwent an irreversible state of cell cycle arrest—senescence. Beta galactosidase assay showed significant increase of senescent cells at 48 hours of CFI-400945 exposure (100 nM) in all cell lines (MON, G401, BT-12, BT-16 DAOY and D283).

FIG. 12. In vivo determination of brain-to-plasma ratio (B:P) demonstrated that CFI-400945 penetrates the brain-blood-barrier (BBB). Pharmacokinetic studies for determination of CFI-400945's brain-to-plasma ratio (B:P) were performed in fasted male CD-1 mice in triplicates. CFI-400945 was dosed orally (PO) at 7.5 mg/kg/day to the study group but not to the control group. Verapramil was used as internal standard. Blood and brain samples were collected 4 hours post-dose and the concentrations of CFI-400945 in plasma and brain homogenate were determined by LC-MS/MS (Liquid chromatography—mass spectrometry). (C) The average B:P for CFI-400945 was 0.0761±0.293.

FIG. 13A, FIG. 13B, FIG. 13C, and FIG. 13D. The PLK4i CFI-400945 promoted pharmacological inhibition of AT/RT xenografts. Orthotropic xenografts of BT-12 cells treated with CFI-400945 (orally) affected tumor growth and survival. Effects of the compound were also reflected on cell size at histological evaluation. (FIG. 13A) Images of AT/RT orthotropic xenografts in mice both control (untreated) and treated with CFI-400945 for 20 days (7.5 mg/kg). Mice treated with CFI-400945 displayed decreased luminescence compared to the control (untreated) mice (p=0.0146), indicating that CFI-400945 treatment inhibited tumor growth in vivo. (FIG. 13B) A survival curve displayed significant impact in survival of mice treated with CFI-400945 compared to the control (untreated) mice (p=0.0477). (FIG. 13C and FIG. 13D) Images of H&E stained slides from mice orthotropic xenografts showed significant increase in nuclear diameter (FC=2.69; p-value<0.0001) and nuclear area (FC=21.67; p-value<0.0001) in the tumor cells of the treated mice compared to the control (untreated). *log-rank test.

DETAILED DESCRIPTION

The present invention is described herein using several definitions, as set forth below and throughout the application.

Unless otherwise specified or indicated by context, the terms "a", "an", and "the" mean "one or more." For example, "a PLK4 inhibitor" should be interpreted to mean "one or more PLK4 inhibitors."

As used herein, "about," "approximately," "substantially," and "significantly" will be understood by persons of ordinary skill in the art and will vary to some extent on the context in which they are used. If there are uses of these terms which are not clear to persons of ordinary skill in the art given the context in which they are used, "about" and "approximately" will mean plus or minus ≤10% of the particular term and "substantially" and "significantly" will mean plus or minus >10% of the particular term.

As used herein, the terms "include" and "including" have the same meaning as the terms "comprise" and "comprising" in that these latter terms are "open" transitional terms that do not limit claims only to the recited elements succeeding these transitional terms. The term "consisting of," while encompassed by the term "comprising," should be interpreted as a "closed" transitional term that limits claims only to the recited elements succeeding this transitional term. The term "consisting essentially of," while encompassed by the term "comprising," should be interpreted as a "partially closed" transitional term which permits additional elements succeeding this transitional term, but only if those additional elements do not materially affect the basic and novel characteristics of the claim.

As used herein, a "subject" may be interchangeable with "patient" or "individual" and means an animal, which may be a human or non-human animal, in need of treatment.

A "subject in need of treatment" may include a subject having a disease, disorder, or condition that is responsive to therapy with a polo-like kinase 4 (PLK4) inhibitor. For example, a "subject in need of treatment" may include a subject having a cell proliferative disease, disorder, or condition such as cancer. In particular, a "subject in need of treatment" may include a subject having an embryonal tumor. Embryonal tumors typically are composed of undifferentiated cells similar to the ones in a developing embryo and are almost exclusively encountered in children, in which they are referred to as pediatric embryonal tumors. (See Tulla et al., "Incidence, Trends, and Survival of Children with Embryonal Tumors, Pediatrics, September 2015, vol 136, Issue 3, e623-e634, the content of which is incorporated herein by reference in its entirety). A "subject having an embryonal tumor" may include, but is not limited to, a subject having a malignant rhabdoid tumor (MRT), a rhabdoid tumor of the kidney (RTK), an atypical teratoid/rhabdoid tumors (ATRTs) of the central nervous system (CNS), and a medulloblastoma (MB), a primitive neuroectodermal tumor (PNETs), a rhabdomyosarcoma, and a medulloepithelioma. A "subject having an embryonal tumor" may include, but is not limited to, a subject having a tumor of the central nervous system (CNS) including a subject having a brain tumor.

A "subject in need of treatment" may include a pediatric subject. Generally, a pediatric subject is a human subject of an age of 12 years or less (or 11 years, 10 years, 9 years, 8 years, 7 years, 6 years, 5 years, 4 years, 3 years, 2 years, or 1 year or less).

As used herein, the phrase "effective amount" shall mean that drug dosage that provides the specific pharmacological response for which the drug is administered in a significant number of subjects in need of such treatment. An effective amount of a drug that is administered to a particular subject in a particular instance will not always be effective in treating the conditions/diseases described herein, even though such dosage is deemed to be a therapeutically effective amount by those of skill in the art.

Compounds utilized in the disclosed pharmaceutical compositions and treatment methods may inhibit one or more biological activities of polo-like kinase 4 (PLK4). For example, the disclosed compounds may inhibit one or more biological activities of PLK4 at a concentration of less than about 100 µM, 50 µM, 10 µM, 1 µM, 0.1 µM, 0.05 µM, 0.01 µM, 0.005 µM, 0.001 µM, or less. Biological activities of PLK4 that may be inhibited by the disclosed compounds may include, but are not limited to, inhibition of serine/threonine kinase activity, which may in turn lead to inhibition of biological activities such as centriole duplication. Biological activities of PLK4 that may be inhibited by the disclosed compounds may include, but are not limited to, inhibition of homodimer formation by PLK4, which may in turn lead to inhibition of biological activities such as centriole duplication. The disclosed compounds may inhibit the growth of cells that express PLK4 (preferably at a concentration of less than about 100 μM, 50 μM, 10 μM, 1 μM, 0.1 μM, 0.05 μM, 0.01 μM, 0.005 μM, 0.001 μM, or less). The disclosed compounds may not inhibit the growth of cells that do not express PLK4 (preferably at a concentration of greater than about 0.001 μM, 0.005 μM, 0.01 μM, 0.5 μM, 0.1 μM, 1.0 μM, 10 μM, and 100 μM or higher). As such, in the disclosed treatment methods, the disclosed compounds may be administered at a dose that delivers a concentration of 100 μM, 50 μM, 10 μM, 1 μM, 0.1 μM, 0.05 μM, 0.01 μM, 0.005 μM, 0.001 μM or less (or a concentration within a range bounded by any of these concentrations such as a range of 0.01-10 μM).

The disclosed compounds may exhibit toxicity to cancer cells, including embryonal tumor cells as discussed herein. For example, the disclosed compounds may exhibit toxicity to cancer cells at a concentration of less than about 100 μM, 50 μM, 10 μM, 1 μM, 0.5 μM, 0.1 μM, 0.05 μM, 0.01 μM, 0.005 μM, 0.001 μM, or less. Cell toxicity, proliferation, and growth inhibition thereof by the presently disclosed compounds may be assessed by cell viability methods disclosed in the art including colorimetric assays that utilize dyes such as MTT, XTT, and MTS to assess cell viability. Preferably, the disclosed compounds have an IC$_{50}$ of less than about 10 μM, 5 μM, 1 μM, 0.5 μM, 0.1 μM, 0.05 μM, 0.01 μM, 0.005 μM, 0.001 μM, or less for killing cancer cells in the selected assay. Preferably, the disclosed compounds do not exhibit toxicity to non-cancer cells at a concentration greater than about 0.001 μM, 0.005 μM, 0.01 μM, 0.05 μM, 0.1 μM, 0.5 μM, 1.0 μM, 10 μM, and 100 μM or higher in the selected assay.

The compounds utilized in the disclosed methods and pharmaceutical compositions may include so-called "spiro cyclo-propyl indolinone compounds," which have been disclosed in the art. (See, e.g., U.S. Pat. Nos. 8,263,596; 8,481,525; 8,481,533; 8,999,969; 9,139,563; by Sampson et al., the contents of which are incorporated herein by reference in their entireties). In particular, the compounds utilized in the disclosed methods and pharmaceutical compositions may include, for example, a compound having the following Formula I or a pharmaceutically acceptable salt thereof:

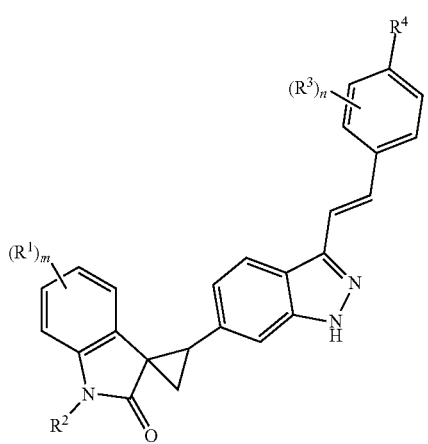

where:
m is 0-4 and each R$^1$ is independently H, halo, C$_{1-6}$ alkyl (e.g., methyl), C$_{1-6}$ haloalkyl (e.g., trifluoromethyl), C$_{1-6}$ alkoxy (e.g., methoxy), or hydroxyl;

R$^2$ is hydrogen or C$_{1-6}$ alkyl;

n is 0-4 and each R$^3$ is independently halogen, hydroxyl, thiol, nitro, cyano, amino, C$_{1-6}$ alkyl (e.g., methyl), C$_{1-6}$ haloalkyl (e.g., trifluoromethyl), C$_{1-6}$ alkoxy (e.g., methoxy);

R$^4$ is —(CH$_2$)$_{0-3}$—N-morpholinyl, wherein the morpholinyl group optionally is substituted at one or more positions with C$_{1-6}$ alkyl (e.g., N-2,6-dimethylmorpholinyl); —(CH$_2$)$_{0-3}$—N-piperidinyl, wherein the piperidinyl group optionally is substituted at one or more positions with C$_{1-6}$ alkyl; (CH$_2$)$_{0-3}$—N-pyrrolidinyl, wherein the pyrrolidinyl group optionally is substituted at one or more positions with C$_{1-6}$ alkyl; —(CH$_2$)$_{0-3}$—N-piperazinyl, wherein the piperazinyl group optionally is substituted at one or more positions with C$_{1-6}$ alkyl; —(CH$_2$)$_{0-3}$—N-oxazepanyl, wherein the oxazepanyl group optionally is substituted at one or more positions with C$_{1-6}$ alkyl.

In some embodiments, the compound utilized in the disclosed methods and pharmaceutical compositions is a compound having the following Formula Ia or a pharmaceutically acceptable salt thereof:

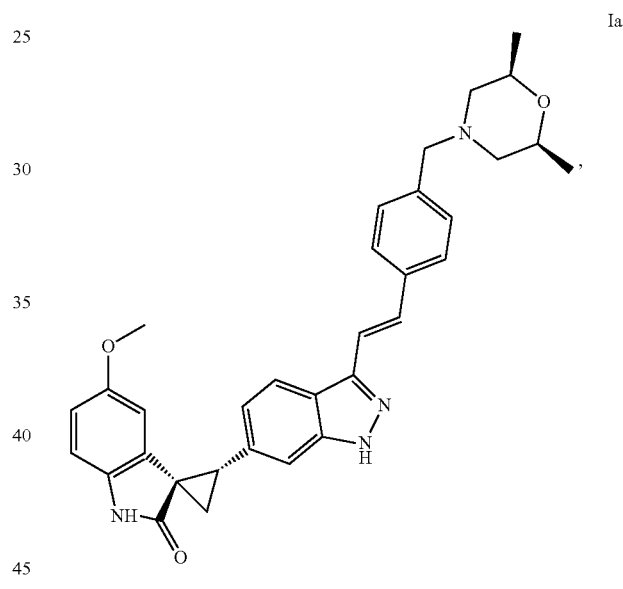

which otherwise is referred to as (1R,2S)-(E)-2-(3-(4-trans-2,6-dimethylmorpholino)methyl)styryl)-1H-indazol-6-yl)-5'-methoxyspiro[cyclopropane-1,3'-indolin]-2' one or "CFI-400945."

The formulae of the compounds disclosed herein should be interpreted as encompassing all possible stereoisomers, enantiomers, or epimers of the disclosed compounds unless the formulae indicates a specific stereoisomer, enantiomer, or epimer. The formulae of the compounds disclosed herein should be interpreted as encompassing salts, esters, amides, or solvates thereof of the compounds. A composition comprising an enantiomeric compound may comprise greater than about 50%, 60%, 70%, 80%, 90%, 95%, 96%, 97%, 98%, or 99% of a given enantiomer of the compound (e.g., greater than about 99% of an R-enantiomer of a given compound). A composition comprising an enantiomeric compound may be effectively "enantiopure," meaning that the composition comprises only a single enantiomer of an enantiomeric compound.

Also disclosed are pharmaceutical compositions comprising the disclosed PLK4 inhibitors and a suitable pharmaceutical carrier, excipient, or diluent. The disclosed pharmaceutical compositions may comprise an effective amount of the PLK4 inhibitors for inhibiting the growth of cancer cells when administered to a subject in need thereof.

Also disclosed are methods for treating cell proliferation diseases and disorders such as cancer. The methods may include administering the disclosed PLK4 inhibitors or pharmaceutical compositions comprising the disclosed compounds to a subject in need thereof, for example, to a subject having cancer. Cell proliferative diseases and disorders treated by the disclosed methods may include, but are not limited to, embryonal tumors as discussed herein.

In some embodiments, the subject may be administered a PLK4 inhibitor at a dose as high as about 0.05 mg, 0.1 mg, 0.2 mg, 0.5 mg, 1 mg, 2 mg, 5 mg, 10 mg, 50 mg, 100 mg, 200 mg, 500 mg, 1000 mg, or 2000 mg once daily, twice daily, three times daily, four times daily, once weekly, twice weekly, or three times per week (or no more than three times per week). In some embodiments, the subject may be administered a PLK4 inhibitor at a dose no higher than high 2000 mg, 1000 mg, 500 mg, 200 mg, 100 mg, 50 mg, 20 mg, 10 mg, 5 mg, 2 mg, 1 mg, 0.5 mg, 0.2 mg, 0.1 mg, 0.05 mg or less once daily, twice daily, three times daily, four times daily, once weekly, twice weekly, or three times per week (or no more than three times per week) in order to treat secondary hyperparathyroidism and/or to treat or prevent the symptoms thereof in a subject. Minimal and/or maximal doses of the PLK4 inhibitor may include doses falling within dose ranges having as end-points any of these disclosed doses (e.g., 2.5 mg-200 mg).

In some embodiments, a minimal dose level of the PLK4 inhibitor for achieving therapy may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of the PLK4 inhibitor for achieving therapy may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the PLK4 inhibitor for achieving therapy may include dose levels falling within ranges having as end-points any of these disclosed dose levels (e.g., 500-2000 ng/kg body weight of the subject).

As used herein, "administering" mean introducing a compound into the body, preferably into the systemic circulation or the cerebrospinal fluid (CSF), as described in more detail below. Examples include but are not limited to oral, topical, buccal, sublingual, pulmonary, transdermal, transmucosal, as well as subcutaneous, intraperitoneal, intravenous, and intramuscular injection or in the form of liquid or solid doses via the alimentary canal, and intrathecal administration.

In the disclosed treatment methods, the subject may be administered combination therapy where the subject is administered an additional treatment as known in the art in addition to administering the inhibitor of PLK4 to the subject. Methods for treating embryonal tumors are known in the art. (See, e.g., Geyer et al., "Multiagent chemotherapy and deferred radiotherapy in infants with malignant brain tumors: a report from the Children's Cancer Group," J Clin Oncol 23 (30): 7621-31, 2005; Chi et al., "Feasibility and response to induction chemotherapy intensified with high-dose methotrexate for young children with newly diagnosed high-risk disseminated medulloblastoma," J Clin Oncol 22 (24): 4881-7, 2004; Packer et al., "Outcome for children with medulloblastoma treated with radiation and cisplatin, CCNU, and vincristine chemotherapy. J Neurosurg 81 (5): 690-8, 1994; Bailey et al., "Prospective randomised trial of chemotherapy given before radiotherapy in childhood medulloblastoma," International Society of Paediatric Oncology (SIOP) and the (German) Society of Paediatric Oncology (GPO): SIOP II. Med Pediatr Oncol 25 (3): 166-78, 1995; Kortmann et al., "Postoperative neoadjuvant chemotherapy before radiotherapy as compared to immediate radiotherapy followed by maintenance chemotherapy in the treatment of medulloblastoma in childhood: results of the German prospective randomized trial HIT '91," Int J Radiat Oncol Biol Phys 46 (2): 269-79, 2000; Packer et al., "Phase III study of craniospinal radiation therapy followed by adjuvant chemotherapy for newly diagnosed average-risk medulloblastoma," J Clin Oncol 24 (25): 4202-8, 2006; Taylor et al., "Results of a randomized study of preradiation chemotherapy versus radiotherapy alone for nonmetastatic medulloblastoma: The International Society of Paediatric Oncology/United Kingdom Children's Cancer Study Group PNET-3 Study," J Clin Oncol 21 (8): 1581-91, 2003; Oyharcabal-Bourden et al., "Standard-risk medulloblastoma treated by adjuvant chemotherapy followed by reduced-dose craniospinal radiation therapy: a French Society of Pediatric Oncology Study," J Clin Oncol 23 (21): 4726-34, 2005; Packer et al., "Treatment of children with medulloblastomas with reduced-dose craniospinal radiation therapy and adjuvant chemotherapy: A Children's Cancer Group Study," J Clin Oncol 17 (7): 2127-36, 1999; Nageswara Rao et al., "Cumulative cisplatin dose is not associated with event-free or overall survival in children with newly diagnosed average-risk medulloblastoma treated with cisplatin based adjuvant chemotherapy: report from the Children's Oncology Group," Pediatr Blood Cancer 61 (1): 102-6, 2014; Evans et al., "The treatment of medulloblastoma. Results of a prospective randomized trial of radiation therapy with and without CCNU, vincristine, and prednisone," J Neurosurg 72 (4): 572-82, 1990; Jakacki et al., "Outcome of children with metastatic medulloblastoma treated with carboplatin during craniospinal radiotherapy: a Children's Oncology Group Phase I/II study," J Clin Oncol 30 (21): 2648-53, 2012; von Bueren et al., "Treatment of Children and Adolescents With Metastatic Medulloblastoma and Prognostic Relevance of Clinical and Biologic Parameters," J Clin Oncol 34 (34): 4151-4160, 2016; Grill et al., "Treatment of medulloblastoma with postoperative chemotherapy alone: an SFOP prospective trial in young children," Lancet Oncol 6 (8): 573-80, 2005; and Rutkowski et al., "Treatment of early childhood medulloblastoma by postoperative chemotherapy alone," N Engl J Med 352 (10): 978-86, 2005; the contents of which are incorporated by reference in their entireties). The additional treatment may be administered to the subject before, concurrently with, or after the subject is administered the inhibitor of PLK4.

In some embodiments, the subject is administered a chemotherapeutic agent in addition to the PLK4 inhibitor. In particular, the subject may be administered a DNA-damaging agent in combination with the inhibitor of PLK4, where the DNA-damaging agent may be administered before, concurrently with, or after the PLK4 inhibitor is administered. Preferably, the DNA-damaging agent is administered to the subject after the PLK4 is administered. Suitable DNA-damaging agents may include, but are not limited to cisplatin, carboplatin, oxaliplatin, methotrexate, doxorubicin, daunorubicin, and etoposide.

In the disclosed treatment methods, the subject may be administered combination therapy where radiation therapy is administered to the subject in addition to the inhibitor of PLK4. The subject may be administered radiation therapy before, concurrently with, or after the PLK4 inhibitor is administered to the subject. Preferably, radiation therapy is administered to the subject after the PLK4 is administered to the subject.

The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to 100 mg/kg body weight (preferably about 0.5 to 20 mg/kg body weight, more preferably about 0.1 to 10 mg/kg body weight). In some embodiments, after the pharmaceutical composition is administered to a patient (e.g., after about 1, 2, 3, 4, 5, or 6 hours post-administration), the concentration of the compound at the site of action is about 2 to 10 µM.

As indicated above, pharmaceutically acceptable salts of the compounds are contemplated and also may be utilized in the disclosed methods. The term "pharmaceutically acceptable salt" as used herein, refers to salts of the compounds which are substantially non-toxic to living organisms. Typical pharmaceutically acceptable salts include those salts prepared by reaction of the compounds as disclosed herein with a pharmaceutically acceptable mineral or organic acid or an organic or inorganic base. Such salts are known as acid addition and base addition salts. It will be appreciated by the skilled reader that most or all of the compounds as disclosed herein are capable of forming salts and that the salt forms of pharmaceuticals are commonly used, often because they are more readily crystallized and purified than are the free acids or bases.

Acids commonly employed to form acid addition salts may include inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of suitable pharmaceutically acceptable salts may include the sulfate, pyrosulfate, bisulfate, sulfite, bisulfate, phosphate, monohydrogenphosphate, dihydrogenphosphate, metaphosphate, pyrophosphate, bromide, iodide, acetate, propionate, decanoate, caprylate, acrylate, formate, hydrochloride, dihydrochloride, isobutyrate, caproate, heptanoate, propiolate, oxalate, malonate, succinate, suberate, sebacate, fumarate, maleat-, butyne-.1,4-dioate, hexyne-1,6-dioate, benzoate, chlorobenzoate, methylbenzoate, hydroxybenzoate, methoxybenzoate, phthalate, xylenesulfonate, phenylacetate, phenylpropionate, phenylbutyrate, citrate, lactate, alpha-hydroxybutyrate, glycolate, tartrate, methanesulfonate, propanesulfonate, naphthalene-1-sulfonate, naphthalene-2-sulfonate, mandelate, and the like.

Base addition salts include those derived from inorganic bases, such as ammonium or alkali or alkaline earth metal hydroxides, carbonates, bicarbonates, and the like. Bases useful in preparing such salts include sodium hydroxide, potassium hydroxide, ammonium hydroxide, potassium carbonate, sodium carbonate, sodium bicarbonate, potassium bicarbonate, calcium hydroxide, calcium carbonate, and the like.

It should be recognized that the particular counter-ion forming a part of any salt of a compound disclosed herein is usually not of a critical nature, so long as the salt as a whole is pharmacologically acceptable and as long as the counterion does not contribute undesired qualities to the salt as a whole. Undesired qualities may include undesirably solubility or toxicity.

Pharmaceutically acceptable esters and amides of the compounds can also be employed in the compositions and methods disclosed herein. Examples of suitable esters include alkyl, aryl, and aralkyl esters, such as methyl esters, ethyl esters, propyl esters, dodecyl esters, benzyl esters, and the like. Examples of suitable amides include unsubstituted amides, monosubstituted amides, and disubstituted amides, such as methyl amide, dimethyl amide, methyl ethyl amide, and the like.

In addition, the methods disclosed herein may be practiced using solvate forms of the compounds or salts, esters, and/or amides, thereof. Solvate forms may include ethanol solvates, hydrates, and the like.

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (ProSolv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, pulmonary and intrathecal route. Examples of pharmaceutical compositions for oral administration include capsules, syrups, concentrates, powders and granules.

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) and intrathecal route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

ILLUSTRATIVE EMBODIMENTS

The following Embodiments are illustrative and are not intended to limit the scope of the claimed subject matter.

Embodiment 1

A method for treating a pediatric embryonal tumor in a subject in need thereof, the method comprising administering a pharmaceutical composition comprising an inhibitor of polo-like kinase 4 (PLK4) and a suitable pharmaceutical carrier, diluent, or excipient.

Embodiment 2

The method of embodiment 1, wherein the pediatric embryonal tumor is a peripheral malignant rhabdoid tumor (MRT), a rhabdoid tumor of the kidney (RTK), or a central nervous system (CNS) atypical teratoid/rhabdoid tumor (ATRT).

Embodiment 3

The method of embodiment 1 or 2, wherein the tumor is a tumor of the central nervous system.

Embodiment 4

The method of any of the foregoing embodiments, wherein the tumor is a brain tumor.

Embodiment 5

The method of embodiment 1, wherein the tumor is a medulloblastoma (MB).

Embodiment 6

The method of any of the foregoing embodiment wherein the inhibitor of PLK4 is a compound having the following Formula I or a pharmaceutically acceptable salt thereof:

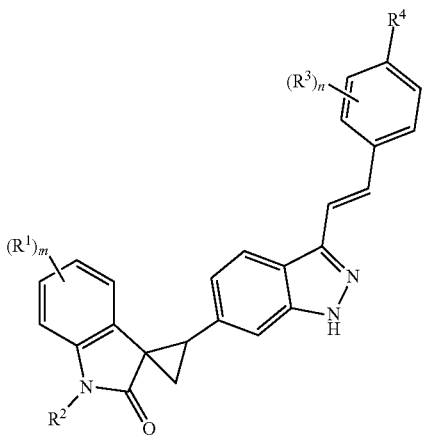

wherein:
m is 0-4 and each $R^1$ is independently H, halo, $C_{1-6}$ alkyl (e.g., methyl), $C_{1-6}$ haloalkyl (e.g., trifluoromethyl), $C_{1-6}$ alkoxy (e.g., methoxy), or hydroxyl;
$R^2$ is hydrogen or $C_{1-6}$ alkyl;
n is 0-4 and each $R^3$ is independently halogen, hydroxyl, thiol, nitro, cyano, amino, $C_{1-6}$ alkyl (e.g., methyl), $C_{1-6}$ haloalkyl (e.g., trifluoromethyl), $C_{1-6}$ alkoxy (e.g., methoxy);
$R^4$ is $C_{1-6}$ alkyl-N-morpholinyl, wherein the morpholinyl group optionally is substituted at one or more positions with $C_{1-6}$ alkyl (e.g., N-2,6-dimethylmorpholinyl).

Embodiment 7

The method of any of the foregoing embodiments, wherein the inhibitor of PLK4 is a compound having the following Formula Ia or a pharmaceutically acceptable salt thereof:

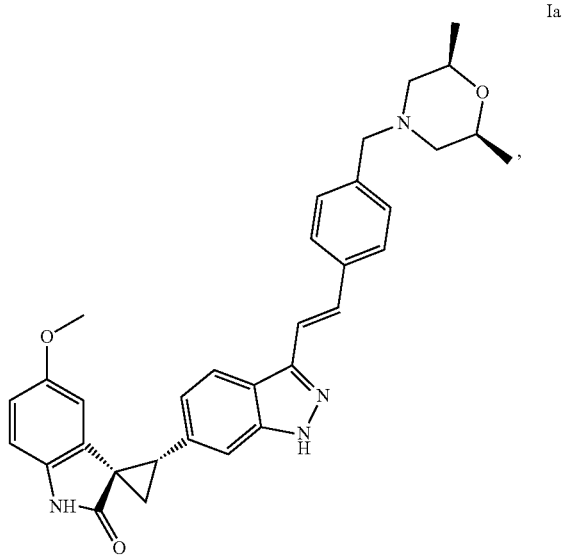 [SMILES: COc1ccc2c(c1)[C@]1(C[C@H]1c1ccc3c(/C=C/c4ccc(CN5C[C@@H](C)O[C@@H](C)C5)cc4)n[nH]c3c1)C(=O)N2]

which otherwise is referred to as (1R,2S)-(E)-2-(3-(4-trans-2,6-dimethylmorpholino)methyl)styryl)-1H-indazol-6-yl)-5'-methoxyspiro[cyclopropane-1,3'-indolin]-2' one or CFI-400945.

Embodiment 8

The method of any of the foregoing embodiments, further comprising administering chemotherapy to the subject.

Embodiment 9

The method of embodiment 8, wherein administering chemotherapy to the subject comprises administering a DNA-damaging agent to the subject.

Embodiment 10

The method of embodiment 9, wherein the DNA-damaging agent is selected from the group consisting of cisplatin, carboplatin, oxaliplatin, methotrexate, doxorubicin, daunorubicin, and etoposide.

Embodiment 11

The method of any of the foregoing embodiments, further comprising administering radiation therapy to the subject.

Embodiment 12

The method of any of the foregoing embodiments, wherein the pharmaceutical composition is administered orally.

Embodiment 13

The method of any of the foregoing embodiments, wherein the pharmaceutical composition is administered daily.

Embodiment 14

The method of any of the foregoing embodiments, wherein the composition is administered twice a week.

Embodiment 15

The method of any of the foregoing embodiment, wherein the composition is administered once a week.

EXAMPLES

The following Examples are illustrative and are not intended to limit the scope of the claimed subject matter.

Example 1—A Functional Screening of the Kinome Identifies the Polo-Like Kinase 4 as a Potential Therapeutic Target for Malignant Rhabdoid Tumors, and Possibly Other Embryonal Tumors of the Brain Reference is made to Sredni et al., "A functional screening of the kinome identifies the Polo-like kinase 4 as a potential therapeutic target for malignant rhabdoid tumors, and possibly, other embryonal tumors of the brain," Pediatr Blood Cancer. 2017; 00:e26551, pages 1-10, the content of which is incorporated herein by reference in its entirety.
Abstract
Purpose.
Malignant rhabdoid tumors (MRTs) are deadly embryonal tumors of the infancy. With poor survival and modest response to available therapies, more effective and less toxic treatments are needed. We hypothesized that a systematic screening of the kinome will reveal kinases that drive rhabdoid tumors and can be targeted by specific inhibitors.

Methods.

We individually mutated 160 kinases in a well-characterized rhabdoid tumor cell line (MON) using lentiviral clustered regularly interspaced short palindromic repeats (CRISPR)/CRISPR-associated protein 9 (Cas9). The kinase that most significantly impaired cell growth was further validated. Its expression was evaluated by microarray gene expression (GE) within 111 pediatric tumors, and functional assays were performed. A small molecule inhibitor was tested in multiple rhabdoid tumor cell lines and its toxicity evaluated in zebrafish larvae.

Results.

The Polo-like kinase 4 (PLK4) was identified as the kinase that resulted in higher impairment of cell proliferation when mutated by CRISPR/Cas9. PLK4 CRISPR-mutated rhabdoid cells demonstrated significant decrease in proliferation, viability, and survival. GE showed upregulation of PLK4 in rhabdoid tumors and other embryonal tumors of the brain. The PLK4 inhibitor CFI-400945 showed cytotoxic effects on rhabdoid tumor cell lines while sparing non-neoplastic human fibroblasts and developing zebrafish larvae.

Conclusions

Our findings indicate that rhabdoid tumor cell proliferation is highly dependent on PLK4 and suggest that targeting PLK4 with small-molecule inhibitors may hold a novel strategy for the treatment of MRT and possibly other embryonal tumors of the brain. This is the first time that PLK4 has been described as a potential target for both brain and pediatric tumors.

INTRODUCTION

Rhabdoid tumors are highly aggressive and therapy-resistant embryonal tumors. They can occur in a variety of anatomical sites and receive the generic name of malignant rhabdoid tumors (MRTs). Rhabdoid tumors were first described in the kidney, where they received the name of rhabdoid tumor of the kidney or RTK. It is now known that the most frequent primary location is the brain, where they are called atypical teratoid/rhabdoid tumors (AT/RTs). Rhabdoid tumors originating at all sites are recognized as the same entity due to their similar morphology, aggressive clinical behavior, and common genetic abnormalities.[1] Tumors originating from different locations share the same biologic and clinical characteristics; however, low overlap in gene expression (GE) of AT/RTs and RTK has been recently demonstrated.[2] Furthermore, pan-omics analyses have recently established that there are molecularly defined subgroups of tumors within rhabdoid tumors.[3-5] The large majority of rhabdoid tumors demonstrate genomic alterations of the SMARCB1 (INI1/BAF47/hSNF5) gene or, to a lesser extent, the SMARCA4 (BRG1) gene.[6] Both genes are components of the SWI/SNF chromatin-remodeling complex.[7]

AT/RTs are the most common malignant central nervous system (CNS) tumors of children below 6 months of age.[8] Approximately 70% of all cases arise in children younger than 1 year of age, and over 90% of cases occur before 3 years of age. Overall survival is poor, with median survival of about 17 months.[9] Recently, intensive multimodality treatment combining maximal safe surgery, craniospinal irradiation, and intensive chemotherapy has provided survival improvement. However, treatment-related toxicity is high. Moreover, young age and involvement of critical structures within the CNS limits the use of this approach.[8] Furthermore, over 70% of children with extracranial MRT express nonlocalized disease at the time of diagnosis and traditional chemotherapy is largely ineffective.[10] In this scenario, more effective and less toxic therapeutic options are needed.

Protein kinases are key regulators of cell function. They mediate most of the signal transduction in eukaryotic cells and coordinate the activity of multiple cellular processes including metabolism, transcription, cell cycle progression, cell movement, differentiation, and apoptosis. They direct the activity, localization, and overall function of many proteins by modifying protein activity, though adding phosphate groups to their substrate. [11]

The human kinome comprises at least 518 protein kinases, of which 478 belong to one superfamily whose catalytic domains are related in sequence.[11, 12] Mutations and dysregulation of protein kinases play causal roles in human disease, particularly cancer.[12, 13] Their involvement in multiple aspects of cell biology opens the possibility of developing agonists and antagonists for therapeutic use. In fact, a growing interest in developing orally active protein kinase inhibitors has led to the approval of several inhibitors for clinical use.[14]

We hypothesized that a systematic functional screening of the kinome will allow an accurate study of the kinase-dependent rhabdoid tumor phenotype and, therefore, have the potential to reveal new potential therapeutic targets.

To test this hypothesis, we used clustered regularly interspaced short palindromic repeats (CRISPR)/CRISPR-associated protein 9 (Cas9). The CRISPR/Cas9 system is a powerful gene-editing technology and recognized as "the biggest game changer to hit biology since PCR."[15] For gene editing, two components must be expressed in the cells: the Cas9 nuclease and a guide RNA (gRNA) that directs Cas9 to a specific target DNA site using standard RNA-DNA complementarity base pairing. After DNA binding, DNA double-strand breaks (DSBs) are created in the targeted area. These DSBs are then repaired by nonhomologous end joining, which frequently results in gene disruption.[16-20]

It has been shown that genome-wide screens can be accomplished with pools of lentivirus. Instead of a typical "pooled" screening approach, where gRNAs for multiple genes are delivered together, we used an "arrayed" screening approach focused in the kinome. Arrayed libraries of gRNAs in lentiviral expression constructs provide a potent delivery method for complete individual gene knockout. With this approach, each kinase gene is edited by individual transductions with up to four gRNAs that target the same gene in exons conserved across expressed isoforms.[21-23]

Methods

SMARCB1-Deficient Rhabdoid Tumor Cell Lines.

Figure 4B:
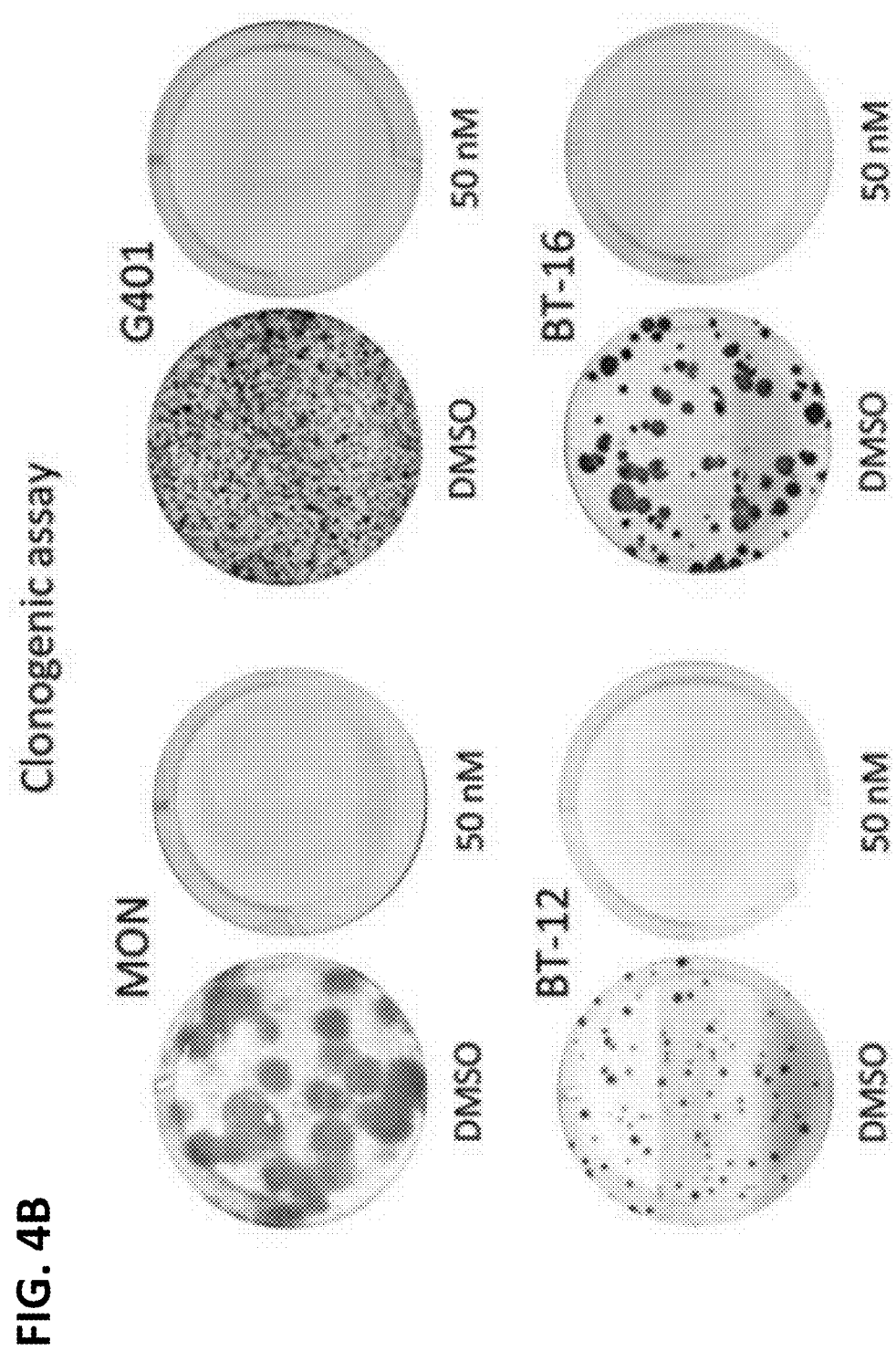
Figure 4C:
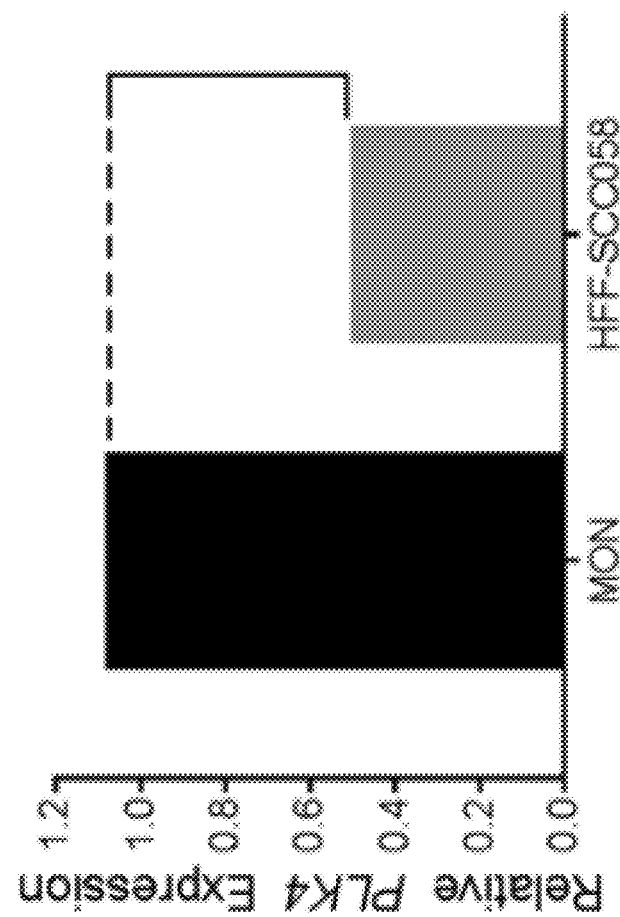

MON cells, provided by Dr. Delattre (Institute Curie, Paris, France), were established from an abdominal rhabdoid tumor.[24-26] The G401 cell line (ATCC, USA) was established from a RTK. AT/RT cell lines BT-12 and BT-16, which have been extensively used in preclinical studies,[27, 28] were established by Drs. Houghton and Biegel (Nationwide Children's Hospital, Columbus, Ohio, and The Children's Hospital of Philadelphia, Philadelphia, Pa., respectively) and provided to us by Dr. Hashizume (Northwestern University Feinberg School of Medicine, Chicago, Ill.).[29] As a negative control, we used HFF-SCC058 cells (EDM Millipore, USA) derived from human foreskin fibroblasts, which have significantly lower expression of Polo-like kinase 4 (PLK4) (FIG. 4C). MON, BT-12, and BT-16 cells were maintained in HyClone RPMI 1640 (GE Healthcare Life Sciences, USA), G401 in McCoy's 5A (Sigma—Aldrich, USA), and HFF-SCC058 in DMEM (Thermo Fisher Scientific, USA). All were supplemented with 10% fetal bovine serum and 1% penicillin/streptomycin at 37 C, 5% $CO_2$.

CRISPR Screening.

We performed a partial screening of the kinome by editing 160 kinase genes individually (Table 1) in MON cells using lentiviral CRISPR/Cas9 particles (Invitrogen™ LentiArray™ CRISPR Libraries, Thermo Fisher Scientific, USA) and validated our findings in two AT/RT and one RTK cell lines. For this, we used four types of lentivectors: (1) a lentivector to permanently express Cas9 with blasticidin-resistant gene, (2) a lentivector to express each gRNA with puromycin-resistant gene, (3) a positive control with gRNA for the HPRT gene, and (4) a negative control with scrambled gRNA. In order to maximize gene editing, gRNAs were designed to mutate all known isoforms of each target kinase gene with most of the target sequences encompassed in the 5' coding exons. In order to maximize the probability of generating indels in all isoforms of a given gene and to minimize off-target effects, an algorithm for the gRNA design was utilized.

We first stably expressed Cas9 protein in MON cells. The MON-expressing Cas9 (MON-Cas9) cells were then infected with each LentiArray-CRISPR-Kinase.

We plated 3,000 cells/well at 50-60% confluence and used 10 µg/ml of blasticidin for 7 days for Cas9 selection and 1 µg/ml of puromycin for 6 days for kinase gene selection. CRISPR-mutated cells for each one of the 160 individual kinase genes were monitored. Equal numbers of cells were plated to 12-well plates and the time to reach confluence was determined. Kinase mutations that most significantly impaired cell proliferation according to this criterion were selected for further investigation.

Gene Editing Evaluation by Gene Cleavage Detection.

Gene editing was evaluated by genome cleavage detection (GCD) assay using GeneArt® Genomic Cleavage Detection Kit (Thermo Fisher Scientific, USA), a method that detects locus-specific DSB formation by direct polymerase chain reaction (PCR) amplification and endonuclease activity that cuts specifically at hetero-duplex mismatches.

Gene Editing Evaluation by Next-Generation Sequencing.

Figure 1C:
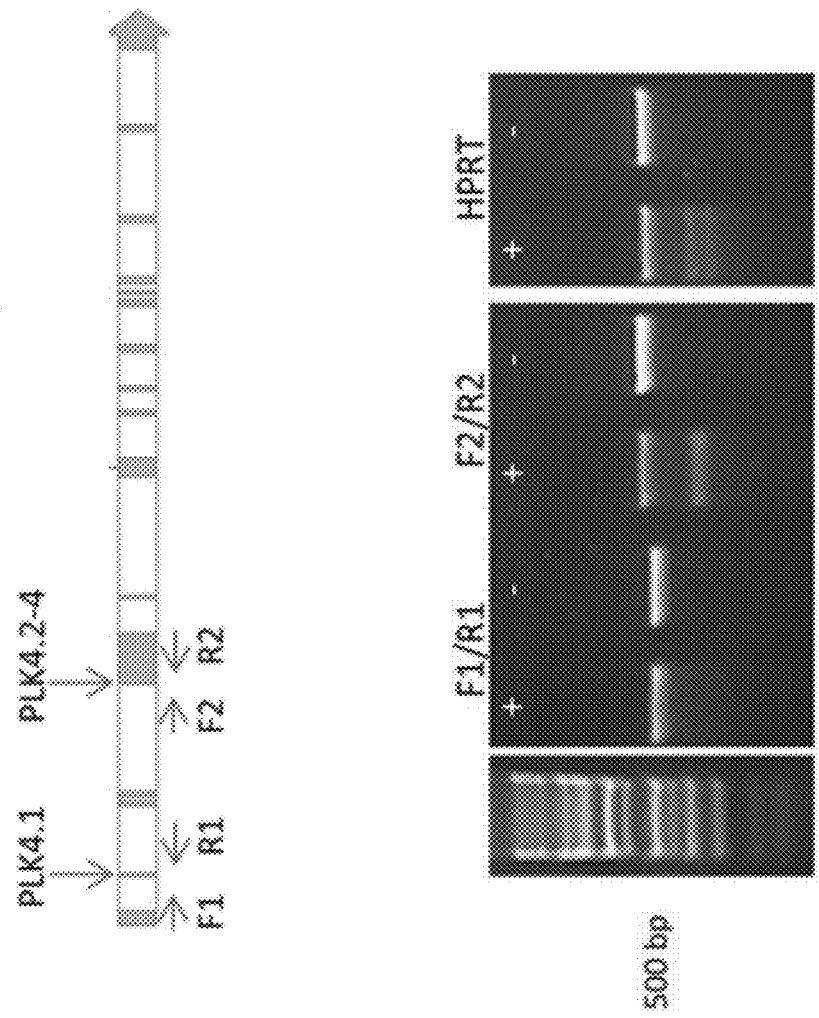
Figure 1D:
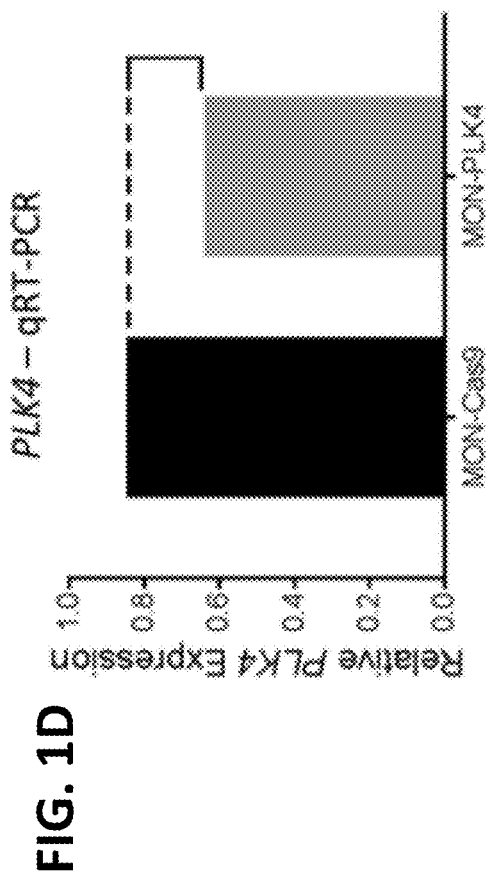

Evaluation of on-target and off-target cleavage for both MON-Cas9 and MON-PLK4-mutated cells was performed by next-generation sequencing (NGS) using the Ion Torrent PGM™ System (Thermo Fisher Scientific, USA). To evaluate the cleavage at the various PLK4 target sites (four PLK4 gRNAs: PLK4.1, PLK4.2, PLK4.3, and PLK4.4), AmpliSeq™ primers (Thermo Fisher Scientific, USA) were designed flanking each gRNA genomic target region (FIG. 1C). To evaluate possible off-target cleavage, potential off-target sequences were bioinformatically predicted using a CRISPR designer tool (Thermo Fisher Scientific, USA) and AmpliSeq™ primers were designed to amplify each predicted off-target region.

Microarray GE Profiling.

Fresh frozen tumor samples were provided by the Falk Brain Tumor Bank (Chicago, Ill., USA), the Center for Childhood Cancer, Biopathology Center (Columbus, Ohio, USA), which is a section of the Cooperative Human Tissue Network of The National Cancer Institute (Bethesda, Md., USA), and the Tumor Bank of the Children's Hospital at Westmead (Westmead, New South Wales, Australia). Written informed parental consents were obtained prior to sample collection. The study was approved by the institutional review board of Ann and Robert H. Lurie Children's Hospital of Chicago (IRB 2005-12252; 2005-12692; 2009-13778, and 2012-14887). A total of 116 samples were included in the study (Table 2). GE profiling was performed using Illumina HT-12v.4 BeadChip whole-genome expression arrays (Illumina, USA).[30]

Quantitative Real-Time PCR.

The expression of PLK4 (Hs00179514_m1) was verified by TaqMan GE assays (Thermo Fisher Scientific, USA) using the housekeeping gene GAPDH (Hs02758991_g1) as reference as previously described.[30] PLK4 inhibitor. The cytotoxic effects of the PLK4 inhibitor CFI-400945 (CAS1338800-06-8—Cayman Chemical, USA)[31-33] were tested in MON, G401, BT-12, and BT-16 cells. Cell proliferation was evaluated by MTT assay and cell survival was evaluated by clonogenic assays using increasing concentrations of the drug in different time-points, as described below.

Proliferation Evaluation by MTT Assay.

To evaluate cell proliferation, we used TACS MTT Cell Proliferation Assays (Trevigen, USA). We plated $2 \times 10^3$ cells on each well of a 96-well plate and the absorbance was measured after 48 and 72 hr at concentrations of 10, 50, 100, 200, and 500 nM. Each experiment was performed in triplicates.

Proliferation Evaluation by Flow Cytometry.

MON-Cas9 and MON-PLK4-mutated cells were evaluate for the impact of the mutation over the cell cycle by staining the cells with propidium iodide (Thermo Fisher Scientific, USA). Cells were then subjected to flow cytometric analysis using a BD Fortessa instrument (BD Biosciences, USA). Data was analyzed using Modfit LT from Verity Software House. Experiments were performed in triplicates.

Proliferation Evaluation by Immunohistochemistry.

Formalin-fixed paraffin-embedded 5-µm thick sections from cell blocks of MON-Cas9 and MON-PLK4-mutated cells were stained using standard immunohistochemical methods. For proliferation analysis, we evaluated Ki-67 and phospho-histone H3 (PHH3) immunostaining. Positive cells for Ki-67 and PHH3 were counted in five fields with 40× magnification using ImageJ software.[34]

Invasion and Migration Assays.

Both migration and invasion were assessed using a 24-well Transwell chamber system (Corning, USA).[35] MON cells were plated at 20,000 per well for cell migration and at 50,000 per well coated with matrigel (200 µg/ml, 3 hr of solidification) for cell invasion. HFF-SCC058 cells were used as negative controls. Cells were treated with either 100 nM of CFI-400945 or 0.1% dimethyl sulfoxide (DMSO), incubated for 24 hr, fixed with formalin, stained by Cresyl violet (ACROS Organics, USA), and counted using an inverted microscope. All experiments were performed in triplicates.

Clonogenic Assay.

For each cell line, 200 cells were seeded into six-well plates, incubated for 14 days, fixed with formalin, stained with Cresyl violet (ACROS Organics, USA), and the number of colonies counted using Image J software (www.imagej.nih.gov).

To evaluate the effect of the PLK4 mutation over cell survival, MON-PLK4-mutated cells were compared with MON-Cas9. For drug sensitivity, MON, G401, BT-12, and BT-16 cells were treated with 50, 100, and 200 nM of CFI-400945. Controls were treated with 0.1% DMSO. All experiments were performed in triplicates.

In Vivo Toxicity Assay.

The toxic effect of CFI-400945 to normal cells and to the whole organism was tested in wild type (NHGRI-1, ZDB-GENO-150204-3) zebrafish early larvae 2 days after fertilization. DMSO-dissolved CFI-400945 was added to the egg water to obtain seven concentrations of the drug (10, 50, 100 nM, 1, 5, 10, and 20 µM). Control larvae were exposed to 2% DMSO. Survival and delays in development and morphologic abnormalities were recorded at three time-points (24, 48, and 72 h of treatment). For each condition, groups of 20 larvae were analyzed in triplicates totalizing 420 subjects and 60 controls. Two-way ANOVA was used to analyze the results.

Results

Mutations in PLK4 Significantly Impaired Rhabdoid Tumor Cell Growth. A

We confirmed the initial screening results by repeating CRISPR editing of those eight kinase genes and controls. These secondary results were consistent with the initial observations with the same eight kinase-mutated cells taking at least twice as long as the controls to reach confluence.

PLK4 gRNAs Edited the PLK4 Gene with High Specificity.

We have performed an analysis of the off-target sites for all PLK4 gRNAs based on degenerate nucleotide sequences. Only 48 sites of high homology were identified in the genome, and only three of them were located within coding regions. NGS sequencing with primers specific for each site demonstrated lack of off-target cleavage at all sites (data not shown).

PLK4 is Overexpressed in MRTs, RTK, AT/RTs, and Other Embryonal Brain Tumors.

To explore the pattern of PLK4 expression in rhabdoid tumors, we evaluated the microarray GE data of our collection of 116 samples (Table 2). GE data from these microarray experiments have been previously validated by our group.[1, 30, 36]

Figure 2B:
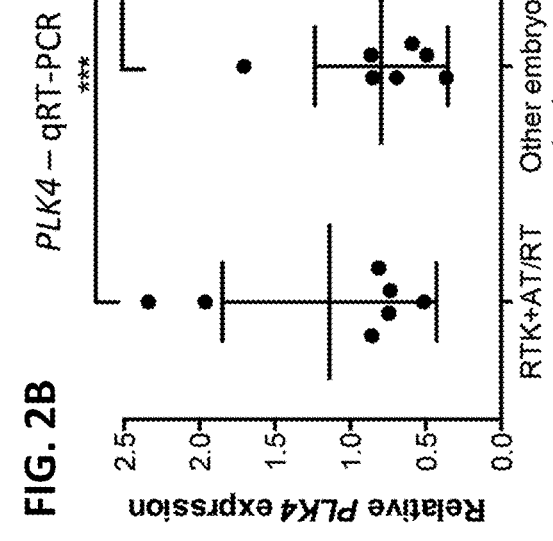
(FIG. 2B) PLK4 expression levels were validated by qRT-PCR ($*P<0.05$ and $*P<0.001$, one-way ANOVA).
Figure 2A:
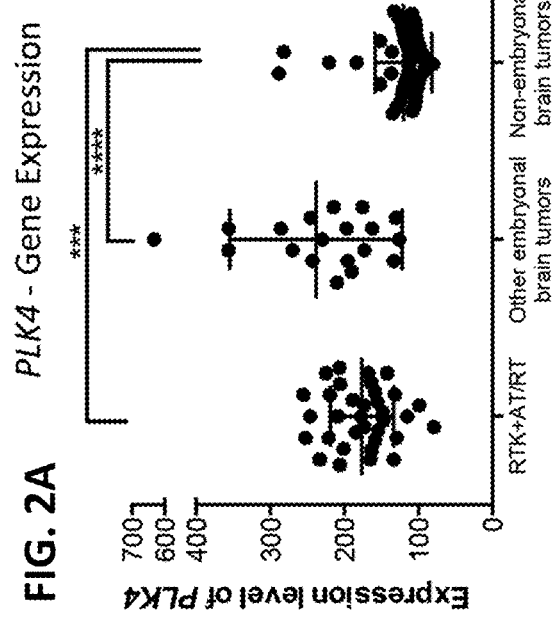
(FIG. 2A) Analysis of GE data showed overexpression of PLK4 in RTK, AT/RT, and other embryonal brain tumors, when compared with other pediatric brain tumor types and normal brain tissue.

Our analysis demonstrated overexpression of PLK4 in RTK, AT/RTs, and additional embryonal brain tumors, when compared with other pediatric brain tumor types and normal brain tissue (FIG. 2A). PLK4 expression was validated by qRT-PCR (FIG. 2B). While 33/34 rhabdoid tumors and 16/19 nonrhabdoid embryonal brain tumors demonstrated high expression of PLK4, only 2/42 gliomas and 2/16 nonglial tumors (a germinoma and a choroid plexus carcinoma) demonstrated higher levels of expression.

Figure 2D:
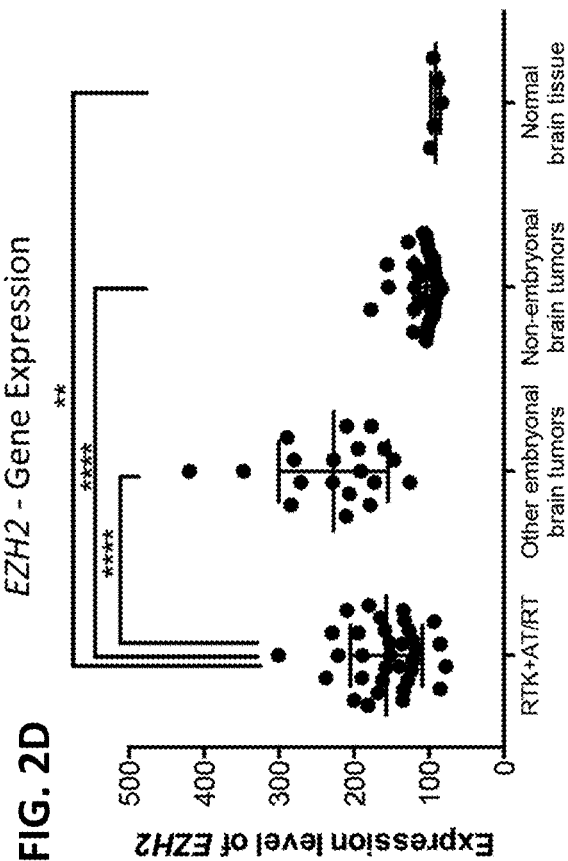
(FIG. 2C) Analysis of SMARCB1 GE (FIG. 2D) indicates downregulation in rhabdoid tumors and the analysis of EZH2 GE indicates upregulation in rhabdoid tumors ($P<0.01$.
Figure 2C:
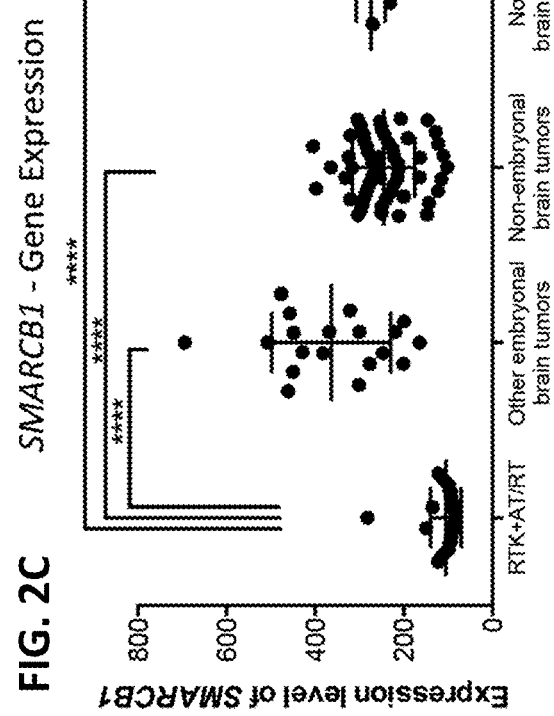

The highest level of expression among our samples was observed in an intracranial neuroblastoma (FIG. 2A and data not shown). SMARCB1 and EZH2, previously reported to be significantly differentially expressed in rhabdoid tumors (down- and upregulated, respectively),[6, 37] were evaluated in our cohort of samples as references (FIG. 2C and FIG. 2D).

PLK4 CRISPR-Mutated MON Cells Showed Decrease in Proliferation and Survival.

MON-PLK4-mutated cells compared to MON-Cas9 ones demonstrated (a) significantly lower proliferative activity as assessed by immunohistochemistry (IHC) for Ki-67 (FIG. 3A), by IHC for PHH3 (FIG. 3B), and by flow cytometry cell cycle analysis (FIG. 3C), and (b) significantly lower survival as detected by clonogenic assay (FIG. 3D).

The PLK4 Inhibitor CFI-400945 Demonstrated Cytotoxic Effects on MRTs, RTK, and AT/RT Cell Lines.

CFI-4000945 is a potent and highly selective PLK4 inhibitor.[31, 32, 38] Sampson et al. demonstrated that treatment with CFI-400945 resulted in cell death of breast cancer cells, while normal breast cells remained unaffected. [39]

Figure 4D:
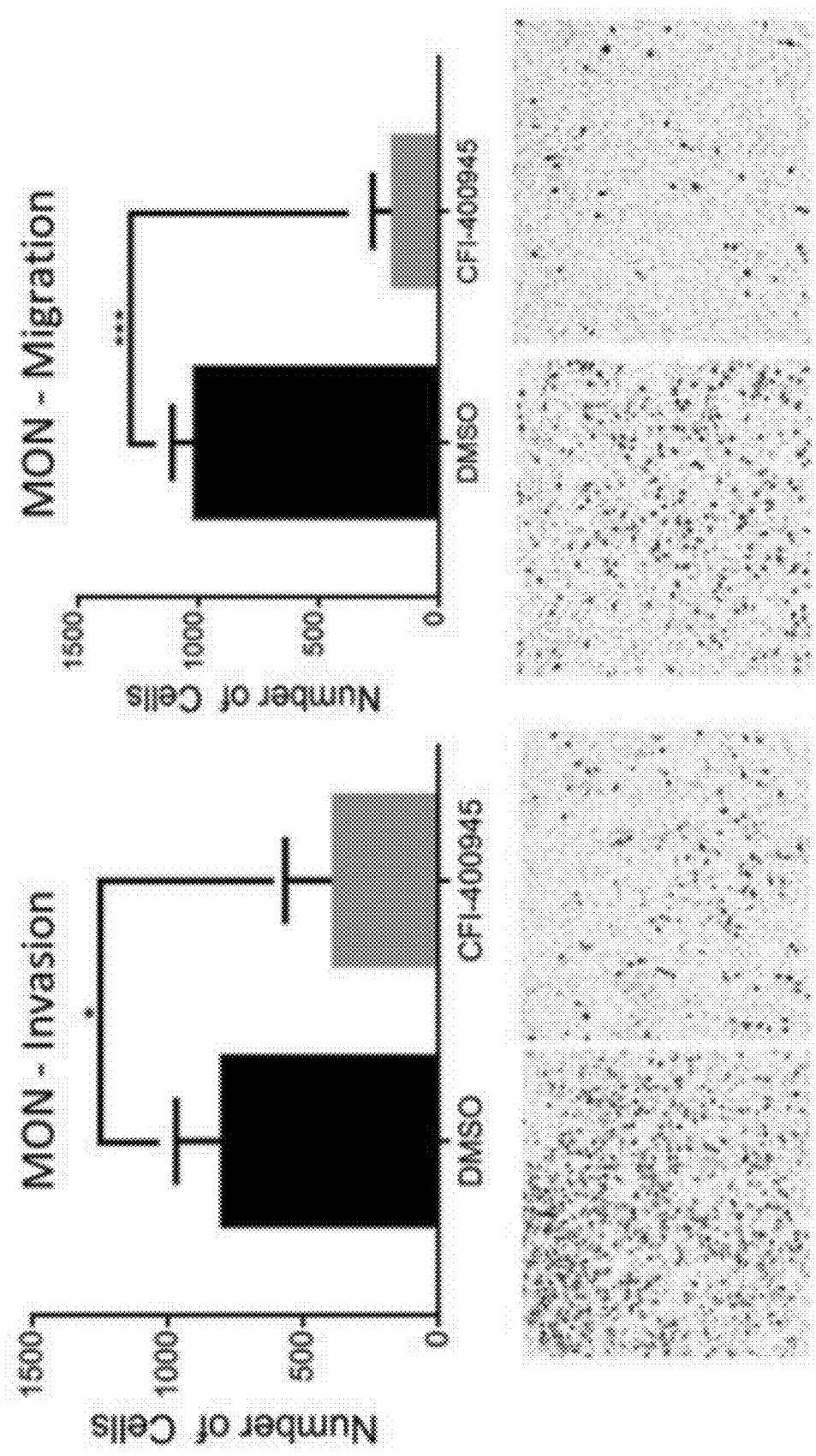
Figure 4E:
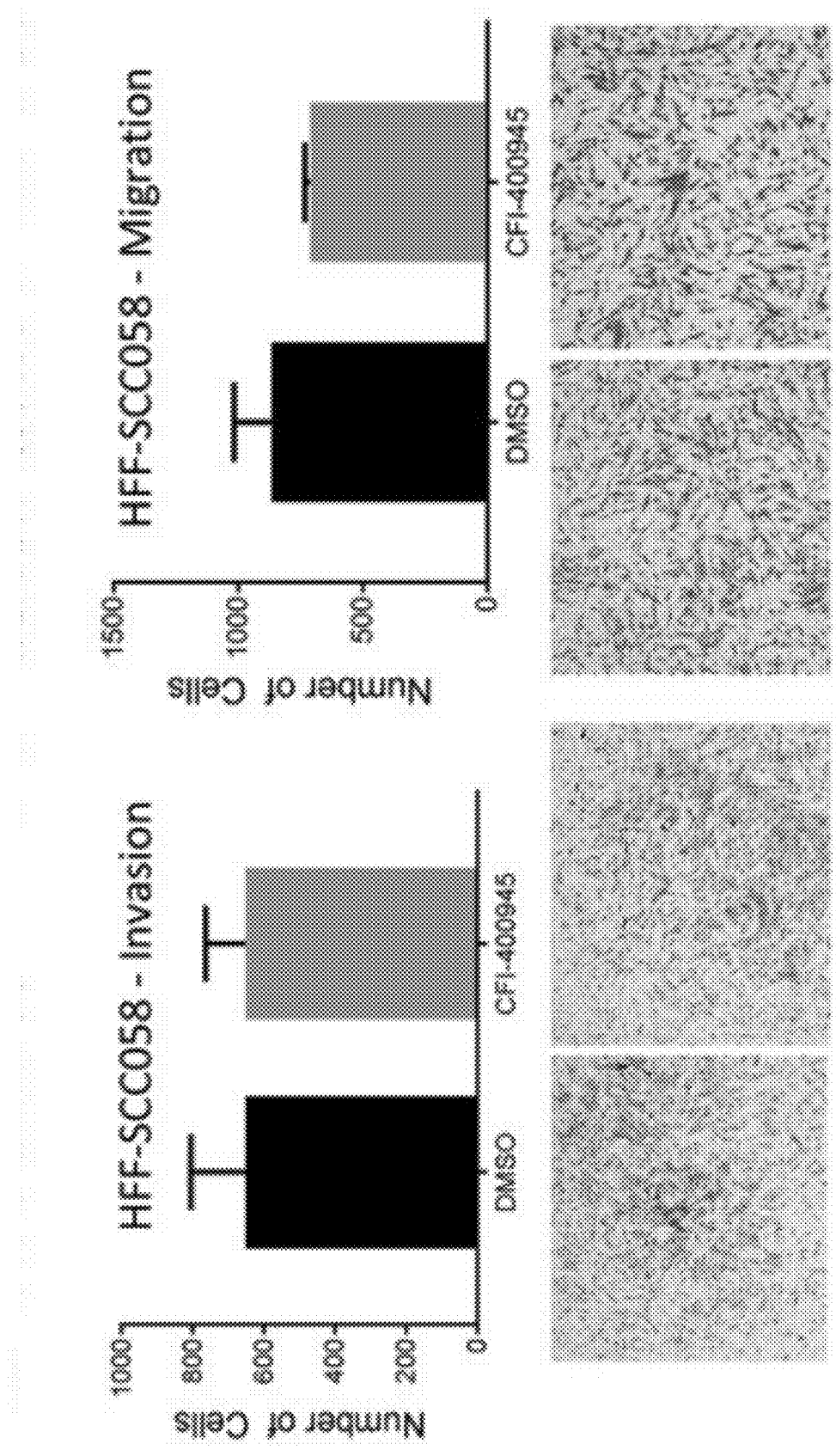

After determining the inhibitory concentration and treatment exposure time, we observed inhibitory effects of the drug in all tested cell lines. Treatment with the inhibitor resulted in significant impairment of cell proliferation (FIG. 4A) and reduction in cell survival (FIG. 4C). Remarkably, significant decrease in both cell migration and invasion was observed in MON-treated cells (FIGS. 4D and 4E). With a very low level of PLK4 expression detected by qRT-PCR (FIG. 4B), no effect was observed over HFF-SCC058 cells.

CFI-400945 Showed None to Minimal Toxic Effects Over Zebrafish Larvae.

PLK4 is highly conserved across species.[40] Comparison of zebrafish Plk4 sequence to human ortholog indicated a highly conserved kinase domain with fully preserved four amino acids predicted to bind CFI-400945 in PLK4 active site[32] (FIG. 5A). Such similarity indicates that zebrafish is a relevant model to test the effect of this drug on vertebrate development. We tested the toxicity of CFI-400945 at early larvae stage, when rapid organogenesis and growth take place, which is relevant for pediatric tumor therapy. After exposing over 400 larvae to a broad spectrum of drug concentration (10 nM to 20 µM) for 3 days, no increase in larvae deaths was observed. In extremely high concentrations (10 and 20 µM), edema and body curvature were consistently observed (FIG. 5B). These results demonstrated that although the drug penetrated the larvae, it may be safe for use in therapeutic doses.

DISCUSSION

In this study, we identified PLK4 as a new potential therapeutic target for rhabdoid tumors. The PLK family of serine/threonine kinases plays a critical role in regulation of mitosis. Mammalian cells express five Polo-kinase family members (PLK1-5). They share structurally similar amino-terminal catalytic domains and Polo-box motifs in the carboxy-terminal domains. PLK4 is structurally divergent from the other PLK family members. Unlike the other Polo-like kinases, PLK4 has only one Polo box and an active site with high homology to the Aurora kinases.

PLK4 plays a key role in cell cycle control. It localizes to the centrosomes and is a critical regulator of centriole duplication.[40-43] In normal conditions, PLK4 is expressed in proliferating tissues such as testis. Due to its essential role in cell proliferation, the activity of PLK4 is tightly autoregulated[44-46] as the correct number of centrosomes is critical for chromosome segregation during cell division. PLK4 has been described to be aberrantly expressed in cancer,[47-49] where centrosome amplification can promote abnormalities in spindle formation with subsequent abnormal chromosome segregation, resulting in aneuploidy and initiating carcinogenesis. Basto et al. demonstrated that centrosome amplification can initiate tumorigenesis in flies [47] and Ko et al. demonstrated that PLK4 haploinsufficiency significantly increased the incidence of spontaneous liver and lung cancers in adult mice.[48]

Sillibourne and Bornens demonstrated that the levels of active PLK4 increase toward the progression into the cell cycle. These levels are mirrored by the PLK4 mRNA levels, indicating that transcription has an important role in controlling the overall expression levels of active PLK4.[40] Our GE data show significantly higher PLK4 expression in both AT/RT and RTK when compared with nonembryonal pediatric brain tumors and normal brain tissue. This finding suggests that PLK4 overexpression is a common characteristic of rhabdoid tumors and independent of the tumor's site of origin. Remarkably, our data indicate that other embryonal tumors of the brain also overexpress PLK4. In our cohort of samples (Table 2), nonembryonal brain tumors including highly proliferative ones have very low PLK4 expression, suggesting that overexpression of PLK4 is not a direct function of tumor proliferation, but it is possibly linked to the embryonal nature of the tumors evaluated. Importantly, even in tumors with higher PLK4 expression, the overall expression levels of PLK4 is low, meaning that slight changes in expression may have significant impact over the phenotype. This is the first time PLK4 has been described as a potential target for both brain and pediatric tumors.

Kinase inhibition has already shown to be promising in the treatment of rhabdoid tumors.[8] Inhibition of ERBB2 by lapatinib resulted in significant impairment of cell migration and initiation of apoptosis in rhabdoid tumor cell lines.[28, 50] Palbociclib, an inhibitor of the cyclin-dependent kinases 4 and 6, delayed the regrowth of irradiated AT/RT xenografts. [51]

The proto-oncogene PLK1 is the most studied member of the PLK family. Morozov et al. observed that knocking down PLK1, which was shown to be downregulated in rhabdoid cells after SMARCB1 reintroduction, resulted in mitotic arrest, aberrant nuclear division, decreased survival, and induction of apoptosis.[52] Morozov et al. also showed that reintroduction of SMARCB1 into rhabdoid tumor cells resulted in repression of mitotic genes including Aurora kinase A (AURKA).[52] Later on, it was demonstrated that AURKA was a repressed effector target of SMARCB1, which repressed AURKA transcription in a cell-type-specific manner.[53] Notably, inhibition of AURKA resulted in decreased activity of pro-proliferative signaling pathways in AT/RT,[54] and treatment with the AURKA inhibitor alisertib resulted in high response rates in rhabdoid mouse xenograft models.[55] The AURKA inhibitor alisertib has shown to be active as a single agent in children with recurrent AT/RT,[56] and it is currently in phase II trial for rhabdoid tumor treatment.

The CFI-400945 is the first potent PLK4 inhibitor discovered. It has been demonstrated that CFI-400945 selectively inhibits PLK4 in cancer cells, and it has recently entered in phase I clinical trials for the treatment for solid tumors in adults. It has been observed that this drug had "certain activity" against Aurora kinase B due to structural similarities of their active binding sites. However, the drug exhibited no significant inhibition of AURKA or of other PLK family members.[32, 33]

Here, we first demonstrated that editing of PLK4 resulted in significant impairment of proliferation and survival of MRT (MON) cells. Then, we investigated the cytotoxic activity of the PLK4 inhibitor CFI-400945 over AT/RT, MRT, RTK and MB cells. We verified that the use of the drug, even in low concentrations, resulted in significant impact on tumor cell proliferation and survival. We now speculate that association of PLK4 inhibitor with AURKA inhibitor might be a beneficial combination treatment for patients with rhabdoid tumors.

Recently, Rosario et al. demonstrated that PLK4 is also involved in regulating cell spreading and motility promoting cell migration and may, therefore, be associated with cancer progression and death from metastasis in solid tumor patients.[41] Remarkably, we also demonstrated that CFI-400945 significantly impaired rhabdoid tumor cell migration and invasion while sparing non-neoplastic human fibroblasts. This is additional evidence that inhibiting PLK4 may be a path to successfully treat these highly metastatic pediatric tumors.

Finally, as our main target is the pediatric population, we tested the toxicity of CFI-400945 to the zebrafish development by exposing zebrafish larvae to increasing concentrations of the drug for extended periods of time. We observed that no embryo died from the effect of the drug, while extremely high concentrations resulted in edema. Based on our observations and on data from the literature, we infer that only cells abnormally expressing PLK4 cells are susceptible to the effects of the inhibitor and therefore it may be safe to be used in pediatric patients. The mechanisms by which the PLK4 inhibitor seems to spare normal cells are still to be elucidated.

Conclusions

Our findings indicate that embryonal tumor cell proliferation is dependent on PLK4, as shown by genetic and pharmacologic intervention. This suggests that PLK4 may function as a therapeutic target for MRT, RTK, AT/RT, and possibly other embryonal tumors of the brain, including MB.

REFERENCES (EXAMPLE 1)

1. Grupenmacher A T, Halpern A L, Bonaldo Mde F, et al. Study of the gene expression and microRNA expression profiles of malignant rhabdoid tumors originated in the brain (AT/RT) and in the kidney (RTK). Child's Nery Syst. 2013; 29(11):1977-1983.
2. Birks D K, Donson A M, Patel P R, et al. Pediatric rhabdoid tumors of kidney and brain show many differences in gene expression but share dysregulation of cell cycle and epigenetic effector genes. Pediatr Blood Cancer. 2013; 60(7):1095-1102.
3. Johann P D, Erkek S, Zapatka M, et al. Atypical teratoid/rhabdoid tumors are comprised of three epigenetic subgroups with distinct enhancer landscapes. Cancer Cell. 2016; 29(3):379-393.
4. Chun H J, Lim E L, Heravi-Moussavi A, et al. Genome-wide profiles of extra-cranial malignant rhabdoid tumors reveal heterogeneity and dysregulated developmental pathways. Cancer Cell. 2016; 29(3):394-406.
5. Torchia J, Picard D, Lafay-Cousin L, et al. Molecular subgroups of atypical teratoid rhabdoid tumours in children: an integrated genomic and clinicopathological analysis. Lancet Oncol. 2015; 16(5):569-582.
6. Sredni S T, Tomita T. Rhabdoid tumor predisposition syndrome. Pediatr Dev Pathol. 2015; 18(1):49-58.
7. Muchardt C, Yaniv M. The mammalian SWI/SNF complex and the control of cell growth. Semin Cell Dev Biol. 1999; 10(2):189-195.\
8. Fruhwald M C, Biegel J A, Bourdeaut F, et al. Atypical teratoid/rhabdoid tumors-current concepts, advances in biology, and potential future therapies. Neuro-oncology. 2016; 18(6):764-778.
9. Ginn K F, Gajjar A. Atypical teratoid rhabdoid tumor: current therapy and future directions. Front Oncol. 2012; 2:114.
10. Gadd S, Sredni S T, Huang C C, et al. Rhabdoid tumor: gene expression clues to pathogenesis and potential therapeutic targets. Lab Invest. 2010; 90(5):724-738.
11. Manning G, Whyte D B, Martinez R, et al. The protein kinase complement of the human genome. Science. 2002; 298(5600):1912-1934.

12. Fleuren E D, Zhang L, Wu J, et al. The kinome 'at large' in cancer. Nat Rev Cancer. 2016; 16(2):83-98.
13. Fedorov O, Muller S, Knapp S. The (un)targeted cancer kinome. Nat Chem Biol. 2010; 6(3):166-169.
14. Cohen P. Protein kinases—the major drug targets of the twenty-first century? Nat Rev Drug Discov. 2002; 1(4): 309-315.
15. Ledford H. CRISPR, the disruptor. Nature. 2015:522 (7554):20-24.
16. Sander J D, Joung J K. CRISPR—Cas systems for editing, regulating and targeting genomes. Nat Biotechnol. 2014; 32(4):347-355.
17. Cho S W, Kim S, Kim J M, et al. Targeted genome engineering in human cells with the Cas9 RNA-guided endonuclease. Nat Biotechnol. 2013; 31(3):230-232.
18. Jiang W, Bikard D, Cox D, et al. RNA-guided editing of bacterial genomes using CRISPR-Cas systems. Nat Biotechnol. 2013; 31(3):233-239.
19. Jinek M, Chylinski K, Fonfara I, et al. A programmable dual-RNA-guided DNA endonuclease in adaptive bacterial immunity. Science. 2012; 337(6096):816-821.
20. Mali P, Yang L, Esvelt K M, et al. RNA-guided human genome engineering via Cas9. Science. 2013; 339(6121): 823-826.
21. Shalem O, Sanjana N E, Hartenian E, et al. Genome-scale CRISPR-Cas9 knockout screening in human cells. Science. 2014; 343(6166):84-87.
22. Wang T, Wei J J, Sabatini D M, et al. Genetic screens in human cells using the CRISPR-Cas9 system. Science. 2014; 343(6166):80-84.
23. Zhou Y, Zhu S, Cal C, et al. High-throughput screening of a CRISPR/Cas9 library for functional genomics in human cells. Nature. 2014; 509(7501):487-491.
24. Zhang Z K, Davies K P, Allen J, et al. Cell cycle arrest and repression of cyclin D1 transcription by INI1/hSNF5. Mol Cell Biol. 2002; 22(16):5975-5988.
25. Albanese P, Belin M F, Delattre O. The tumour suppressor hSNF5/INI1 controls the differentiation potential of malignant rhabdoid cells. Eur J Cancer. 2006; 42(14): 2326-2334.
26. Versteege I, Medjkane S, Rouillard D, et al. A key role of the hSNF5/INI1 tumour suppressor in the control of the G1-S transition of the cell cycle. Oncogene. 2002; 21(42): 6403-6412.
27. Alimova I, Birks D K, Harris P S, et al. Inhibition of EZH2 suppresses self-renewal and induces radiation sensitivity in atypical rhabdoid teratoid tumor cells. Neuro-oncology. 2013; 15(2):149-160.
28. Singh A, Lun X, Jayanthan A, et al. Profiling pathway-specific novel therapeutics in preclinical assessment for central nervous system atypical teratoid rhabdoid tumors (CNS ATRT): favorable activity of targeting EGFR-ErbB2 signaling with lapatinib. Mol Oncol. 2013; 7(3): 497-512.
29. Hashizume R, Gupta N, Berger M S, et al. Morphologic and molecular characterization of ATRT xenografts adapted for orthotopic therapeutic testing. Neuro-oncology. 2010; 12(4):366-376.
30. Sredni S T, Huang C C, Pundy T, et al. A gene signature for a long-term survivor of an atypical teratoid/rhabdoid tumor. Cancer Genet. 2014; 207(9):420-424.
31. Sampson P B, Liu Y, Forrest B, et al. The discovery of polo-like kinase 4 inhibitors: identification of (1R,2S).2-(3-((E).4-(((cis).2,6-dimethylmorpholino)methyl)styryl). 1H.indazol-6-yl)-5'-methoxyspiro[cyclopropane-1,3-'-indolin]-2'-one (CFI-400945) as a potent, orally active antitumor agent. J Med Chem. 2015; 58:147-169.
32. Mason J M, Lin D C, Wei X, et al. Functional characterization of CFI-400945, a Polo-like kinase 4 inhibitor, as a potential anticancer agent. Cancer Cell. 2014; 26(2): 163-176.
33. Yu B, Yu Z, Qi P P, et al. Discovery of orally active anticancer candidate CFI-400945 derived from biologically promising spirooxindoles: success and challenges. Eur J Med Chem. 2015; 95:35-40.
34. Schneider C A, Rasband W S, Eliceiri K W. NIH Image to ImageJ: 25 years of image analysis. Nat Methods. 2012; 9(7):671-675.
35. Zheng B, Liang L, Huang S, et al. MicroRNA-409 suppresses tumour cell invasion and metastasis by directly targeting radixin in gastric cancers. Oncogene. 2012; 31(42):4509-4516.
36. Suzuki M, Kondo A, Ogino I, et al. Overexpression of TEAD4 in atypical teratoid/rhabdoid tumor: new insight to the pathophysiology of an aggressive brain tumor. Pediatr Blood Cancer. 2016; 00:1-10, DOI: 10.1002/pbc.26398.
37. Kim K H, Kim W, Howard T P, et al. SWI/SNF-mutant cancers depend on catalytic and non-catalytic activity of EZH2. Nat Med. 2015; 21(12):1491-1496.
38. Sampson P B, Liu Y, Patel N K, et al. The discovery of Polo-like kinase 4 inhibitors: design and optimization of spiro[cyclopropane-1,3'[3H]indol]-2'(1'H). ones as orally bioavailable antitumor agents. J Med Chem. 2015; 58(1): 130-146.
39. Sampson P B, Liu Y, Forrest B, et al. The discovery of Polo-like kinase 4 inhibitors: identification of (1R,2S),2-(3-((E).4-(((cis).2,6-dimethylmorpholino)methyl)styryl). 1H-indazol-6-yl)-5'-methoxyspiro[cyclopropane-1,'-indolin]-2'-one (CFI-400945) as a potent, orally active antitumor agent. Journal of medicinal chemistry. 2015; 58(1):147-169.
40. Sillibourne J E, Bornens M. Polo-like kinase 4: the odd one out of the family. Cell Div. 2010; 5:25.
41. Rosario C O, Kazazian K, Zih F S, et al. A novel role for Plk4 in regulating cell spreading and motility. Oncogene. 2015; 34(26):3441-3451.
42. Bettencourt-Dias M, Rodrigues-Martins A, Carpenter L, et al. SAK/PLK4 is required for centriole duplication and flagella development. Curr Biol. 2005; 15(24):2199-2207.
43. Habedanck R, Stierhof Y D, Wilkinson C J, et al. The Polo kinase Plk4 functions in centriole duplication. Nat Cell Biol. 2005; 7(11):1140-1146.
44. Holland A J, Lan W, Niessen S, et al. Polo-like kinase 4 kinase activity limits centrosome overduplication by auto-regulating its own stability. J Cell Biol. 2010; 188(2):191-198.
45. Holland A J, Cleveland D W. Polo-like kinase 4 inhibition: a strategy for cancer therapy? Cancer Cell. 2014; 26(2):151-153.
46. Sillibourne J E, Tack F, Vloemans N, et al. Autophosphorylation of polo-like kinase 4 and its role in centriole duplication. Mol Biol Cell. 2010; 21(4):547-561.
47. Basto R, Brunk K, Vinadogrova T, et al. Centrosome amplification can initiate tumorigenesis in flies. Cell. 2008; 133(6):1032-1042.
48. Ko M A, Rosario C O, Hudson J W, et al. Plk4 haploinsufficiency causes mitotic infidelity and carcinogenesis. Nat Genet. 2005; 37(8):883-888.
49. Liu L, Zhang C Z, Cai M, et al. Downregulation of polo-like kinase 4 in hepatocellular carcinoma associates with poor prognosis. PLoS ONE. 2012; 7(7):e41293.
50. Sredni S T, Patel K, D'Almeida Costa F, et al. Activation of ErbB2-ErbB3 signaling pathway supports potential therapeutic activity of ErbB inhibitors in AT/RT. J Neuro-oncol. 2014; 118(1):201-203.
51. Hashizume R, Zhang A, Mueller S, et al. Inhibition of DNA damage repair by the CDK4/6 inhibitor palbociclib delays irradiated intracranial atypical teratoid rhabdoid tumor and glioblastoma xenograft regrowth. Neuro-oncology. 2016; 18(11):1519-1528.
52. Morozov A, Lee S J, Zhang Z K, et al. INI1 induces interferon signaling and spindle checkpoint in rhabdoid tumors. Clin Cancer Res. 2007; 13(16):4721-4730.
53. Lee S, Cimica V, Ramachandra N, et al. Aurora A is a repressed effector target of the chromatin remodeling protein INI1/hSNF5 Required for Rhabdoid Tumor Cell Survival. Cancer Res. 2011; 71(9):3225-3235.
54. Venkataraman S, Alimova I, Tello T, et al. Targeting Aurora kinase A enhances radiation sensitivity of atypical teratoid rhabdoid tumor cells. J Neuro-oncol. 2012; 107(3):517-526.
55. Maris J M, Morton C L, Gorlick R, et al. Initial testing of the aurora kinase A inhibitor MLN8237 by the Pediatric Preclinical Testing Program (PPTP). Pediatr Blood Cancer. 2010; 55(1):26-34.
56. Wetmore C, Boyett J, Li S Y, et al. Alisertib is active as single agent in recurrent atypical teratoid rhabdoid tumors in 4 children. Neuro-oncology. 2015; 17(6):882-888.

Example 2—Inhibition of Polo-Like Kinase 4 (PLK4): A New Therapeutic Option for Rhabdoid Tumors and Pediatric Medulloblastoma Reference is made to Sredni et al., "Inhibition of polo-like kinase 4 (PLK4): a new therapeutic option for rhabdoid tumors and pediatric medulloblastoma," Oncotarget, 2017, Vol. 8, (No. 67), pp: 111190-111212, the content of which is incorporated herein by reference in its entirety.

Abstract

Rhabdoid tumors (RT) are highly aggressive and vastly unresponsive embryonal tumors. They are the most common malignant CNS tumors in infants below 6 months of age. Medulloblastomas (MB) are embryonal tumors that arise in the cerebellum and are the most frequent pediatric malignant brain tumors. Despite the advances in recent years, especially for the most favorable molecular subtypes of MB, the prognosis of patients with embryonal tumors remains modest with treatment related toxicity dreadfully high. Therefore, new targeted therapies are needed.

The polo-like kinase 4 (PLK4) is a critical regulator of centriole duplication and consequently, mitotic progression. We previously established that PLK4 is overexpressed in RT and MB. We also demonstrated that inhibiting PLK4 with a small molecule inhibitor resulted in impairment of proliferation, survival, migration and invasion of RT cells.

Here, we showed in MB the same effects that we previously described for RT. We also demonstrated that PLK4 inhibition induced apoptosis, senescence and polyploidy in RT and MB cells, thereby increasing the susceptibility of cancer cells to DNA-damaging agents. In order to test the hypothesis that PLK4 is a CNS druggable target, we demonstrated efficacy with oral administration to an orthotropic xenograft model.

Based on these results, we postulate that targeting PLK4 with small-molecule inhibitors could be a novel strategy for the treatment of RT and MB and that PLK4 inhibitors (PLK4i) might be promising agents to be used solo or in combination with cytotoxic agents.

INTRODUCTION

Rhabdoid tumors (RT), or malignant rhabdoid tumors (MRT), are among the most aggressive and lethal forms of human cancer. They can arise in any location in the body but are most commonly observed in the central nervous system (CNS), where they are called atypical teratoid/rhabdoid tumors (AT/RT). When arising in the kidneys they are called rhabdoid tumors of the kidney (RTK) while extracranial extrarenal rhabdoid tumors are generically called eMRT. Independent of their site of origin, RT are recognized as the same entity [1] with the vast majority showing loss of function of the SMARCI31 gene or, to a lesser extent, the SMARCA4 gene, both members of the SWUSNF chromatin-remodeling complex [2]. RT occurs predominantly in infants and children less than 3 years of age and although considered to be rare, AT/RT is the most common malignant tumor of infants below 6 months of age [3] The overall survival is poor with median survival around 17 months [4]. Introduction of anthracycline-containing chemotherapy regimens resulted in survival improvement, however with significant morbidity [5]. Radiation is also an effective component of therapy but needs to be avoided in patients younger than 3 years of age due to long term neurocognitive sequelae. Recently, investigations of altered signaling pathways have yielded a whole array of compounds with potential therapeutic activity, some of which are currently in clinical trials, including AURKA, EZH2 and CDK4/6 inhibitors [3]. However, despite the advances in recent years, the overall survival of these young patients remains poor and treatment related toxicity, high.

Medulloblastoma (MB) is an embryonal tumor of the cerebellum which is the most common malignant brain tumor in children and a major cause of mortality in pediatric oncology. Molecular studies from several groups around the world demonstrated that MB consists of four distinct molecular subgroups: WNT, Sonic Hedgehog (SHH), group 3, and group 4. Each subgroup differs in demographics, transcriptomes, somatic genetic events, and clinical outcomes [6, 7]. Regardless, current therapies for MB consist mostly of cytotoxic agents and mortality is still significant, with survivors exhibiting treatment-related effects as a consequence of cytotoxic chemotherapy and radiation [8].

Clearly, new targeted therapies are urgently needed. Our long-term goal is to identify new, more effective and less toxic anticancer therapies for RT and other pediatric embryonal tumors. In this regard, we previously demonstrated that RT cell proliferation is dependent on PLK4 and suggested that PLK4 is a candidate target for the treatment of RT and possibly other embryonal tumors. We accomplished this by performing a functional screening of the kinome to investigate essential kinases for RT proliferation. We used lentiviral CRISPR/Cas9 particles (Invitrogen™ LentiArray™ CRISPR Libraries, Thermo Fisher Scientific, USA) to individually mutate 160 kinases representing every major branch of the kinome. Mutations in the polo-like kinase 4 (PLK4) gene resulted in the most significant impairment of RT cell proliferation. We also established that the PLK4 inhibitor (PLK4i) CFI-400945 had in vitro therapeutic effects on RT cells [9] and detected PLK4 overexpression in pediatric MB [10].

The drug candidate CFI-400945 used in our previous studies is an effective PLK4 inhibitor [II, 12] and recently entered a phase I clinical trial to establish its safety, tolerability and pharmacokinetics in advanced solid tumors in adults (NCT01954316). Preliminary results indicated that the drug is "well tolerated at doses up to 72 ma and has a favorable PK profile" [13]. PLK4 plays a key role in cell cycle control. It localizes to the centrosomes, being a critical regulator of centriole duplication and consequently, mitotic progression [14-17]. The proposed role of PLK4 in the regulation of cytokinesis and maintenance of chromosomal stability is consistent with a function in cancer, as centrosome amplification can drive genetic instability with a resultant, impact on tumorigenesis. Consistent with our results in RT cells, PLK4 is overexpressed in human gastric [18], breast [11] and pancreatic cancer [19]. Therefore, there is an evolving trend of PLK4 up-regulation in diverse cancers and promising responses to treatment of such tumors with PLK4 inhibitor drug candidates such as CFI-400945. However, little is known about CFI-400945 in CNS tumors. Further, its molecular properties place it at the cusp of key multi-property profiles that characterize drugs with known in vivo blood brain barrier (BBB) penetrance sufficient for brain target engagement [20]. Therefore, we explored the potential of CFI-400945 to be an in vivo candidate for brain tumors such as AT/RT and gain insight into its molecular selectivity in the kinome target family.

We report here that MB cell lines derived from molecular subgroups with the most aggressive behavior (DAOY—from sonic hedgehog and D283—from groups 3/4) [21] were susceptible to the PLK4i CFI-400945 which impaired cell proliferation, cell viability, colony formation, migration and invasion, and induced polyploidy and senescence in these cells. We further illustrate the mechanism of action of the PLK4 inhibitor in these embryonal tumors. In order to extend our hypothesis to the in vivo context, we examined the efficacy of CFI-400945 in orthotropic AT/RT xenografts. Based on the results, we conclude that this PLK4 inhibitor can increase the susceptibility of embryonal cancer cells to DNA-damaging agents due to its role in the initiation and maintenance of polyploidy. Further, we suggest that the next generation of brain tumor focused PLK4 inhibitors could be promising agents for use in combination therapies for the treatment of RT and MB.

Results

Medulloblastoma (MB) Cells were Susceptible to the Therapeutic Effects of the PLK4 Inhibitor.

We previously demonstrated that PLK4 was overexpressed in RT and other embryonal tumors of the brain, including MB [9, 10]. We then demonstrated that RT cell proliferation is dependent on PLK4 and that PLK4 inhibitors may represent a novel therapeutic approach for these aggressive and unresponsive tumors. Now, we demonstrated that the MB cell lines DAOY and D283, representative of the most aggressive MB molecular subtypes (sonic hedgehog and groups 3/4, respectively) [21] are also susceptible to the PLK4i CFI-400945 (FIG. 6). Then, we provided additional evidence of the potential therapeutic effects of CH-400945 by demonstrating its effect on cell viability and the rate of the cells to reach confluency in 4 different cell lines, including RT originating in different locations (MON-soft tissue, G401-kidney, BT-12-brain) and in the DAOY MB cell lines (FIG. 7).

The PLK4 Inhibitor CFI-400945 is a Multi-Kinase Inhibitor with a Defined Selectivity.

Kinase screening profile revealed 10 kinases, including PLK4, in which activity was inhibited above 80% by CFI-400945. IC50 values were determined by a 10-point titration curve analysis. The inhibited kinases within these parameters were: PLK4—100%, IC50 4.85 nM; AURKB—95%, IC50 70.7 nM; AURKC—84%, IC50 106 nM; DDR2—100%, IC50 3156M; MUSK—96%, IC50 48.7 nM; NTRK1—92%, IC50 20.6 nM; NTRK2—96%, IC50 10.6 nM; NTRK3—96%, IC50 9.04 nM; ROS1—98% and TEK—96%, IC50 109 nM. The activity of aurora kinase A was inhibited by 60% (AURKA—60%, IC50 188 nM) (data not shown). CFI-400945 has a defined set of potential kinase targets that are logical contributors to its known phenotypic effects, with PLK4 in the higher affinity group, consistent with the prevailing view that kinase targets with IC50<1,000 nM are likely in vivo targets and a selective multi-kinase profile is needed for efficacy [22].

Key Features of the PLK4 Inhibitor CFI-400945 Suggest a Potential for Lower Cardio Toxicity or Drug-Drug Interaction Risk.

Screening of drug candidates for hERG potassium channel inhibition has become an early step in testing for potential drug dependent long QT syndrome that is linked to sudden death [23]. Binding of CFI-400945 at the hERG channel was not detected under standard assay procedures at the highest concentration tested (IC50>500 nM), while the IC50 value for the positive control E-4031 was 35.1 nM (data not shown). These data suggest that CFI-400945 is not in the high risk category for cardiovascular risk, although the FDA recommended in vivo cardiovascular toxicology would be required for investigational new drug status.

Cytochrome P450 (CYP450) enzymes are drivers of first-pass metabolism for orally administered drugs, with certain CYPs being known pharmacogenetic contributors to individual variance in drug safety and efficacy and others contributing to undesired drug-drug or drug-food interactions, that can contribute to toxicities or therapeutic failures [24]. Although there are more than 50 CYP isoenzymes, 90% of drugs are metabolized by 6 isoenzymes with the two of the most significant in risk being CYP3A4 and CYP2D6. CFI-400945 showed an IC50 value >500 nM (the highest tested concentration) for the isoenzymes recommended for testing by FDA guidance except for 3A4 BOMCC, which had an IC50 of 413 nM in contrast to 3.16 nM for the CYP3A4 canonical control substrate ketoconazole (positive controls were used for each isoenzyme tested) (data not shown). These results forecast lower risk category for multi-drug treatments in experiments or patients.

Inhibition of PLK4 Resulted in Abnormalities of Centriole Duplication and Transcript Expression.

The MON rhabdoid tumor cell line treated with the PLK4i CFI-400945 demonstrated abnormalities in centriole duplication. An increase in centriole numbers was observed when treating each cell line with a lower concentration (100 nM) for 48 hours, as demonstrated by immunofluorescence for gamma-tubulin. At a higher concentration of the PLK4i (500 nM), we observed significant decrease in centriole number. A decrease in PLK4 transcript expression was also detected by qRT-PCR in MON cells treated with increasing concentrations of the drug over time. A similar response was observed in additional RT and MB cell lines, but not in non-neoplastic human fibroblast that do not overexpress PLK4 [9] (FIG. 8).

Cells Treated with the PLK4 Inhibitor Underwent Apoptosis or Senescence.

Rhabdoid tumor cells were evaluated for the impact of CFI-400945 on the induction of apoptosis by Annexin V staining. We observed a significant increase in total cell death in all rhabdoid cells investigated in the first 48 hours of exposure to the compound (100 nM) as demonstrated in FIG. 9. The mechanism for cell death at short time exposure to the compound is still to be elucidated.

Senescence is an irreversible state of complete cessation of cell division [25]. Observation of cells exposed to CFI-400945 (100 nM) for an extended period of time (over 30 days) showed a progressive increase in cell size (hypertrophy), which is a sign of senescence [26, 27] (FIG. 10). We also measured senescence via a beta-galactosidase assay, the current gold standard marker of senescence [28], and demonstrated significantly higher levels of senescence in treated cells when compared to the controls. The ability of a cell to re-enter into the cell cycle was evaluated by a clonogenic recovery assay. All cell lines exposed to the compound for 6 days lost their ability to generate colonies (FIG. 11).

We performed a 48 hour time-lapse experiment to compare treated MON cells (100 nM) to control MON cells exposed to 0.1% DMSO and witnessed that cells treated with the compound demonstrated inability to go through cytokinesis after DNA endoreduplication. As a result of abortive mitoses, an increase in nuclear volume and consequently, cell size was observed [27].

Inhibition of PLK4 Caused Polyploidy in Tumor Cells while not Affecting Non-Neoplastic Human Fibroblasts.

As a result of the inhibition of centriole duplication by the drug, the cells did not undertake cytokinesis becoming polyploid, as determined through cell cycle analysis by flow cytometry. Conversely, the non-neoplastic human fibroblast cell line IIFF-SCC058, which has low expression of PLK4 [9], maintained its diploid status when challenged with CH-400945 (data not shown).

Polyploidy Induced by PLK4 Inhibition Sensitized RT and MB Cells to Cytotoxic Effects of DNA-Damaging Drugs.

We demonstrated that treatment of RT and MB cells lines with CFI-400945 inhibited PLK4 expression, inducing polyploidy (data not shown). Because it has been previously postulated that polyploidization increases the sensitivity of mammalian cells to DNA-damaging agents [29], and it is well known that doxorubicin exhibits clinically relevant cytotoxicity in RT [30-32], we hypothesized that combining CFI-400945 with conventional chemotherapy drugs like doxorubicin and etoposide would act synergistically on the induction of apoptosis. Using a viability assay, we demonstrated that cells simultaneously treated with the PLK4 inhibitor and doxorubicin or etoposide exhibited significantly lower IC50 values than cells receiving monotherapy at equivalent doses, providing evidence that cells became significantly more sensitive to the cytotoxic effects of doxorubicin and/or etoposide when treated in association with the PLK4 inhibitor (Table 1).

CFI-400945 has Potential Brain Exposure.

To determine the potential for blood-brain permeability of CFI-400945, its concentration was measured in plasma and in the brain of male CD-1 mice, using a Tmax based on published pharmacokinetic data [33]. Raw brain-to-plasma ratios (B:P) were determined by dividing the brain concentration in ng/g by the plasma concentration in ng/g (with plasma, density assumed to be of 1 g/mL). The average B:P ratio was determined to be approximately 0.08±0.3 (FIG. 12). No further CFI-400945 pharmacokinetic studies were done as part of this study.

The PLK4 Inhibitor CFI-400945 Produced Clinical Response in Intracranial AT/RT Xenografts.

To determine the in vivo anti-tumor activity of CFI-400945, we conducted an experiment in which mice with intracranial AT/RT xenografts were treated with CFI-400945 at 7.5 mg/kg/day consecutively for 21 days by daily oral administration [33]. Treatment with the PLK4 inhibitor significantly reduced the growth of intracranial AT/RT tumors (p=0.0146) and extended the survival of treated animal subjects (p=0.0477). (See FIG. 13B). Analysis of brain tumors, obtained from pre-symptomatic mice at the end of the therapy, showed significantly increased nuclear diameter and nuclear area, consistent with CFI-400945 pharmacodynamics (FIG. 13).

DISCUSSION

We previously demonstrated upregulation of PLK4 in RT and detected this overexpression also in other embryonal tumors of the brain including pediatric MB [9, 10]. Our preliminary findings indicated that RT cell proliferation was dependent on PLK4 and that the PLK4i CFI-400945 proffered significant therapeutic effects in vitro, in RT cells originating from different locations. This suggested that targeting PLK4 with small-molecule inhibitors could represent a novel strategy to treat RT [9]. Here, we further explore the mechanisms of PLK4 inhibition in RT and extend the insights to pediatric MB and in vivo effects.

TABLE 1

Association therapy of CFI-400945 with DNA-damaging drugs as determined by a viability assay

| Cell Line | Compound 1 | Compound 2 | IC50 of compound 2 (μM) | Standard deviation compound 2 | P value* |
|---|---|---|---|---|---|
| MON |  | Doxorubicin | 0.134 | 0.01713 |  |
| MON | CFI-400945 (5 nM) | Doxorubicin | 0.074 | 0.00125 | 0.0631 |
| MON | CFI-400945 (10 nM) | Doxorubicin | 0.057 | 0.00806 | 0.0386 |
| MON |  | Etoposide | 0.967 | 0.00668 |  |
| MON | CFI-400945 (5 nM) | Etoposide | 0.292 | 0.01590 | 0.0902 |
| MON | CFI-400945 (10 nM) | Etoposide | 0.266 | 0.00290 | 0.0010 |
| BT-16 |  | Doxorubicin | 1.429 | 0.00806 |  |
| BT-16 | CFI-400945 (5 nM) | Doxorubicin | 0.566 | 0.00450 | 0.0118 |
| BT-16 | CFI-400945 (10 nM) | Doxorubicin | 0.576 | 0.00650 | 0.0213 |
| BT-16 |  | Etoposide | 0.800 | 0.02269 |  |
| BT-16 | CFI-400945 (5 nM) | Etoposide | 0.593 | 0.01034 | 0.0743 |
| BT-16 | CFI-400945 (10 nM) | Etoposide | 0.006 | 0.00873 | 0.0002 |
| DAOY |  | Doxorubicin | 0.263 | 0.01178 |  |
| DAOY | CFI-400945 (5 nM) | Doxorubicin | 0.168 | 0.00309 | 0.0198 |
| DAOY | CFI-400945 (10 nM) | Doxorubicin | 0.199 | 0.00356 | 0.0573 |
| DAOY |  | Etoposide | 0.495 | 0.01296 |  |
| DAOY | CFI-400945 (5 nM) | Etoposide | 0.494 | 0.01744 | 0.4946 |
| DAOY | CFI-400945 (10 nM) | Etoposide | 0.800 | 0.00374 | NS |

NS—not significant
*IC50 value for combination vs. IC50 control.

Protein Kinases and Kinase Inhibitors.

Protein kinases regulate multiple cellular functions. They intermediate the coordinated amplification and propagation of cellular stimuli into distinct biological responses via synchronized signal transduction cascades [20]. Mutations and dysregulation of protein-kinases play fundamental roles in human disease, providing the possibility of developing agonists and antagonists for therapeutic purposes. Expanded discovery, research and development of orally active protein-kinase inhibitors has culminated in the approval of many of these drugs for clinical use [34].

Polo-Like Kinases.

Polo-like kinases (PLKs) are part of the conserved family of serine/threonine kinases that play essential roles in cell cycle progression and DNA damage response. They are often deregulated in cancer [35]. Mammalian cells contain five polo-like family members, PLK 1-5, of which, PLK1 is the most extensively characterized with many inhibitors already in clinical trials [36, 37]. PLK4 is structurally different from the other family members. While PLK1, 2 and 3 possess two Polo-box domains at their C-terminus, PLK4 only has one [14, 38].

PLK4 Activity, Regulation and the Paradoxical Effect of its Inhibition.

PLK4 activity is essential for centrosome duplication [17]. Centrosomes are present as a single copy at the beginning of the cell cycle and duplicate during S phase producing two copies, each one becoming a spindle pole during mitosis. Within the centrosome, a pair of centrioles controls centrosome duplication [39]. PLK4 is present in its inactive form at centrioles in G1, becoming active in S phase and increasing gradually with progression through the cell cycle. Maximum amount of active PLK4 protein is achieved in mitosis [14]. The PLK4 gene is transcribed in a cell dependent manner with mRNA expression progressively increasing throughout the cell cycle mirroring the protein levels [14].

PLK4 is a low abundance, short lived protein, with activity regulated by its own stability. This self-regulation occurs through formation of homodimers that trans-autophosphorylate for degradation. This "auto-regulatory feedback loop" [40] keeps PLK4 levels under tight regulation and limits centriole duplication in normal cells [40-42]. Inhibition of PLK4 triggers failure of centriole duplication, while PLK4 overexpression promotes centriole overduplication which results in the formation of extra centrosomes with subsequent genome instability and propensity for tumor formation [43, 44].

It has been demonstrated that Plk4 heterozygous mice are predisposed to tumorigenesis [45]. It has also been established that overexpression of PLK4 promotes centrosome amplification initiating tumorigenesis in flies [46]. Accordingly, Mason and colleagues [11] demonstrated that high dose treatment with CFI-400945 resulted in failure in centriole duplication. Yet, when the authors used lower concentrations of the compound, an increase in centriole number was observed. This bimodal phenomenon or paradoxical effect was also observed in this study when we treated multiple RT and MB cell lines with different concentrations of the inhibitor, as depicted in FIG. 8.

This paradoxical effect has been explained by the stable overexpression of kinase-inactive PLK4 upon partial inhibition of PLK4 with low doses of the inhibitor. As a result of this partial inhibition there is formation of heterodimers instead of homodimers. The heterodimers are composed of a kinase-inactive PLK4 molecule and a wild-type PLK4 molecule. In these circumstances, the kinase inactive PLK4 cannot destabilize the active PLK4, leading to an increase in kinase activity. The resultant increase in activity could, in turn, result in higher PLK4 abundance and centriole overduplication [42]. With high doses of the compound, there is a more extensive inhibition of PLK4 activity that attenuates the feedback of auto-catalyzed destruction. This scenario would result in failure of centriole duplication and consequent blockage of cytokinesis with impairment of cell proliferation [11, 47].

Polyploid, Senescence and Cell Death.

Polyploidy is defined as increased sets of homologous chromosomes in a cell that might occur due to abnormal cell division. Because an abnormally high chromosome count makes polyploid cells more prone to errors during cell division, polyploidy is considered an undesirable event that may lead to cancer development. However, it has been postulated that polyploid cancer cells are also more sensitive to DNA-damaging agents [27, 29]. In this scenario, induction of polyploidy by inhibiting PLK4 may represent a new approach to cancer therapy.

To induce polyploidy, an agent must allow cells to re-enter a new cycle without going through cytokinesis. We demonstrated that CFI-400945 is an inducer of cancer cell polyploidy in multiple RT and MB cell lines, yielding cell populations with a high degree of polyploidy (>8N) while not affecting non-neoplastic HFF-SCC058 human fibroblasts (data not shown). These findings are consistent with the phenomenon demonstrated by Tovar and colleagues using the small molecule inducer of polyploidy R1530 where non-cancerous cell were protected from R1530-induced polyploidy [27]. The fact that non-neoplastic proliferating cells seem to be "resistant" to CFI-400945-induced polyploidy supports the rationale for cancer therapy by PLK4 inhibitors.

The mitotic apparatus is frequently unable to cope with a high degree of polyploidy which leads to mitotic catastrophe and cell death [27, 48]. We demonstrated that RT as well as MB cell lines underwent a certain degree of apoptosis during the first 48 hours of exposure to the inhibitor, as illustrated in FIG. 9. However, not all polyploid cells underwent apoptosis. A sizeable amount of cells became senescent, remaining viable but not replicating (FIG. 10).

Senescence is defined as the permanent loss of proliferative potential of a cell. Senescent cells move from an actively dividing to a non-dividing state, yet remain metabolically active. In conjunction with the loss of the ability to divide, changes occur in cell morphology and in their pattern of gene expression. Although cells may remain viable for a long time, at the end of the process cell death usually occurs [26]. We documented the senescent state of cells treated with CFI-400945 by measuring beta-galactosidase at different time-points. Furthermore, to document the irreversibility of CFI-400945 induced proliferation arrest in RT and MB cells, we detected the loss of the ability to generate colonies after 6 days of exposure to the drug. Although the cells remained alive after 12 days of drug-free media treatment, they did not recover the ability to divide and generate colonies as illustrated in FIG. 11.

Association Therapy.

Chemotherapy is an important element in current cancer treatments. However, the use of many anticancer drugs is restrained by dose-limiting toxicities as well as development of drug resistance. Therefore, being able to lower the dose of these chemotherapy agents would be highly beneficial for patients, especially children.

Doxorubicin is a potent cytotoxic anthracycline compound and an important part of RT treatment [31, 32, 49, 50].

It intercalates with the DNA and inhibits topoisomerase II. It is highly effective, but its use is limited by cardiotoxicity resulting in dilative cardiomyopathy [51].

Etoposide is also a topoisomerase II inhibitor widely used for cancer therapy. It is a cytotoxic alkaloid compound that causes single or double-strand DNA breaks [52]. It has been used in combination with other agents to treat several embryonal tumors like recurrent MB, high risk Wilms' tumors, rhabdomyosarcoma, Ewin's sarcoma and neuroblastoma [53].

It has been postulated that polyploid cancer cells may be more sensitive to DNA-damaging agents [27, 29]. Using viability assays, we demonstrated that the combination of PLK4i CFI-400945 with the conventional chemotherapeutic DNA-damaging agents, doxorubicin or etoposide, resulted in a clear reduction of their IC50 values (data not shown and Table 1), meaning that induction of polyploidy by the PLK4i CFI-400945 sensitizes RT and MB cell lines to doxorubicin and/or etoposide treatment and therefore, may represent a new approach to cancer therapy.

Blood Brain Barrier (BBB) Penetration and Intracranial Xenograft Response.

Most kinase-targeted drugs that have been investigated, including the PLK4i CFI-400945, were not developed for CNS disorders. The development of kinase-targeted therapies for CNS diseases remains a challenge, and the greatest challenge facing these drugs is the effective penetration of the BBB. It is estimated that only about 2% of small-molecule drugs are able to effectively cross the BBB [54]. The physicochemical properties of a drug considerably influence passive diffusion across biological membranes and the potential to serve as a substrate for the P-glycoprotein (PGP) efflux transporter. Molecular weight (MW), polar surface area (PSA) and lipophilicity (LogP) are key molecular properties that correlate with and may have an important role in influencing the BBB penetrance of a molecule [55]. While CFI-400945 is attractive as an adult stage non-CNS candidate, it is at the cusp of molecular properties (MW=534.65, cLogP=4.48 and PSA=79.48) found in drugs with adequate CNS exposure to allow target engagement. We determined that the brain to plasma ratio (B:P) of CFI-400945 was <0.1 for CD-1 ("wild type") mice but did not determine detailed brain pharmacokinetics or screen for brain to plasma ratio in the xenograft model. The most parsimonious explanation for why we were able to observe pharmacodynamics effects in the xenograft tumors consistent with CFI-400945 mechanism of action (and significant cell hypertrophy observed in tumors harvested from treated animals) is the possibility that the BBB is altered in the "disease model state" to make it more accommodating to a less than ideal drug candidate. This is consistent with the concept of BBB physiological changes in disease state that are not evident at the anatomical level [56]. Further, our in-vivo anti-tumor activity of CFI-400945 was seen at doses previously used by Mason and colleagues to treat peripheral xenograft tumors [11]. Clearly, there are other likely explanations, such as retention or deposit of CFI-400945 in brain tissue after repeated daily dosing over an extended period of time. However, these various theoretical possibilities were not pursued as part of this study. The key relevant aspect to our overall goal was the demonstration that CH-400945 treatment significantly reduced growth of intracranial tumors and significantly extended the survival of treated animals. Future screens for CNS therapeutic candidates or refinement of existing peripheral tissue therapeutics will be needed to address the brain exposure challenge in order to optimize candidates for future clinical trials.

Kinase Selectivity and Risk Potential for PLK4 Inhibitors.

All FDA approved kinase inhibitor drugs are multi-kinase inhibitors and approvals are directed by oncology indications. Further, the approved kinase inhibitor drugs are dominated by those that target the tyrosine protein kinase (Y-PK) family. Only four appear to target the serine/threonine protein kinase (S/T-PK) class as their molecular mechanism of action. None of the approved protein kinase inhibitor drugs are for CNS indications. PLK4 is an S/T-PK, and we are addressing brain tumors in our studies. Therefore, the finding that a prototype PLK4 inhibitor drug candidate, CFI-400945, is effective in a brain tumor model is a significant finding in itself. The additional finding that CFI-400945 falls within the norm of approved oncology therapeutics that are typically multi-kinase inhibitors with a subset of kinome selectivity is encouraging. As with extant approved kinase inhibitor drugs, some of the cross-over kinase hits for CFI-400945 under 1,000 nM IC50 are not unexpected based on kinase structural similarities (e.g., aurora kinases) and others fit the prevailing view that a set of multiple kinases must be hit for optimal efficacy [22]. Further probing of kinase inhibitor specificity links to in vivo efficacy must await the availability of more selective kinase inhibitors with CNS exposure properties. Our results with CFI-400945 in brain tumor models indicate the potential therapeutic utility of such endeavors. Finally, the cardiotoxicity associated with cancer therapeutics and Y-PK inhibitor drugs does not appear to be a primary concern for PLK4 targeting with mixed kinase inhibitors as represented by CFI-400945, nor is there an obvious high pharmacogenomic risk for individual variability in response or toxicity based on CYP2D6 activity.

Materials and Methods

Ethics Statement.

Investigation has been conducted in accordance with the ethical standards and according to the Declaration of Helsinki and according to national and international guidelines and has been approved by the authors' institutional review board.

Cell Culture.

MON cells, which were provided by Dr. Delattre (Institute Curie, Paris, France), were established from an abdominal rhabdoid tumor [57-59]. The G401 cell line (ATCC, USA) was established from a RTK. The AT/RT cell lines, BT-12 and BT-16, which have been extensively used in preclinical studies [60, 61], were established by Drs. Houghton and Biegel (Nationwide Children's Hospital, Columbus, Ohio and The Children's Hospital of Philadelphia, Philadelphia, Pa., respectively). The two MB cell lines DAOY and D283 (ATCC, USA) are classified as belonging to the sonic hedgehog (SUM) molecular subgroup and group 3/4 respectively [21]. As a non-neoplastic control, we used TIFF-SCC058 cells (EDM Millipore, USA) derived from human foreskin fibroblasts which have significantly lower expression of PLK4 [9]. MON, BT-12 and BT-16 cells were maintained in HyClone RPMI 1640 (GE Healthcare Life Sciences, USA), G401 in McCoy's 5A (Sigma Aldrich, USA), HFF-SCC058 in DMEM (Thermo Fisher Scientific, USA), and DAOY and D283 in EMEM (Thermo Fisher Scientific, USA). All media were supplemented with 10% FBS and 1% penicillin/streptomycin and cells were maintained at 37° C., 5% CO2.

Kinase Activity Screening.

The inhibitory activity of CFI-400945 on various kinases was assessed through 486 biochemical kinase assays using 500 nM of the compound. These assays utilized various formats appropriate to the kinase, its substrate and its activity. Formats included the Z-LYTE™ Kinase Assay that determines the differential sensitivity of phosphorylated and non-phosphorylated peptide substrates to proteolytic cleavage using a FRET-based readout, the Adapta™ Universal Kinase Assay that employs a homogeneous, fluorescence-based immunoassay for the detection of ADP produced by kinases and the LanthaScreen™ Eu Kinase Binding Assay that utilizes an Alexa Fluor™ conjugated "tracer" and an Eu-labeled anti-tag antibody to measure binding of a compound to the kinase target [62]. The half maximal inhibitory concentration (1050) at selected, highly inhibited kinases was further evaluated by 10-point titration (SelectScreen™ Kinase Profiling Services—Thermo Fisher Scientific, USA) [63, 64].

Drug safety and toxicology.

Analysis of CFI-400945 against a panel of P450s isoenzymes (1A2, 2B6, 2C8, 2C9, 2C19, 2D6, 2J2, 3A4 and 3A5) and Vivid™ substrates was determined using 10-point titrations, in duplicates to determine IC50 values (SelectScreen™ P450 Profiling Service Thermo Fisher, USA) [65, 66]. To determine if the compound binds the cardiac hERG channel, the 1050 was quantitated using a 10-point titration, in duplicates in a hERG fluorescence polarization assay (SelectScreen™ hERG Screening Service—Thermo Fisher Scientific, USA) [67].

Cell Proliferation, Colony Formation, Migration and Invasion Assays of MB Cell Lines.

Cell proliferation, colony formation, migration and invasion of the MB cell lines DAOY (SHH subtype) and D283 (group 3/4 subtype) were performed as previously described [9]. For proliferation assay DAOY was plated with 5×104 cells per well and D283 was plated with 5×105 cells per well.

Compounds.

Cells were treated as indicated below with the following compounds: CFI-400945 (CAS 1338800-06-8—Cayman Chemical, USA), doxorubicin (CAS 25316-40-9—MedChem Express, USA) and etoposide (CAS 33419-42-0—Cayman Chemical, USA).

Viability Assay.

To evaluate cell viability, we used the Presto Blue™ Cell Viability reagent (Thermo Fisher Scientific, USA). Cells were plated in triplicates in 96-well plates. Except DAOY and D283, all cell lines were plated with 2×103 cells per well 96-well and the absorbance was measured after 48 and 72 hours at drug concentrations of 5, 10, 50, 100, 200, 500 nM, 1 µM and 5 µM. DAOY was plated with 5×104 cells per well and D283 was plated with 5×105 cells per well.

Confluency Assay.

For further evaluation of the effect of the PLK4 inhibitor over tumor cell proliferation, confluency was measured over a 48 hour period. MON, BT-12, G401 and DAOY cells were plated in 96-well plates with a density of 6×104 per well. On day 1, CFI-400945 was added to the cells in increasing concentrations (0, 0.12, 0.49, 1.95, 7.81, 31.25, 125 and 500 nM). Confluency was monitored for 48 hours by taking phase contrast images every 2 hours and measured using an IncuCyte ZOOM system (Essen BioScience, USA). Experiments were performed in triplicates.

Immunofluorescent Assays.

Cells treated with various concentrations of CFI-400945 and 0.1% DMSO (control) were seeded on Poly Lysine (Sigma, USA) coated coverslips, washed twice with 1×PBS, fixed in ice cold Methanol (Fisher Chemical, USA) at −20° C. for 10 min and then permeabilized with 0.25% Triton-X (Acros Organics, USA) at room temperature (RT) for 10 min. The cells were then blocked in blocking buffer (5% BSA (Jackson Immuno Research Laboratories Inc., USA) in PBST) for 1 hour at RT. The primary antibody (Anti-λ Tubulin 1:500, Sigma, USA) diluted in 1% BSA in PBST was then added and incubated at 4° C. overnight. Then, the cells were washed with 1×PBS thrice. Secondary antibody (Anti-Rabbit IgG (H+L) F (ab') 2, 1:500, Sigma, USA) diluted in 1% BSA in PBST was added and incubated at RT for 2 hours. Three time washes with IX PBS were performed. Then, 1 mL of DAPI (Thermo Fisher Scientific, USA) in PBS (0.5 µl of DAPI in 10 ml PBS) was added to the cells and incubated for 10 min at RT. Finally, 3 time washes with 1×PBS were performed and slides were mounted using Mounting Medium (Thermo Fisher Scientific, USA).

Flow Cytometry—Apoptosis.

Cells were treated with various concentrations of CH-400945 and 0.1% DMSO (control) for evaluation of the impact of treatment on induction of apoptosis. Live cells were stained with Annexin V as an indicator of early apoptosis and Propidium Iodide (PI—Thermo Fisher Scientific, USA) for detection of late apoptosis and necrosis, according to manufacturer's instructions (Thermo Fisher Scientific, USA). Flow cytometric analysis was performed on a BD Fortessa instrument (BD Biosciences, USA) within an hour of staining. Data was analyzed using Modfit LT from Verity Software House. All experiments were performed in triplicates.

Flow Cytometry—cell cycle.

Cell cycle evaluation was performed by staining the cells with PI (Thermo Fisher Scientific, USA) according to manufacturer's instructions. Cells treated with CFI-400945 and 0.1% DMSO (control) were fixed in 80% ethanol overnight, stained with PI and then subjected to flow cytometric analysis using a BD Fortessa instrument (BD Biosciences, USA). Data was analyzed using Modfit LT from Verity Software House. Experiments were performed in triplicates.

Senescence.

Senescence of cells treated with CFI-400945 and 0.1% DMSO (control) was detected using the Senescence Cells Histochemical Kit (Sigma, USA), which is based on a histochemical stain for beta-galactosidase activity at pH 6. For each cell line, cells were seeded in 6-well plates in triplicates with 100,000 cells per well. Treatment medium was added the next day and incubated for 48 or 72 hrs. After incubation, cells were washed twice with 1×PBS and 1 mL of the Fixation Buffer from the kit was added to each well of the plate and incubated at RT for 5 min. Cells were washed with 1×PBS and 1 mL of staining solution from the kit was added to each well and incubated at 37° C. without CO2 overnight. The next day, the cells were washed with 1×PBS and the numbers of blue stained cells (which indicate senescent cells) and unstained cells were counted in image J (www.imagej.nih.gov). The percentage of senescent cells was calculated.

Clonogenic recovery assay.

For each cell line, 200 cells were seeded into 6-well tissue culture plates. Cells were incubated for 6 days with 100 nM of CFI-400945. On the 7th day, cell were washed with IX PBS twice and then incubated with 0.1% DMSO for an additional 12 days. Controls were: (1) incubated with 0.1% DMSO for 18 days and (2) incubated with CFI-400945 100 nM for 18 days. The number of colonies was counted. All experiments were performed in triplicates.

Quantitative Real-Time PCR.

The expression of PLK4 (Hs00179514_m1) in each cell line was verified by TaqMan GE assays (Thermo Fisher Scientific, USA) using the housekeeping gene GAPDH (Hs02758991_g1) as reference. Total RNA (2 µg) was used to make cDNA using the Applied Biosystems High Capacity RNA-to-cDNA kit (Thermo Fisher Scientific). Reactions were performed in triplicate with adequate positive and negative controls. The normalized expression levels were calculated by AACt method using the housekeeping gene and a pool of all samples as calibrator.

Time-Lapse Assay.

Time-lapse images of MON cells treated 100 nM CFI-400945 and 0.1% DMSO for 48 hours were taken using a Zeiss LSM 800 confocal microscope (Zeiss XL-LSM710S1 live-cell incubator system with CO2 Module S, and Heating Unit XL S, Zeiss, USA) set to normal growing conditions (37° C., 5% CO2). Cells were plated in 35 mm glass bottom dishes (Cat #150682, Thermo Fisher Scientific, USA) in normal growth medium and allowed to grow overnight. After the treatment medium was added, imaging began immediately. Brightfield images (20×) were taken every 6 minutes at 10 predetermine fields for 48 hours. Images were processed in ZEN 2.3 software (Zeiss, USA).

Combination Therapy—Viability Assay.

To quantify the effects of the treatment with the PLK4i CFI-400945 in combination with DNA-damaging chemotherapy agents, viability assays were performed using the Presto Blue™ Cell Viability reagent (Thermo Fisher Scientific, USA). Cells were plated in triplicates in 96-well plates. Cells were treated with a combination of 5 or 10 nM CFI-400945 and 1, 5, 10, 50, 100, 200, 500 nM, 1 and 5 µM of doxorubicin or etoposide for 72 hours. Cells were also treated with the same concentrations of CFI-400945, doxorubicin and etoposide alone, as well as 0.1% DMSO as controls. The percentage of viable cells compared to the controls was calculated using the average DMSO absorbance values compared to the treated absorbance values. The percent of viable cells' curves were made using the statistical software PRISM (GraphPad Software, USA) and IC50 values were calculated from the curves. P-values were calculated by (unpaired t-test) comparing the absorbance values of the combination therapy and each cytotoxic drug alone at the nearest IC50 value of the combination therapy.

Brain to Plasma Ratio (B:P).

Male CD-1 mice weighing between 20 and 40 grams were fitted with jugular vein cannulas as appropriate and fasted overnight until 4 hours post-dose. Double route of administration (oral and IV) were tested, with a single dose concentration of 7.5 mg/kg [11]. Plasma and brain were sampled at 6 time-points, starting at 30 minutes (n=3 animals/time-point). Brain was extracted at the same plasma sampling time-point from each animal. Both plasma and brain samples were deproteinated. Brain samples were weighted, homogenized and CFI-400945 was extracted. Then, mass spectrometry (MS) optimization for CFI-400945 detection was performed; liquid chromatography (LC) evaluation using a generic reverse phase column and gradient method for separation of CH-400945 from matrix interference was performed. Finally, a 6 point standard curve for CFI-400945 with an internal standard (Verapamil) and determination of CFI-400945 concentrations in the dosing solutions and incurred samples was performed using a generic LC-MS/MS method. The dosing solution was normalized in a matched matrix (mouse plasm) and analyzed in triplicate in the same analytical batch as the incurred samples (Absorption Systems—Exton, Pa.).

Intracranial Xenograft Tumors.

Six-week-old female athymic mice (rnu/rnu genotype, BALB/c background) were purchased from Envigo (Harlan) and housed under aseptic conditions, which included filtered air and sterilized food, water, bedding, and cages. The Northwestern University Institutional Animal Care and Use Committee approved all animal protocols. The BT-12 AT/RT cell line, which has high expression of PLK4 was modified to express luciferase and injected intracranially in nude mice as previously described [68]. Each mouse was injected with a cell suspension (10,000 cells/3 µL) into the right caudate putamen of the brain. Mice injected BT-12 cells (n=20) were randomized in two treatment groups: 1) control (vehicle alone), 2) CFI-400945 (7.5 mg/kg/day for 21 days). Bioluminescence monitoring was performed twice a week throughout the course of the experiment for quantitative measurement of tumor growth and response to therapy. Kaplan-Meier survival analysis was performed to assess survival benefit within the treatment group as compared to controls. Differences between survival curves were calculated using a log-rank test. Brains were resected at 6 hours following completion of the treatment and placed in 4% paraformaldthyde for subsequent histological examination.

CONCLUSION

We demonstrated initial evidence of PLK4 as a CNS druggable target for rhabdoid tumors and MB. Our findings indicate that targeting PLK4 with optimized small-molecule inhibitors may hold a novel strategy for the treatment of embryonal tumors, including those of the CNS.

REFERENCES (EXAMPLE 2)

1. Grupenmacher A T, Halpern A L, Bonaldo Mde F, Huang C C, Hamm C A, de Andrade A, Tomita T, Sredni S T. Study of the gene expression and microrna expression profiles of malignant rhabdoid tumors originated in the brain (AT/RT) and in the kidney (RTK). Childs Nery Syst. 2013; 29:1977—83.
2. Sredni S T, Tomita T. Rhabdoid tumor predisposition syndrome. Pediatr Dev Pathol. 2015; 18:49-58.
3. Fruhwald M C, Biegel J A, Bourdeaut F, Roberts C W, Chi S N. Atypical teratoid/rhabdoid tumors-current concepts, advances in biology, and potential future therapies. Neuro Oncol. 2016; 18:764-78.
4. Ginn K F, Gajjar A. Atypical teratoid rhabdoid tumor: current therapy and future directions. Front Oncol. 2012; 2:114.
5. Chi S N, Zimmerman M A, Yao X, Cohen K J, Burger P, Biegel J A, Rorke-Adams L B, Fisher M J, Janss A, Mazewski C, Goldman S, Manley P E, Bowers D C, et al. Intensive multimodality treatment for children with newly diagnosed CNS atypical teratoid rhabdoid tumor. J Clin Oncol. 2009; 27:385-9.
6. Taylor M D, Northcott P A, Korshunov A, Remke M, Cho Y J, Clifford S C, Eberhart C G, Parsons D W, Rutkowski S, Gajjar A, Ellison D W, Lichter P, Gilbertson R J, et al. Molecular subgroups of medulloblastoma: the current consensus. Acta Neuropathol. 2012; 123:465-72.
7. Kool M, Korshunov A, Remke M, Jones D T, Schlanstein M, Northcott P A, Cho Y J, Koster J, Schouten-van Meeteren A, van Vuurden D, Clifford S C, Pietsch T, von Bueren A O, et al. Molecular subgroups of medulloblastoma: an international meta-analysis of transcriptome, genetic aberrations, and clinical data of WNT, SHH, Group 3, and Group 4 medulloblastomas. Acta Neuropathol. 2012; 123:473-84.
8. Ramaswamy V, Taylor M D. Medulloblastoma: from myth to molecular. J Clin Oncol. 2017; 35:2355-63.

9. Sredni S T, Suzuki M, Yang J P, Topczewski J, Bailey A W, Gokirmak T, Gross J N, de Andrade A, Kondo A, Piper D R, Tomita T. A functional screening of the kinome identifies the polo-like kinase 4 as a potential therapeutic target for malignant rhabdoid tumors, and possibly, other embryonal tumors of the brain. Pediatr Blood Cancer. 2017.

10. Sredni S T, Tomita T. The polo-like kinase 4 gene (PLK4) is overexpressed in pediatric medulloblastoma. Childs Nery Syst. 2017; 33:1031.

11. Mason J M, Lin D C, Wei X, Che Y, Yao Y, Kiarash R, Cescon D W, Fletcher G C, Awrey D E, Bray M R, Pan G, Mak T W. Functional characterization of cfi-400945, a polo-like kinase 4 inhibitor, as a potential anticancer agent. Cancer Cell. 2014; 26:163-76.

12. Sampson P B, Liu Y, Patel N K, Feher M, Forrest B, Li S W, Edwards L, Laufer R, Lang Y, Ban F, Awrey D E, Mao G, Plotnikova 0, et al. The discovery of polo-like kinase 4 inhibitors: design and optimization of spiro [cyclopropane-1,3' [3H]indol]-2'(1'H). ones as orally bioavailable antitumor agents. J Med Chem. 2015; 58:130-46.

13. Berger T, Saunders M E, Mak T W. Beyond the oncogene revolution: four new ways to combat cancer. Cold Spring Harb Symp Quant Biol. 2016; 81:85-92.

14. Sillibourne J E, Bornens M. Polo-like kinase 4: the odd one out of the family. Cell Div. 2010; 5:25.

15. Rosario C O, Kazazian K, Zih F S, Brashavitskaya O, Haffani Y, Xu R S, George A, Dennis J W, Swallow C J. A novel role for Plk4 in regulating cell spreading and motility. Oncogene. 2015; 34:3441-51.

16. Bettencourt-Dias M, Rodrigues-Martins A, Carpenter L, Riparbelli M, Lehmann L, Gatt M K, Carmo N, Balloux F, Callaini G, Glover D M. SAK/PLK4 is required for centriole duplication and flagella development. Curr Biol. 2005; 15:2199-207.

17. Habedanck R, Stierhof Y D, Wilkinson C J, Nigg E A. The polo kinase Plk4 functions in centriole duplication. Nat Cell Biol. 2005; 7:1140-6.

18. Shinmura K, Kurabe N, Goto M, Yamada H, Natsume H, Konno H, Sugimura H. PLK4 overexpression and its effect on centrosome regulation and chromosome stability in human gastric cancer. Mol Biol Rep. 2014; 41:6635-44.

19. Mittal K, Ogden A, Reid M D, Rida P C, Varambally S, Aneja R. Amplified centrosomes may underlie aggressive disease course in pancreatic ductal adenocarcinoma. Cell Cycle. 2015; 14:2798-809.

20. Chico L K, Van Eldik L J, Watterson D M. Targeting protein kinases in central nervous system disorders. Nat Rev Drug Discov. 2009; 8:892-909.

21. Ivanov D P, Coyle B, Walker D A, Grabowska A M. in vitro models of medulloblastoma: choosing the right tool for the job. J Biotechnol. 2016; 236:10-25.

22. Fabbro D, Cowan-Jacob S W, Mobitz H, Martiny-Baron G. Targeting cancer with small-molecular-weight kinase inhibitors. Kinase Inhibitors. Methods in Molecular Biology (Methods and Protocols). 2012; 795:1-34.

23. Lamothe S M, Guo J, Li W, Yang T, Zhang S. The human ether-a-go-go-related gene (hERG) potassium channel represents an unusual target for protease-mediated damage. J Biol Chem. 2016; 291:20387-401.

24. Lynch T, Price A. The effect of cytochrome P450 metabolism on drug response, interactions, and adverse effects. Am Fam Physician. 2007; 76:391-6.

25. Terzi M Y, Izmirli M, Gogebakan B. The cell fate: senescence or quiescence. Mol Biol Rep. 2016; 43:1213—20.

26. Demidenko Z N, Blagosklonny M V. Quantifying pharmacologic suppression of cellular senescence: prevention of cellular hypertrophy versus preservation of proliferative potential. Aging (Albany N.Y.). 2009; 1:1008—16.

27. Tovar C, Higgins B, Deo D, Kolinsky K, Liu J J, Heimbrook D C, Vassilev L T. Small-molecule inducer of cancer cell polyploidy promotes apoptosis or senescence: implications for therapy. Cell Cycle. 2010; 9:3364-75.

28. Itahana K, Campisi J, Dimri G P. Methods to detect biomarkers of cellular senescence: the senescence-associated beta-galactosidase assay. Methods Mol Biol. 2007; 371:21-31.

29. Hau P M, Siu W Y, Wong N, Lai P B, Poon R Y. Polyploidization increases the sensitivity to DNA-damaging agents in mammalian cells. FEBS Lett. 2006; 580:4727-36.

30. Rosson G B, Vincent T S, Oswald B W, Wright C F. Drug resistance in malignant rhabdoid tumor cell lines. Cancer Chemother Pharmacol. 2002; 49:142-8.

31. Kerl K, Ries D, Unland R, Borchert C, Moreno N, Hasselblatt M, Jurgens H, Kool M, Gorlich D, Eveslage M, Jung M, Meisterernst M, Fruhwald M. The histone deacetylase inhibitor SAHA acts in synergism with fenretinide and doxorubicin to control growth of rhabdoid tumor cells. BMC Cancer. 2013; 13:286.

32. Furtwangler R, Kager L, Melchior P, Rube C, Ebinger M, Nourkami-Tutdibi N, Niggli F, Warmann S, Hubertus J, Amman G, Leuschner I, Vokuhl C, Graf N, et al. High-dose treatment for malignant rhabdoid tumor of the kidney: no evidence for improved survival—the gesellschaft fur padiatrische onkologie and hamatologie (GPOH) experience. Pediatr Blood Cancer. 2017.

33. Mason J M, Lin D C, Wei X, Che Y, Yao Y, Kiarash R, Cescon D W, Fletcher G C, Awrey D E, Bray M R, Pan G H, Mak T W. Functional characterization of CFI-400945, a polo-like kinase 4 inhibitor, as a potential anticancer agent. Cancer Cell. 2014; 26:163-76. https://doi.org/10.1016/j. ccr.2014.05.006.

34. Cohen P. Protein kinases—the major drug targets of the twenty-first century? Nat Rev Drug Discov. 2002; 1:309—15.

35. Gross S, Rahal R, Stransky N, Lengauer C, Hoeflich K P. Targeting cancer with kinase inhibitors. J Clin Invest. 2015; 125:1780-9.

36. Barr F A, Sillje H H, Nigg E A. Polo-like kinases and the orchestration of cell division. Nat Rev Mol Cell Biol. 2004; 5:429-40. https://doi.org/10.1038/nrm1401.

37. Liu Z, Sun Q, Wang X. PLK1, a potential target for cancer therapy. Transl Oncol. 2017; 10:22-32.

38. Leung G C, Hudson J W, Kozarova A, Davidson A, Dennis J W, Sicheri F. The Sak polo-box comprises a structural domain sufficient for mitotic subcellular localization. Nat Struct Biol. 2002; 9:719-24.

39. Nigg E A, Raff J W. Centrioles, centrosomes, and cilia in health and disease. Cell. 2009; 139:663-78.

40. Holland A J, Lan W, Niessen S, Hoover H, Cleveland D W. Polo-like kinase 4 kinase activity limits centrosome overduplication by autoregulating its own stability. J Cell Biol. 2010; 188:191-8.

41. Sillibourne J E, Tack F, Vloemans N, Boeckx A, Thambirajah S, Bonnet P, Ramaekers F C, Bornens M, Grand-Perret T. Autophosphorylation of polo-like kinase 4 and its role in centriole duplication. Mol Biol Cell. 2010; 21:547-61.

42. Cunha-Ferreira I, Bento I, Pimenta-Marques A, Jana S C, Lince-Faria M, Duarte P, Borrego-Pinto J, Gilberto S, Amado T, Brito D, Rodrigues-Martins A, Debski J, Acilan C, Saunders W S. A tale of too many centrosomes. Cell. 2008; 134:572-5.
43. Srsen V, Merdes A. The centrosome and cell proliferation. Cell Div. 2006; 1:26.
44. Acilan C, Saunders W S. A tale of too many centrosomes. Cell. 2008; 134:572-5.
45. Ko M A, Rosario C O, Hudson J W, Kulkarni S, Pollett A, Dennis J W, Swallow C J. PLK4 haploinsufficiency causes mitotic infidelity and carcinogenesis. Nat Genet. 2005; 37:883-8.
46. Basto R, Brunk K, Vinadogrova T, Peel N, Franz A, Khodjakov A, Raff J W. Centrosome amplification can initiate tumorigenesis in flies. Cell. 2008; 133:1032-42. https://doi.org/10.1016/j.cell.2008.05.039.
47. Holland A J, Cleveland D W. Polo-like kinase 4 inhibition: a strategy for cancer therapy? Cancer Cell. 2014; 26:151-3.
48. Castedo M, Perfettini J L, Roumier T, Andreau K, Medema R, Kroemer G. Cell death by mitotic catastrophe: a molecular definition. Oncogene. 2004; 23:2825-37.
49. Bourdeaut F, Chi S N, Fruhwald M C. Rhabdoid tumors: integrating biological insights with clinical success: a report from the SMARCB1 and rhabdoid tumor symposium, Paris, Dec. 12-14, 2013. Cancer Genet. 2014; 207:346-51.
50. Kramer K F, Moreno N, Fruhwald M C, Kerl K. BRD9 inhibition, alone or in combination with cytostatic compounds as a therapeutic approach in rhabdoid tumors. Int J Mol Sci. 2017; 18.
51. Cappetta D, Rossi F, Piegari E, Quaini F, Berrino L, Urbanek K, De Angelis A. Doxorubicin targets multiple players: a new view of an old problem. Pharmacol Res. 2017.
52. Aisner J, Lee E J. Etoposide. Current and future status. Cancer. 1991; 67:215-9.
53. Panigrahy D, Kaipainen A, Butterfield C E, Chaponis D M, Laforme A M, Folkman J, Kieran M W. Inhibition of tumor angiogenesis by oral etoposide. Exp Ther Med. 2010; 1:739-46.
54. Pardridge W M. The blood-brain barrier: bottleneck in brain drug development. NeuroRx. 2005; 2:3-14.
55. Chico L K, Van Eldik L J, Watterson D M. Targeting protein kinases in central nervous system disorders. Nat Rev Drug Discov. 2009; 8:892-909.
56. Pardridge W M. Drug transport across the blood-brain barrier. J Cereb Blood Flow Metab. 2012; 32:1959-72.
57. Zhang Z K, Davies K P, Allen J, Zhu L, Pestell R G, Zagzag D, Kalpana G V. Cell cycle arrest and repression of cyclin D1 transcription by INI1/hSNF5. Mol Cell Biol. 2002; 22:5975-88.
58. Albanese P, Belin M F, Delattre O. The tumour suppressor hSNF5/INI1 controls the differentiation potential of malignant rhabdoid cells. Eur J Cancer. 2006; 42:2326-34.
59. Versteege I, Medjkane S, Rouillard D, Delattre 0. A key role of the hSNF5/INI1 tumour suppressor in the control of the G1-S transition of the cell cycle. Oncogene. 2002; 21:6403-12.
60. Alimova I, Birks D K, Harris P S, Knipstein J A, Venkataraman S, Marquez V E, Foreman N K, Vibhakar R. Inhibition of EZH2 suppresses self-renewal and induces radiation sensitivity in atypical rhabdoid teratoid tumor cells. Neuro Oncol. 2013; 15:149-60.
61. Singh A, Lun X, Jayanthan A, Obaid H, Ruan Y, Strother D, Chi S N, Smith A, Forsyth P, Narendran A. Profiling pathway-specific novel therapeutics in preclinical assessment for central nervous system atypical teratoid rhabdoid tumors (CNS ATRT): favorable activity of targeting EGFR-ErbB2 signaling with lapatinib. Mol Oncol. 2013; 7:497-512.
62. Vogel K W, Zhong Z, Bi K, Pollok B A. Developing assays for kinase drug discovery—where have the advances come from? Expert Opin Drug Discov. 2008; 3:115-29.
63. Lebakken C S, Riddle S M, Singh U, Frazee W J, Eliason H C, Gao Y, Reichling U, Marks B D, Vogel K W. Development and applications of a broad-coverage, T R-FRET-based kinase binding assay platform. J Biomol Screen. 2009; 14:924-35.
64. Kashem M A, Nelson R M, Yingling J D, Pullen S S, Prokopowicz A S 3rd, Jones J W, Wolak J P, Rogers G R, Morelock M M, Snow R J, Homon C A, Jakes S. Three mechanistically distinct kinase assays compared: measurement of intrinsic ATPase activity identified the most comprehensive set of ITK inhibitors. J Biomol Screen. 2007; 12:70-83.
65. Marks B D, Thompson D V, Goossens T A, Trubetskoy O V. High-throughput screening assays for the assessment of CYP2C9*1, CYP2C9*2, and CYP2C9*3 metabolism using fluorogenic Vivid substrates. J Biomol Screen. 2004; 9:439—49.
66. Marks B D, Smith R W, Braun H A, Goossens T A, Christenson M, Ozers M S, Lebakken C S, Trubetskoy O V. A high throughput screening assay to screen for CYP2E1 metabolism and inhibition using a fluorogenic vivid p450 substrate. Assay Drug Dev Technol. 2002; 1:73-81.
67. Piper D R, Duff S R, Eliason H C, Frazee W J, Frey E A, Fuerstenau-Sharp M, Jachec C, Marks B D, Pollok B A, Shekhani M S, Thompson D V, Whitney P, Vogel K W, et al. Development of the predictor HERG fluorescence polarization assay using a membrane protein enrichment approach. Assay Drug Dev Technol. 2008; 6:213-23.
68. Hashizume R, Zhang A, Mueller S, Prados M D, Lulla R R, Goldman S, Saratsis A M, Mazar A P, Stegh A H, Cheng S Y, Horbinski C, Haas-Kogan D A, Sarkaria J N, et al. Inhibition of DNA damage repair by the CDK4/6 inhibitor palbociclib delays irradiated intracranial atypical teratoid rhabdoid tumor and glioblastoma xenograft regrowth. Neuro Oncol. 2016; 18:1519-28.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating a peripheral malignant rhabdoid tumor (MRT) in a subject in need thereof, the method comprising administering a pharmaceutical composition comprising an inhibitor of polo-like kinase 4 (PLK4) and a suitable pharmaceutical carrier, diluent, or excipient, wherein the inhibitor of PLK4 is a compound having the following Formula I or a pharmaceutically acceptable salt thereof:

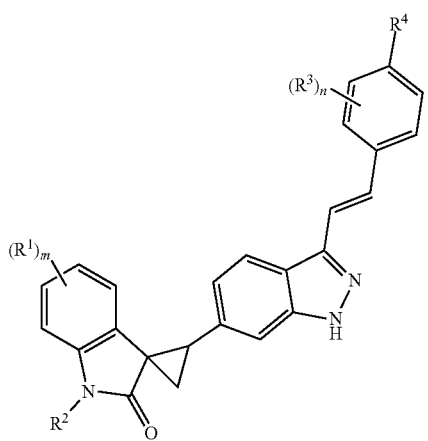

wherein:
m is 0-4 and each $R^1$ is independently halogen, hydroxyl, $C_{1-6}$ alkyl, $C_{1-6}$ haloalkyl, or $C_{1-6}$ alkoxy;
$R^2$ is hydrogen or $C_{1-6}$ alkyl;
n is 0-4 and each $R^3$ is independently halogen, hydroxyl, thiol, nitro, cyano, amino, $C_{1-6}$ alkyl, $C_{1-6}$ haloalkyl, or $C_{1-6}$ alkoxy;
$R^4$ is $C_{1-6}$ alkyl-N-morpholinyl, wherein the morpholinyl group optionally is substituted at one or more positions with $C_{1-6}$ alkyl.

2. The method of claim 1, wherein $R^4$ is N-2,6-dimethylmorpholinyl.

3. The method of claim 1, wherein the inhibitor of PLK4 is a compound having the following Formula Ia or a pharmaceutically acceptable salt thereof:

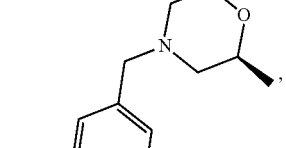

which otherwise is referred to as (1R,2S)-(E)-2-(3-(4-trans-2,6-dimethylmorpholino)methy)styryl)-1H-indazol-6-yl)-5'-methoxyspiro[cyclopropane-1,3'-indolin]-2' one or CFI-400945.

4. The method of claim 1, further comprising administering chemotherapy to the subject.

5. The method of claim 4, wherein administering chemotherapy to the subject comprises administering a DNA-damaging agent to the subject.

6. The method of claim 5, wherein the DNA-damaging agent is selected from the group consisting of cisplatin, carboplatin, oxaliplatin, methotrexate, doxorubicin, daunorubicin, and etoposide.

7. The method of claim 1, further comprising administering radiation therapy to the subject.

8. The method of claim 1, wherein the pharmaceutical composition is administered orally.

9. The method of claim 1, wherein the pharmaceutical composition is administered daily.

10. The method of claim 1, wherein the composition is administered twice a week.

11. The method of claim 1, wherein the composition is administered once a week.

* * * * *